United States Patent
Hanney et al.

(10) Patent No.: US 7,629,367 B2
(45) Date of Patent: Dec. 8, 2009

(54) N-(2-BENZYL)-2-PHENYLBUTANAMIDES AS ANDROGEN RECEPTOR MODULATORS

(75) Inventors: Barbara Hanney, Pennsburg, PA (US); Yuntae Kim, Harleysville, PA (US); Michael R. Krout, Pasedena, CA (US); Robert S. Meissner, Schwenksville, PA (US); Helen J. Mitchell, Richboro, PA (US); Jeffrey Musselman, Harleysville, PA (US); James J. Perkins, Churchsville, PA (US); Jiabing Wang, Chalfont, PA (US)

(73) Assignee: Merck & Co., Inc., Rahway, NJ (US)

( * ) Notice: Subject to any disclaimer, the term of this patent is extended or adjusted under 35 U.S.C. 154(b) by 3 days.

(21) Appl. No.: 11/628,685

(22) PCT Filed: Jun. 3, 2005

(86) PCT No.: PCT/US2005/019554

§ 371 (c)(1),
(2), (4) Date: Dec. 6, 2006

(87) PCT Pub. No.: WO2005/120477

PCT Pub. Date: Dec. 22, 2005

(65) Prior Publication Data

US 2008/0139630 A1    Jun. 12, 2008

Related U.S. Application Data

(60) Provisional application No. 60/577,698, filed on Jun. 7, 2004.

(51) Int. Cl.
*A61K 31/165* (2006.01)

(52) U.S. Cl. .................. 514/357; 514/312; 514/617; 514/169; 514/284; 546/333; 564/182; 564/123; 564/158

(58) Field of Classification Search .............. 514/357, 514/312, 617, 169, 284; 546/333; 564/182, 564/123, 158
See application file for complete search history.

(56) References Cited

U.S. PATENT DOCUMENTS

| | | | |
|---|---|---|---|
| 2,809,965 | A | 10/1957 | Wheeler et al. |
| 5,607,976 | A | 3/1997 | Englert et al. |
| 6,204,293 | B1 | 3/2001 | Sebti et al. |
| 6,727,239 | B1 | 4/2004 | Chabrier de Lassauniere et al. |
| 6,821,992 | B1 | 11/2004 | Cooke et al. |
| 7,268,153 | B2 | 9/2007 | Hanney et al. |
| 2003/0032623 | A1 | 2/2003 | Ban et al. |
| 2004/0053897 | A1* | 3/2004 | Dalton et al. ............... 514/169 |
| 2004/0087810 | A1 | 5/2004 | Dalton et al. |
| 2004/0122057 | A1 | 6/2004 | Banner et al. |
| 2004/0229904 | A1 | 11/2004 | Bunnage et al. |
| 2005/0009812 | A1 | 1/2005 | Seko et al. |
| 2005/0014763 | A1 | 1/2005 | Brown et al. |
| 2005/0143317 | A1 | 6/2005 | Abdel-Meguid et al. |
| 2005/0234097 | A1 | 10/2005 | Brown et al. |
| 2005/0282872 | A1 | 12/2005 | Hangeland et al. |

FOREIGN PATENT DOCUMENTS

| | | |
|---|---|---|
| EP | 1 193 248 A1 | 4/2002 |
| EP | 1 438 973 | 7/2004 |
| EP | 1 477 167 | 11/2004 |
| JP | 1-157955 | 11/1987 |
| WO | WO 00 39077 | 7/2000 |
| WO | WO 03 074473 | 9/2003 |
| WO | WO 2004/048335 | 6/2004 |
| WO | WO 2004 108676 | 12/2004 |
| WO | WO 2005 063690 | 7/2005 |
| WO | WO 2005 090287 | 9/2005 |

OTHER PUBLICATIONS

H. Shinji, "Novel Heterocyclic Derivative and Production Thereof", Patent Abstracts of Japan, vol. 013, No. 419, 1989.
C. Jamieson et al., "A Rapid Approach for the Optimisation of Polymer Supported Reagents in Synthesis", Synlett, No. 11, pp. 1603-1607, 2000.
Database Registry, Abstract, XP-002357059, 2004.
Patent Abstracts of Japan, vol. 13, No. 419, 1989 and JP 01 157955 included (see Item 25 on sheet 1 of 1449 form).
Database Registry, RN 329920-78-7, 2001.
U.S. Appl. No. 11/712,727, filed Mar. 1, 2007.
Ottow, Eckhard et al. "Nonsgteroidal Tissue-selective Androgen Receptor Modulators", 2008, 249-304, *Nuclear Receptor as Drug Targets*.

* cited by examiner

*Primary Examiner*—Ardin Marschel
*Assistant Examiner*—Savitha Rao
(74) *Attorney, Agent, or Firm*—Curtis C. Panzer; Valerie J. Camara

(57) ABSTRACT

Compounds of structural formula I are modulators of the androgen receptor (AR) in a tissue selective manner. These compounds are useful in the enhancement of weakened muscle tone and the treatment of conditions caused by androgen deficiency or which can be ameliorated by androgen administration, including osteoporosis, osteopenia, glucocorticoid-induced osteoporosis, periodontal disease bone fracture, bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, inflammatory arthritis and joint repair, HIV-wasting, prostate cancer, benign prostatic hyperplasia (BPH), abdominal adiposity, metabolic syndrome, type II diabetes, cancer cachexia, Alzheimer's disease, muscular dystrophies, cognitive decline, sexual dysfunction, sleep apnea, depression, premature ovarian failure, and autoimmune disease, alone or in combination with other active agents.

1 Claim, No Drawings

N-(2-BENZYL)-2-PHENYLBUTANAMIDES AS ANDROGEN RECEPTOR MODULATORS

This application is a §371 National Stage Application of PCT/US 2005/019554, filed on 03 Jun. 2005, which claims priority from U.S. Provisional Appln No. 60/577,698 filed on Jun. 7, 2004.

FIELD OF THE INVENTION

The present invention relates to N-(2-benzyl)-2-phenylbutanamide derivatives, their synthesis, and their use as androgen receptor modulators. More particularly, the compounds of the present invention are tissue-selective androgen receptor modulators (SARMs) and are thereby useful for the treatment of conditions caused by androgen deficiency or which can be ameliorated by androgen administration, such as osteoporosis, periodontal disease, bone fracture, frailty, and sarcopenia. Additionally, the SARMs of the present invention can be used to treat mental disorders associated with low testosterone, such as depression, sexual dysfunction, and cognitive decline. SARMs, being antagonists in specific tissues, are also useful in conditions where elevated androgen tone or activity causes symptoms, such as benign prostate hyperplasia and sleep apnea.

BACKGROUND OF THE INVENTION

The androgen receptor (AR) belongs to the superfamily of steroid/thyroid hormone nuclear receptors, whose other members include the estrogen receptor, the progesterone receptor, the glucocorticoid receptor, and the mineralocorticoid receptor. The AR is expressed in numerous tissues of the body and is the receptor through which the physiological as well as the pathophysiological effects of androgens, such as testosterone (T) and dihydrotestosterone (DHT), are mediated. Structurally, the AR is composed of three functional domains: the ligand binding domain (LBD), the DNA-binding domain, and amino-terminal domain. A compound that binds to the AR and mimics the effects of an endogenous AR ligand is referred to as an AR agonist, whereas a compound that inhibits the effects of an endogenous AR ligand is termed an AR antagonist.

Androgen ligand binding to the AR induces a ligand/receptor complex, which, after translocation into the nucleus of the cell, binds to regulatory DNA sequences (referred to as androgen response elements) within the promoter or enhancer regions of the target genes present in the nucleus. Other proteins termed cofactors are next recruited, which bind to the receptor leading to gene transcription.

Androgen therapy has been to treat a variety of male disorders such as reproductive disorders and primary or secondary male hypogonadism. Moreover, a number of natural or synthetic AR agonists have been investigated for the treatment of musculoskeletal disorders, such as bone disease, hematopoietic disorders, neuromuscular disease, rheumatological disease, wasting disease, and for hormone replacement therapy (HRT), such as female androgen deficiency. In addition, AR antagonists, such as flutamide and bicalutamide, are used to treat prostate cancer. It would therefore be useful to have available compounds that can activate ("agonize") the function of the AR in a tissue-selective manner that would produce the desired osteo- and myoanabolic effects of androgens without the negative androgenic properties, such as virilization and repression of high density lipoprotein cholesterol (HDL).

The beneficial effects of androgens on bone in postmenopausal osteoporosis were documented in recent studies using combined testosterone and estrogen administration [Hofbauer, et al., *Eur. J. Edocrinol.* 140: 271-286 (1999)]. In a large 2-year, double-blind comparison study, oral conjugated estrogen (CEE) and methyltestosterone combinations were demonstrated to be effective in promoting accrual of bone mass in the spine and hip, while conjugated estrogen therapy alone prevented bone loss [*J. Reprod. Med.*, 44: 1012-1020 (1999)].

Additionally, there is evidence that hot flushes decrease in women treated with CEE and methyltestosterone; however, 30% of the treated women suffered from significant increases in acne and facial hair, a complication of all current androgen pharmacotherapies [Watts, et al., *Obstet. Gynecol.*, 85: 529-537 (1995)]. It was also found that the addition of methyltestosterone to CEE decreased HDL levels, as seen in other studies. Thus, the virilizing potential and effects on lipid profile of current androgen therapies provide a rationale for developing tissue-selective androgen receptor agonists.

Androgens play an important role in bone metabolism in men [Anderson, et al., "Androgen supplementation in eugonadal men with osteoporosis—effects of six months of treatment on bone mineral density and cardiovascular risk factors," *Bone*, 18: 171-177 (1996)]. Even in eugonadal men with osteoporosis, the therapeutic response to testosterone treatment reveals that androgens exert important osteoanabolic effects. Mean lumbar BMD increased from 0.799 gm/cm2 to 0.839 g/cm2, in 5 to 6 months in response to 250 mg of testosterone ester administered intramuscularly. SARMs can thus be used to treat osteoporosis in men.

Androgen deficiency occurs in men with stage D prostate cancer (metastatic) who undergo androgen deprivation therapy (ADT). Endocrine orchiectomy is achieved by long acting GnRH agonists, while androgen receptor blockade is implemented with AR antagonists. In response to hormonal deprivation, these men suffered from hot flushes, significant bone loss, weakness, and fatigue. In a pilot study of men with stage D prostate cancer, osteopenia (50% vs. 38%) and osteoporosis (38% vs. 25%) were more common in men who had undergone ADT for greater than one year than the patients who did not undergo ADT [Wei, et al., *Urology*, 54: 607-611 (1999)]. Lumbar spine BMD was significantly lower in men who had undergone ADT. Thus tissue selective AR antagonists in the prostate that lack antagonistic action in bone and muscle can be useful agents for the treatment of prostate cancer, either alone or as an adjunct to traditional ADT [See also A. Stoch, et al., *J. Clin. Endocrin. Metab.*, 86: 2787-2791 (2001)].

Tissue-selective AR antagonists can also treat polycystic ovarian syndrome in postmenopausal women. See C. A. Eagleson, et al., "Polycystic ovarian syndrome: evidence that flutamide restores sensitivity of the gonadotropin-releasing hormone pulse generator to inhibition by estradiol and progesterone," *J. Clin. Endocrinol. Metab.*, 85: 4047-4052 (2000).

SARMs can also treat certain hematopoietic disorders as androgens stimulate renal hypertrophy and erythropoietin (EPO) production. Prior to the introduction of recombinant human EPO, androgens were employed to treat anemia caused by chronic renal failure. In addition, androgens increase serum EPO levels in anemic patients with non-severe aplastic anemia and myelodysplastic syndromes. Treatment for anemia will require selective action such as can be provided by SARMs.

SARMs can also have clinical value as an adjunct to the treatment of obesity. This approach to lowering body fat is supported by published observations that androgen administration reduced subcutaneous and visceral fat in obese patients [J. C. Lovejoy, et al., "Oral anabolic steroid treatment, but not parenteral androgen treatment, decreases abdominal fat in obese, older men," *Int. J. Obesity*, 19: 614-624 (1995)], [J. C. Lovejoy, et al., "Exogenous Androgens Influence Body Composition and Regional Body Fat Distribution in Obese Postmenopausal Women—A Clinical Research Center Study," *J. Clin. Endocrinol. Metab.*, 81: 2198-2203 (1996)]. Therefore, SARMs devoid of unwanted androgenic effects can be beneficial in the treatment of obesity.

Androgen receptor agonists can also have therapeutic value against metabolic syndrome (insulin resistance syndrome, syndrome X), particularly in men. Low levels of total and free testosterone and sex hormone-binding globulin (SHBG) in men have been associated with type 2 diabetes, visceral obesity, insulin resistance (hyperinsulinemia, dyslipidemia) and metabolic syndrome. D. Laaksonen, et al., *Diabetes Care*, 27 (5): 1036-1041(2004); see also D. Laaksonen, et al. *Euro. J Endocrin*, 149: 601-608 (2003); P. Márin, et al. *Int. J. Obesity*, 16: 991-997 (1992), and P. Márin, et al. *Obesity Res.*, 1(4): 245-251 (1993).

Androgen receptor agonists can also have therapeutic value against neurodegenerative diseases such as Alzheimer's disease (AD). The ability of androgens to induce neuroprotection through the androgen receptor was reported by J. Hammond, et al., "Testosterone-mediated neuroprotection through the androgen receptor in human primary neurons," *J. Neurochem.*, 77: 1319-1326 (2001). Gouras et al. reported that testosterone reduces secretion of Alzheimer's β-amyloid peptides and can therefore be used in the treatment of AD [(*Proc. Nat. Acad. Sci.*, 97: 1202-1205 (2000)]. A mechanism via inhibition of hyperphosphorylation of proteins implicated in the progression AD has also been described [S. Papasozomenos, "Testosterone prevents the heat shock-induced over activation of glycogen synthase kinase-3β but not of cyclin-dependent kinase 5 and c-Jun NH2-terminal kinase and concomitantly abolishes hyperphosphorylation of τ: Implications for Alzheimer's disease," *Proc. Nat. Acad. Sci.*, 99: 1140-1145 (2002)].

Androgen receptor agonists can also have a beneficial effect on muscle tone and strength. Recent studies have demonstrated that "physiologic androgen replacement in healthy, hypogonadal men is associated with significant gains in fat-free mass, muscle size and maximal voluntary strength," [S. Bhasin, et al., *J. Endocrin.*, 170: 27-38 (2001)].

Androgen receptor modulators can be useful in treating decreased libido in both men and women. Androgen deficiency in men is related to diminished libido. S. Howell et al., *Br. J. Cancer*, 82: 158-161. Low androgen levels contribute to the decline in sexual interest in many women during their later reproductive years. S. Davis, *J. Clin. Endocrinol. Metab.*, 84: 1886-1891 (1999). In one study, circulating free testosterone was positively correlated with sexual desire. Id. In another study, women with primary or secondary adrenal insufficiency were provided physiological DHEA replacement (50 mg/day). Compared with women taking placebo, DBEA-administered women showed an increase in the frequency of sexual thoughts, interest, and satisfaction. W. Arlt, et al., *N Engl. J. Med.* 341:1013-1020 (1999), see also, K. Miller, *J. Clin. Endocrinol. Metab.*, 86: 2395-2401 (2001).

Additionally, androgen receptor modulators may also be useful in treating cognitive impairment. In a recent study, high-dose oral estrogen either alone or in combination with high-dose oral methyltestosterone was given to postmenopausal women for a four-month period. Cognitive tests were administered before and after the four-month hormone treatment. The investigation found that women receiving a combination of estrogen (1.25 mg) and methyltestosterone (2.50 mg) maintained a steady level of performance on the Building Memory task, but the women receiving estrogen (1.25 mg) alone exhibited decreased performance. A. Wisniewski, *Horm. Res.* 58:150-155 (2002).

SUMMARY OF THE INVENTION

The present invention relates to compounds of structural formula I:

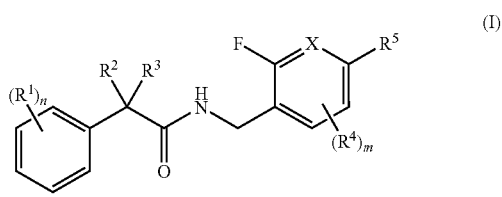

or a pharmaceutically acceptable salt or stereoisomer thereof, their uses, and pharmaceutical compositions.

These compounds are effective as androgen receptor agonists and are particularly effective as SARMs. They are therefore useful for the treatment of conditions caused by androgen deficiency or which can be ameliorated by androgen administration.

The present invention also relates to pharmaceutical compositions comprising the compounds of the present invention and a pharmaceutically acceptable carrier.

In this invention, we have identified compounds that function as SARMs using a series of in vitro cell-assays that profile ligand mediated activation of AR, such as (i) N—C interaction, (ii) transcriptional repression, and (iii) transcriptional activation. SARM compounds in this invention, identified with the methods listed above, exhibit tissue selective AR agonism in vivo, i.e. agonism in bone (stimulation of bone formation in a rodent model of osteoporosis) and antagonism in prostate (minimal effects on prostate growth in castrated rodents and antagonism of prostate growth induced by AR agonists).

The compounds of the present invention identified as SARMs are useful to treat diseases or conditions caused by androgen deficiency which can be ameliorated by androgen administration. Such compounds are ideal for the treatment of osteoporosis in women and men as a monotherapy or in combination with inhibitors of bone resorption, such as bisphosphonates, estrogens, SERMs, cathepsin K inhibitors, αvβ3 integrin receptor antagonists, calcitonin, and proton pump inhibitors. They can also be used with agents that stimulate bone formation, such as parathyroid hormone or analogs thereof. The SARM compounds of the present invention can also be employed for treatment of prostate disease, such as prostate cancer and benign prostatic hyperplasia (BPH). Moreover, compounds of this invention exhibit minimal effects on skin (acne and facial hair growth) and can be useful for treatment of hirsutism. Additionally, compounds of this invention can stimulate muscle growth and can be useful for treatment of sarcopenia and frailty. They can be employed to reduce visceral fat in the treatment of obesity. Moreover, compounds of this invention can exhibit androgen agonism in the central nervous system and can be useful to treat vasomotor symptoms (hot flush) and to increase energy and libido. They can be used in the treatment of Alzheimer's disease.

The compounds of the present invention can also be used in the treatment of prostate cancer, either alone or as an adjunct to GnRH agonist/antagonist therapy, for their ability to restore bone, or as a replacement for antiandrogen therapy because of their ability to antagonize androgen in the prostate, and minimize bone depletion. Further, the compounds of the present invention can be used for their ability to restore bone in the treatment of pancreatic cancer as an adjunct to treatment with antiandrogen, or as monotherapy for their antiandrogenic properties, offering the advantage over traditional antiandrogens of being bone-sparing. Additionally, compounds of this invention can increase the number of blood cells, such as red blood cells and platelets, and can be useful for the treatment of hematopoietic disorders, such as aplastic anemia. Thus, considering their tissue selective androgen receptor agonism listed above, the compounds of this invention are ideal for hormone replacement therapy in hypogonadic (androgen deficient) men.

This invention is also concerned with safely and specifically treating a male subject with abdominal adiposity, metabolic syndrome (also known as the 'insulin resistance syndrome', and 'Syndrome X'), and type II diabetes.

DETAILED DESCRIPTION OF THE INVENTION

The present invention relates to compounds that are useful as androgen receptor modulators, in particular, as selective androgen receptor modulators (SARMs). Compounds of the present invention are described by structural formula I:

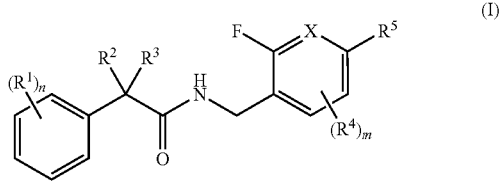

(I)

a pharmaceutically acceptable salt or a stereoisomer thereof, wherein:

X is —CH—, or —N—;
n is 0, 1, 2, or 3;
m is 0, 1, or 2;
$R^1$, $R^4$, and $R^5$ are each independently chosen from
  hydrogen,
  halogen,
  cyano,
  perfluoro$C_{1-6}$alkyl,
  perfluoro$C_{1-6}$alkoxy,
  $C_{1-10}$ alkyl,
  $C_{2-10}$ alkenyl,
  $C_{2-10}$ alkynyl,
  $C_{1-10}$ alkylthio,
  aryl $C_{0-10}$ alkyl,
  $C_{3-8}$ cycloalkyl $C_{0-10}$ alkyl,
  $C_{3-8}$ heterocyclyl $C_{2-10}$ alkyl,
  $C_{3-8}$ heterocycloalkyl $C_{2-10}$ alkyl,
  $(C_{0-10}$ alkyl$)_{1-2}$amino $C_{0-10}$ alkyl,
  (aryl $C_{0-10}$ alkyl$)_{1-2}$amino $C_{0-10}$ alkyl,
  $(C_{3-8}$ cycloalkyl $C_{0-10}$ alkyl$)_{1-2}$amino $C_{0-10}$ alkyl,
  $(C_{3-8}$ heterocyclyl $C_{0-10}$ alkyl$)_{1-2}$amino $C_{0-10}$ alkyl,
  $(C_{3-8}$ heterocycloalkyl $C_{0-10}$ alkyl$)_{1-2}$amino $C_{0-10}$ alkyl,
  $(C_{0-10}$ alkyl$)_{1-2}$aminocarbonylamino $C_{0-10}$ alkyl,
  (aryl $C_{0-10}$ alkyl$)_{1-2}$aminocarbonylamino $C_{0-10}$ alkyl,
  $C_{3-8}$ heterocyclyl $C_{0-10}$ alkyl aminocarbonylamino $C_{0-10}$ alkyl,
  $C_{3-8}$ heterocycloalkyl $C_{0-10}$ alkyl aminocarbonylamino $C_{0-10}$ alkyl,
  $C_{3-8}$ cycloalkyl $C_{0-10}$ alkyl aminocarbonylamino $C_{0-10}$ alkyl,
  $(C_{0-10}$ alkyl$)_{1-2}$aminocarbonyl $C_{0-10}$ alkyl,
  (aryl $C_{0-10}$ alkyl$)_{1-2}$aminocarbonyl $C_{0-10}$ alkyl,
  $C_{3-8}$ cycloalkyl $C_{0-10}$ alkyl aminocarbonyl $C_{0-10}$ alkyl,
  $C_{3-8}$ heterocyclyl $C_{0-10}$ alkyl aminocarbonyl $C_{0-10}$ alkyl,
  $C_{3-8}$ heterocycloalkyl $C_{0-10}$ alkyl aminocarbonyl $C_{0-10}$ alkyl,
  $C_{0-10}$ alkyl carbonylamino $C_{0-10}$ alkyl,
  $C_{3-8}$ cycloalkyl $C_{0-10}$ alkyl carbonylamino $C_{0-10}$ alkyl,
  $C_{3-8}$ heterocyclyl $C_{0-10}$ alkyl carbonylamino $C_{0-10}$ alkyl,
  $C_{3-8}$ heterocycloalkyl $C_{0-10}$ alkyl carbonylamino $C_{0-10}$ alkyl,
  aryl $C_{0-10}$ alkyl carbonylamino $C_{0-10}$ alkyl,
  $C_{0-10}$ alkyloxy carbonylamino $C_{0-10}$ alkyl,
  $C_{3-8}$ cycloalkyl $C_{0-10}$ alkyloxy carbonylamino $C_{0-10}$ alkyl,
  $C_{3-8}$ heterocyclyl $C_{0-10}$ alkyloxy carbonylamino $C_{0-10}$ alkyl,
  $C_{3-8}$ heterocycloalkyl $C_{0-10}$ alkyloxy carbonylamino $C_{0-10}$ alkyl,
  aryl $C_{0-10}$ alkyloxy carbonylamino $C_{0-10}$ alkyl,
  $C_{0-10}$ alkyloxy carbonyloxy $C_{0-10}$ alkyl,
  $C_{3-8}$ cycloalkyl $C_{0-10}$ alkyloxy carbonyloxy $C_{0-10}$ alkyl,
  $C_{3-8}$ heterocyclyl $C_{0-10}$ alkyloxy carbonyloxy $C_{0-10}$ alkyl,
  $C_{3-8}$ heterocycloalkyl $C_{0-10}$ alkyloxy carbonyloxy $C_{0-10}$ alkyl,
  aryl $C_{0-10}$ alkyloxy carbonyloxy $C_{0-10}$ alkyl,
  $C_{1-10}$ alkoxy(carbonyl$)_{0-1}C_{0-10}$ alkyl,
  $C_{0-10}$ alkylcarboxy $C_{0-10}$ alkylamino,
  hydroxycarbonyl $C_{1-10}$ alkyl,
  hydroxycarbonyl $C_{2-10}$ alkenyl,
  hydroxycarbonyl $C_{2-10}$ alkynyl,
  $C_{1-10}$alkoxy,
  $C_{1-10}$alkyloxy $C_{0-10}$alkyl,
  aryloxy $C_{0-10}$ alkyl,
  $C_{3-8}$ cycloalkyloxy $C_{0-10}$ alkyl,
  $C_{3-8}$ heterocyclyl $C_{2-10}$alkyl oxy $C_{0-10}$ alkyl,
  $C_{3-8}$ heterocycloalkyl$C_{2-10}$alkyloxy $C_{0-10}$ alkyl,
  $C_{1-10}$ alkylcarbonyloxy $C_{0-10}$ alkyl,
  $(C_{0-10}$ alkyl$)_{1-2}$aminosulfonyl $C_{0-10}$ alkyl,
  (aryl $C_{0-10}$ alkyl$)_{1-2}$aminosulfonyl $C_{0-10}$ alkyl,
  $C_{3-8}$ cycloalkyl $C_{0-10}$ alkyl aminosulfonyl $C_{0-10}$ alkyl,
  $C_{3-8}$ heterocyclyl $C_{0-10}$ alkyl aminosulfonyl $C_{0-10}$ alkyl,
  $C_{3-8}$ heterocycloalkyl $C_{0-10}$ alkyl aminosulfonyl $C_{0-10}$ alkyl,
  $C_{0-10}$ alkyl sulfonylamino $C_{0-10}$ alkyl,
  $C_{3-8}$ cycloalkyl $C_{0-10}$ alkyl sulfonylamino $C_{0-10}$ alkyl,
  $C_{3-8}$ heterocyclyl $C_{0-10}$ alkyl sulfonylamino $C_{0-10}$ alkyl,
  $C_{3-8}$ heterocycloalkyl $C_{0-10}$ alkyl sulfonylamino $C_{0-10}$ alkyl,
  aryl $C_{0-10}$ alkyl sulfonylamino $C_{0-10}$ alkyl,
  $C_{1-10}$ alkyloxy(carbonyl$)_{0-1}C_{0-10}$ alkylamino,
  $C_{3-8}$ heterocyclyl $C_{0-10}$ alkyloxy(carbonyl$)_{0-1}C_{0-10}$ alkylamino,
  $C_{3-8}$ heterocycloalkyl $C_{0-10}$ alkyloxy(carbonyl$)_{0-1}C_{0-10}$ alkylamino,
  $C_{3-8}$ cycloalkyl $C_{0-10}$ alkyloxy(carbonyl$)_{0-1}C_{0-10}$ alkylamino,
  aryl $C_{0-10}$ alkyloxy(carbonyl$)_{0-1}C_{0-10}$ alkylamino,
  $(C_{0-10}$ alkyl$)_{1-2}$aminocarbonyloxy,
  (aryl $C_{0-10}$ alkyl$)_{1-2}$aminocarbonyloxy,
  $(C_{3-8}$ heterocyclyl $C_{0-10}$ alkyl$)_{1-2}$aminocarbonyloxy,
  $(C_{3-8}$ heterocycloalkyl $C_{0-10}$ alkyl$)_{1-2}$aminocarbonyloxy, ($C_{3-8}$ cycloalkyl $C_{0-10}$alkyl)$_{1-2}$aminocarbonyloxy, and
hydroxy $C_{0-10}$alkyl,
and provided that when X is —N— then $R^5$ is other than a moiety chosen from ($C_{0-10}$ alkyl)$_{1-2}$amino, $C_{0-10}$ alkyloxy carbonylamino, $C_{3-8}$ cycloalkyl $C_{0-10}$ alkyloxy carbonylamino, aryl $C_{0-10}$ alkyloxy carbonylamino, $C_{1-10}$ alkyloxy(carbonyl)$_{0-1}$$C_{0-10}$ alkylamino, $C_{1-10}$ alkyloxy(carbonyl)$_{0-1}$$C_{0-10}$ alkylamino, $C_{3-8}$ cycloalkyl $C_{0-10}$ alkyloxy(carbonyl)$_{0-1}$$C_{0-10}$ alkylamino, and aryl $C_{0-10}$ alkyloxy(carbonyl)$_{0-1}$$C_{0-10}$ alkylamino;

$R^2$ and $R^3$ are each independently chosen from
hydrogen,
halogen,
cyano,
amino,
hydroxy $C_{0-10}$alkyl,
perfluoro$C_{1-6}$alkyl,
perfluoro$C_{1-6}$alkoxy,
$C_{1-10}$ alkyl,
$C_{2-10}$ alkenyl,
$C_{2-10}$ alkynyl,
aryl $C_{0-10}$ alkyl,
$C_{3-8}$ cycloalkyl $C_{0-10}$ alkyl,
$C_{3-8}$ heterocyclyl $C_{0-10}$ alkyl,
$C_{3-8}$ heterocycloalkyl $C_{0-10}$ alkyl,
($C_{0-10}$ alkyl)$_{1-2}$amino $C_{0-10}$ alkyl,
(aryl $C_{0-10}$ alkyl)$_{1-2}$amino $C_{0-10}$ alkyl,
($C_{3-8}$ cycloalkyl $C_{0-10}$ alkyl)$_{1-2}$amino $C_{0-10}$ alkyl,
($C_{3-8}$ heterocyclyl $C_{0-10}$ alkyl)$_{1-2}$amino $C_{0-10}$ alkyl,
($C_{3-8}$ heterocycloalkyl $C_{0-10}$ alkyl)$_{1-2}$amino $C_{0-10}$ alkyl,
($C_{0-10}$ alkyl)$_{1-2}$aminocarbonyloxy $C_{0-10}$ alkyl,
(aryl $C_{0-10}$ alkyl)$_{1-2}$aminocarbonyloxy $C_{0-10}$ alkyl,
($C_{3-8}$ cycloalkyl $C_{0-10}$ alkyl)$_{1-2}$aminocarbonyloxy $C_{0-10}$ alkyl,
($C_{3-8}$ heterocyclyl $C_{0-10}$ alkyl)$_{1-2}$aminocarbonyloxy $C_{0-10}$ alkyl,
($C_{3-8}$ heterocycloalkyl $C_{0-10}$ alkyl)$_{1-2}$aminocarbonyloxy $C_{0-10}$ alkyl,
($C_{0-10}$ alkyl)$_{1-2}$aminocarbonylamino$C_{0-10}$ alkyl,
(aryl $C_{0-10}$ alkyl)$_{1-2}$aminocarbonylamino $C_{0-10}$ alkyl,
($C_{3-8}$ cycloalkyl $C_{0-10}$ alkyl)$_{1-2}$aminocarbonylamino $C_{0-10}$ alkyl,
($C_{3-8}$ heterocyclyl $C_{0-10}$ alkyl)$_{1-2}$aminocarbonylamino $C_{0-10}$ alkyl,
($C_{3-8}$ heterocycloalkyl$C_{0-10}$alkyl)$_{1-2}$aminocarbonylamino $C_{0-10}$ alkyl,
($C_{0-10}$ alkyl)$_{1-2}$aminocarbonyl $C_{0-10}$ alkyl,
(aryl $C_{0-10}$ alkyl)$_{1-2}$aminocarbonyl $C_{0-10}$ alkyl,
$C_{3-8}$ cycloalkyl $C_{0-10}$ alkyl aminocarbonyl $C_{0-10}$ alkyl,
$C_{3-8}$ heterocyclyl $C_{0-10}$ alkyl aminocarbonyl $C_{0-10}$ alkyl,
$C_{3-8}$ heterocycloalkyl $C_{0-10}$ alkyl aminocarbonyl $C_{0-10}$ alkyl,
$C_{0-10}$ alkyl carbonylamino $C_{0-10}$ alkyl,
$C_{3-8}$ cycloalkyl $C_{0-10}$ alkyl carbonylamino $C_{0-10}$ alkyl,
$C_{3-8}$ heterocyclyl $C_{0-10}$ alkyl carbonylamino $C_{0-10}$ alkyl,
$C_{3-8}$ heterocycloalkyl $C_{0-10}$ alkyl carbonylamino $C_{0-10}$ alkyl,
aryl $C_{0-10}$ alkyl carbonylamino $C_{0-10}$ alkyl,
$C_{0-10}$ alkyloxy carbonylamino $C_{0-10}$ alkyl,
$C_{3-8}$ cycloalkyl $C_{0-10}$ alkyloxy carbonylamino $C_{0-10}$ alkyl,
$C_{3-8}$ heterocyclyl $C_{0-10}$ alkyloxy carbonylamino $C_{0-10}$ alkyl,
$C_{3-8}$ heterocycloalkyl $C_{0-10}$ alkyloxy carbonylamino $C_{0-10}$ alkyl,
aryl $C_{0-10}$ alkyloxy carbonylamino $C_{0-10}$ alkyl,
arylcarbonyloxy$C_{0-10}$ alkyl,
$C_{3-8}$ heterocycloalkylcarbonyloxy$C_{0-10}$ alkyl,
$C_{3-8}$cycloalkylcarbonyloxy$C_{0-10}$ alkyl,
$C_{3-8}$ heterocyclylcarbonyloxy$C_{0-10}$ alkyl,
$C_{0-10}$ alkyloxy carbonyloxy $C_{0-10}$ alkyl,
$C_{3-8}$ cycloalkyl $C_{0-10}$ alkyloxy carbonyloxy $C_{0-10}$ alkyl,
$C_{3-8}$ heterocyclyl $C_{0-10}$ alkyloxy carbonyloxy $C_{0-10}$ alkyl,
$C_{3-8}$ heterocycloalkyl $C_{0-10}$ alkyloxy carbonyloxy $C_{0-10}$ alkyl,
aryl $C_{0-10}$ alkyloxy carbonyloxy $C_{0-10}$ alkyl,
$C_{1-10}$ alkoxy(carbonyl)$_{0-1}$$C_{0-10}$ alkyl,
$C_{0-10}$ alkylcarboxy $C_{0-10}$ alkylamino,
$C_{1-10}$alkyloxy $C_{0-10}$alkyl,
aryloxy $C_{0-10}$ alkyl,
$C_{3-8}$ cycloalkyloxy $C_{0-10}$ alkyl,
$C_{3-8}$ heterocyclyloxy $C_{0-10}$ alkyl,
$C_{3-8}$ heterocyclyl$C_{0-10}$alkyloxy $C_{0-10}$ alkyl,
$C_{1-10}$ alkylcarbonyloxy $C_{0-10}$ alkyl,
$C_{1-10}$ alkyloxy(carbonyl)$_{0-1}$$C_{0-10}$ alkylamino,
$C_{3-8}$ heterocyclyl $C_{0-10}$ alkyloxy(carbonyl)$_{0-1}$$C_{0-10}$ alkylamino,
$C_{3-8}$ heterocycloalkyl $C_{0-10}$ alkyloxy(carbonyl)$_{0-1}$$C_{0-10}$ alkylamino,
$C_{3-8}$ cycloalkyl $C_{0-10}$ alkyloxy(carbonyl)$_{0-1}$$C_{0-10}$ alkylamino; and
aryl $C_{0-10}$ alkyloxy(carbonyl)$_{0-1}$$C_{0-10}$ alkylamino, and
wherein in $R^1$, $R^2$, $R^3$, $R^4$, and $R^5$, said alkyl, alkenyl, alkynyl, aryl, heterocyclyl, heterocycloalkyl, and cycloalkyl are each optionally substituted with one or more groups chosen from hydroxy, $C_{1-6}$ alkyl, $C_{1-6}$ alkoxy, halogen, $CO_2H$, cyano, $O(C=O)C_1$-$C_6$ alkyl, $NO_2$, trifluoromethoxy, trifluoroethoxy, —$O_{(0-1)}(C_{1-10})$perfluoroalkyl, $C_{0-10}$ alkylaminocarbonylamino, $C_{1-10}$ alkyloxycarbonylamino, $C_{1-10}$ alkylcarbonylamino, $C_{0-10}$ alkylaminosulfonylamino, $C_{1-10}$ alkylsulfonylamino, $C_{1-10}$ alkylsulfonyl, $C_{0-10}$ alkylaminosulfonyl, $C_{0-10}$ alkylaminocarbonyl and $NH_2$.

In another embodiment of the invention, compounds are described by structural formula II:

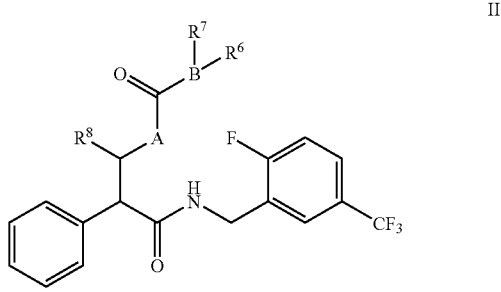

a pharmaceutically acceptable salt or a stereoisomer thereof, wherein:

A and B are each independently chosen from —CH—, —N— and —O—;

$R^6$ and $R^7$ are each independently chosen from
hydrogen,
halogen,
cyano,
amino,
hydroxy $C_{0-9}$alkyl;
perfluoro$C_{1-6}$alkyl,
perfluoro$C_{1-6}$alkoxy,
$C_{1-9}$ alkyl,
$C_{2-9}$ alkenyl,
$C_{2-9}$ alkynyl, aryl $C_{0-9}$ alkyl,
$C_{3-8}$ cycloalkyl $C_{0-9}$ alkyl,
$C_{3-8}$ heterocyclyl $C_{0-9}$ alkyl,
$C_{3-8}$ heterocycloalkyl $C_{0-9}$ alkyl,
$(C_{0-10}$ alkyl$)_{1-2}$amino $C_{0-9}$ alkyl,
(aryl $C_{0-10}$ alkyl$)_{1-2}$amino $C_{0-9}$ alkyl,
$(C_{3-8}$ cycloalkyl $C_{0-10}$ alkyl$)_{1-2}$amino $C_{0-9}$ alkyl,
$(C_{3-8}$ heterocyclyl $C_{0-10}$ alkyl$)_{1-2}$amino $C_{0-9}$ alkyl,
$(C_{3-8}$ heterocycloalkyl $C_{0-10}$ alkyl$)_{1-2}$amino $C_{0-9}$ alkyl,
$(C_{0-10}$ alkyl$)_{1-2}$aminocarbonyloxy $C_{0-9}$ alkyl,
(aryl $C_{0-10}$ alkyl$)_{1-2}$aminocarbonyloxy $C_{0-9}$ alkyl,
$(C_{3-8}$ cycloalkyl $C_{0-10}$ alkyl$)_{1-2}$aminocarbonyloxy $C_{0-9}$ alkyl,
$(C_{3-8}$ heterocyclyl $C_{0-10}$ alkyl$)_{1-2}$aminocarbonyloxy $C_{0-9}$ alkyl,
$(C_{3-8}$ heterocycloalkyl $C_{0-10}$ alkyl$)_{1-2}$aminocarbonyloxy $C_{0-9}$ alkyl,
$(C_{0-10}$ alkyl$)_{1-2}$aminocarbonylamino$C_{0-9}$ alkyl,
(aryl $C_{0-10}$ alkyl$)_{1-2}$aminocarbonylamino $C_{0-9}$ alkyl,
$(C_{3-8}$ cycloalkyl $C_{0-10}$ alkyl$)_{1-2}$aminocarbonylamino $C_{0-9}$ alkyl,
$(C_{3-8}$ heterocyclyl $C_{0-10}$ alkyl$)_{1-2}$aminocarbonylamino $C_{0-9}$ alkyl,
$(C_{3-8}$ heterocycloalkyl$C_{0-10}$ alkyl$)_{1-2}$aminocarbonylamino $C_{0-9}$ alkyl,
$(C_{0-10}$ alkyl$)_{1-2}$aminocarbonyl $C_{0-9}$ alkyl,
(aryl $C_{0-10}$ alkyl$)_{1-2}$aminocarbonyl $C_{0-9}$ alkyl,
$C_{3-8}$ cycloalkyl $C_{0-10}$ alkyl aminocarbonyl $C_{0-9}$ alkyl,
$C_{3-8}$ heterocyclyl $C_{0-10}$ alkyl aminocarbonyl $C_{0-9}$ alkyl,
$C_{3-8}$ heterocycloalkyl $C_{0-10}$ alkyl aminocarbonyl $C_{0-9}$ alkyl,
$C_{0-10}$ alkyl carbonylamino $C_{0-9}$ alkyl,
$C_{3-8}$ cycloalkyl $C_{0-10}$ alkyl carbonylamino $C_{0-9}$ alkyl,
$C_{3-8}$ heterocyclyl $C_{0-10}$ alkyl carbonylamino $C_{0-9}$ alkyl,
$C_{3-8}$ heterocycloalkyl $C_{0-10}$ alkyl carbonylamino $C_{0-9}$ alkyl,
aryl $C_{0-10}$ alkyl carbonylamino $C_{0-9}$ alkyl,
$C_{0-10}$ alkyloxy carbonylamino $C_{0-9}$ alkyl,
$C_{3-8}$ cycloalkyl $C_{0-10}$ alkyloxy carbonylamino $C_{0-9}$ alkyl,
$C_{3-8}$ heterocyclyl $C_{0-10}$ alkyloxy carbonylamino $C_{0-9}$ alkyl,
$C_{3-8}$ heterocycloalkyl $C_{0-10}$ alkyloxy carbonylamino $C_{0-9}$ alkyl,
aryl $C_{0-10}$ alkyloxy carbonylamino $C_{0-9}$ alkyl,
$C_{0-10}$ alkyloxy carbonyloxy $C_{0-9}$ alkyl,
$C_{3-8}$ cycloalkyl $C_{0-10}$ alkyloxy carbonyloxy $C_{0-9}$ alkyl,
$C_{3-8}$ heterocyclyl $C_{0-10}$ alkyloxy carbonyloxy $C_{0-9}$ alkyl,
$C_{3-8}$ heterocycloalkyl $C_{0-10}$ alkyloxy carbonyloxy $C_{0-9}$ alkyl,
aryl $C_{0-10}$ alkyloxy carbonyloxy $C_{0-9}$ alkyl,
$C_{1-10}$ alkoxy(carbonyl)$_{0-1}C_{0-9}$ alkyl,
$C_{1-10}$alkyloxy $C_{0-9}$ alkyl,
aryloxy $C_{0-9}$ alkyl,
$C_{3-8}$ cycloalkyloxy $C_{0-9}$ alkyl,
$C_{3-8}$ heterocyclyloxy $C_{0-9}$ alkyl,
$C_{3-8}$ heterocyclyl$C_{0-10}$alkyloxy $C_{0-9}$ alkyl, and
$C_{1-10}$ alkylcarbonyloxy $C_{0-9}$ alkyl, and
wherein in $R^6$, and $R^7$, said alkyl, alkenyl, alkynyl, aryl, heterocyclyl, heterocycloalkyl, and cycloalkyl are each optionally substituted with one or more groups chosen from hydroxy, $C_{1-6}$ alkyl, $C_{1-6}$ alkoxy, halogen, $CO_2H$, cyano, $O(C=O)C_1-C_6$ alkyl, $NO_2$, trifluoromethoxy, trifluoroethoxy, $—O_{(0-1)}(C_{1-10})$perfluoroalkyl, $C_{0-10}$ alkylaminocarbonylamino, $C_{1-10}$ alkyloxycarbonylamino, $C_{1-10}$ alkylcarbonylamino, $C_{0-10}$ alkylaminosulfonylamino, $C_{1-10}$ alkylsulfonylamino, $C_{1-10}$ alkylsulfonyl, $C_{0-10}$ alkylaminosulfonyl, $C_{0-10}$ alkylaminocarbonyl and $NH_2$; and $R^8$ is chosen from hydrogen, hydroxy, $C_{1-6}$ alkyl, $C_{1-6}$ alkoxy, halogen, $CO_2H$, cyano, $O(C=O)C_1-C_6$ alkyl, $NO_2$, trifluoromethoxy, trifluoroethoxy, $—O_{(0-1)}(C_{1-10})$perfluoroalkyl, $C_{0-10}$ alkylaminocarbonylamino, $C_{1-10}$ alkyloxycarbonylamino, $C_{1-10}$ alkylcarbonylamino, $C_{0-10}$ alkylaminosulfonylamino, $C_{1-10}$ alkylsulfonylamino, $C_{1-10}$ alkylsulfonyl, $C_{0-10}$ alkylaminosulfonyl, $C_{0-10}$ alkylaminocarbonyl and $NH_2$.

Illustrative but nonlimiting examples of compounds of the present invention are the following:

(S)—N-(2-fluoro-5-(trifluoromethyl)benzyl)-2-phenylbutanamide;
N-(2-fluoro-5-methylbenzyl)-2-phenylbutanamide;
(S)—N-((2-fluoro-5-(trifluoromethyl)pyridin-3-yl)methyl)-2-phenylbutanamide;
(S)—N-(5-bromo-2-fluorobenzyl)-2-phenylbutanamide;
N-(2-fluoro-5-(trifluoromethyl)benzyl)-2-phenylbutanamide;
N-(5-ethyl-2-fluorobenzyl)-2-phenylbutanamide;
(S)—N-(5-ethyl-2-fluorobenzyl)-2-phenylbutanamide;
N-(5-cyclopropyl-2-fluorobenzyl)-2-phenylbutanamide;
N-(2-fluoro-5-vinylbenzyl)-2-phenylbutanamide;
N-(2-fluoro-5-(trifluoromethyl)benzyl)-2-(3-fluorophenyl)butanamide;
N-(5-ethyl-2-fluorobenzyl)-2-(4-chlorophenyl)butanamide;
N-((2-fluoro-5-methylpyridini-3-yl)methyl)-2-phenylbutanamide;
(S)—N-((2-fluoro-5-methylpyridin-3-yl)methyl)-2-phenylbutanamide;
(S)—N-((5-ethyl-2-fluoropyridin-3-yl)methyl)-2-phenylbutanamide;
N-(5-bromo-2-fluorobenzyl)-2-phenylbutanamide;
N-(5-ethyl-2-fluorobenzyl)-2-(3-chlorophenyl)butanamide;
N-(5-ethyl-2-fluorobenzyl)-2-(3,4-dichlorophenyl)butanamide;
(S)—N-((5-cyclopropyl-2-fluoropyridin-3-yl)methyl)-2-phenylbutanamide;
(2R or 2S)—N-[(5-cyclopropyl-2-fluoropyridin-3-yl)methyl]-2-(3,4-dichlorophenyl)butanamide;
(2R or 2S)—N-[(5-ethyl-2-fluoropyridin-3-yl)methyl]-2-(3,4-dichlorophenyl)butanamide;
(2R or 2S)—N-[(5-methyl-2-fluoropyridin-3-yl)methyl]-2-(3,4-dichlorophenyl)butanamide;
(2R or 2S)—N-(2-fluoro-5-(trifluoromethyl)benzyl)-2-(3-bromophenyl)butanamide;
(2R or 2S)—N-(5-bromo-2-fluorobenzyl)-2-(3-bromophenyl)butanamide;
(2R or 2S)—N-(5-(cyclopropyl)-2-fluorobenzyl)-2-(3-bromophenyl)butanamide;
(2R or 2S)—N-(5-chloro-2-fluorobenzyl)-2-(4-bromophenyl)butanamide;
(2R or 2S)—N-(2-fluoro-5-(trifluoromethyl)benzyl)-2-(4-bromophenyl)butanamide;
(2R or 2S)—N-(5-bromo-2-fluorobenzyl)-2-(4-bromophenyl)butanamide;
(2R or 2S)—N-(5-(cyclopropyl)-2-fluorobenzyl)-2-(4-bromophenyl)butanamide;
N-[5-(1,1-difluoroethyl)-2-fluorobenzyl]-2-phenylbutanamide;
(2R or 2S)—N-(2-fluoro-5-(trifluoromethyl)benzyl)-2-hydroxy-2-phenylbutanamide;
(2R or 2S)—N-(2-fluoro-5-(trifluoromethyl)benzyl)-2-(3-chlorophenyl)-2-hydroxybutanamide;
(2R or 2S)—N-((2-fluoro-5-methylpyridin-3-yl)methyl)-2-hydroxy-2-phenylbutanamide;
(2R or 2S)-2-cyclopropyl-N-((2-fluoro-5-methylpyridin-3-yl)methyl)-2-hydroxy-2-phenylacetamide;

(2R or 2S)—N-((5-ethyl-2-fluoropyridin-3-yl)methyl)-2-hydroxy-2-phenylbutanamide;
(2R)-3,3,3-trifluoro-N-[(2-fluoro-5-methylpyridin-3-yl)methyl]-2-hydroxy-2-phenylpropanamide;
(2R or 2S)-3,3,4,4,4-pentafluoro-N-[(2-fluoro-5-methylpyridin-3-yl)methyl]-2-hydroxy-2-phenylbutanamide;
(2R)-3,3,3-trifluoro-N-(2-fluoro-5-trifluoromethylbenzyl)-2-hydroxy-2-phenylpropanamide;
(2R)-3,3,3-trifluoro-N-(2-fluoro-5-ethylbenzyl)-2-hydroxy-2-phenylpropanamide;
(2R)-3,3,3-trifluoro-N-(2-fluoro-5-bromobenzyl)-2-hydroxy-2-phenylpropanamide;
(2R)-3,3,3-trifluoro-N-(2-fluoro-5-chlorobenzyl)-2-hydroxy-2-phenylpropanamide;
(2R)-3,3,3-trifluoro-N-(2-fluoro-5-trifluoromethylbenzyl)-2-hydroxy-2-phenylpropanamide;
(2R or 2S)-3,3,4,4,4-pentafluoro-N-(2-fluoro-5-cyclopropylbenzyl)-2-hydroxy-2-phenylbutanamide;
(2R or 2S)-3,3,4,4,4-pentafluoro-N-(2-fluoro-5-trifluoromethylbenzyl)-2-hydroxy-2-phenylbutanamide;
(2R)-3,3,3-trifluoro-N-(2,3,5-trifluorobenzyl)-2-hydroxy-2-phenylpropanamide;
(2R or 2S)-2-(4-chloro-3-fluorophenyl)-3,3,3-trifluoro-[2-fluoro-5-(trifluoromethyl)benzyl]-2-hydroxypropanamide;
(2R or 2S)-2-(4-chloro-3-fluorophenyl)-3,3,3-trifluoro-[2-fluoro-5-(trifluoromethyl)benzyl]-2-hydroxypropanamide;
(2R)-3,3,3-trifluoro-N-(2-fluoro-3-bromo-5-trifluoromethylbenzyl)-2-hydroxy-2-phenylpropanamide;
(2R)-3,3,3-trifluoro-N-(2-fluoro-3-cyano-5-trifluoromethylbenzyl)-2-hydroxy-2-phenylpropanamide;
(2R)-3,3,3-trifluoro-N-(2-fluoro-4-cyano-5-ethylbenzyl)-2-hydroxy-2-phenylpropanamide;

and pharmaceutically acceptable salts and stereoisomers thereof.

The compounds of the present invention can have asymmetric centers, chiral axes, and chiral planes (as described in: E. L. Eliel and S. H. Wilen, *Stereochemnistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.). The term "$C_0$ alkyl" (as in "$C_{0-8}$ alkylaryl") shall refer to the absence of an alkyl group.

The term "alkenyl" shall mean straight or branched chain alkenes of two to ten total carbon atoms, or any number within this range.

The term "alkynyl" refers to a hydrocarbon radical straight, branched or cyclic, containing from 2 to 10 carbon atoms and at least one carbon to carbon triple bond. Up to three carbon-carbon triple bonds can be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group can contain triple bonds and can be substituted if a substituted alkynyl group is indicated.

"Cycloalkyl" as used herein is intended to include non-aromatic cyclic hydrocarbon groups, having the specified number of carbon atoms, which may or may not be bridged or structurally constrained. Examples of such cycloalkyls include, but are not limited to, cyclopropyl, cyclobutyl, cyclopentyl, cyclohexyl, adamantyl, cyclooctyl, cycloheptyl, tetrahydro-naphthalene, methylenecylohexyl, and the like. As used herein, examples of "$C_3$-$C_{10}$ cycloalkyl" can include, but are not limited to:

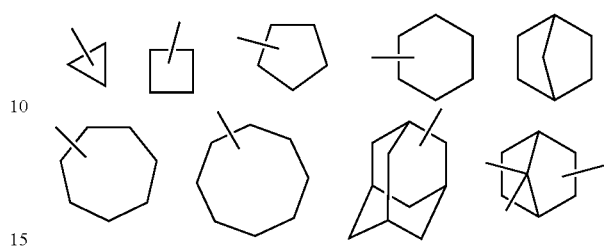

"Alkoxy" represents either a cyclic or non-cyclic alkyl group of indicated number of carbon atoms attached through an oxygen bridge. "Alkoxy" therefore encompasses the definitions of alkyl and cycloalkyl above.

"Perfluoroalkyl" represents alkyl chains of up to 10 carbon atoms having exhaustive substitution of their corresponding hydrogens with fluorine atoms.

As used herein, "aryl" is intended to mean any stable monocyclic or bicyclic carbon ring of up to 7 atoms in each ring, wherein at least one ring is aromatic. Examples of such aryl elements include, but are not limited to, phenyl, naphthyl, tetrahydro-naphthyl, indanyl, or biphenyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms chosen from O, N and S. Heteroaryl groups within the scope of this definition include but are not limited to: azabenzimidazole, acridinyl, carbazolyl, cinnolinyl benzimidazolyl, benzofuranyl, benzothiophenyl, benzoxazolyl, benzothiazolyl, benzodihydrofuranyl, 1,3-benzodioxolyl, 2,3-dihydro-1,4-benzodioxinyl, indolyl, quinolyl, quinoxalinyl, isoquinolyl, furanyl, thienyl, imidazolyl, oxazolyl, thiazolyl, isoxazolyl, isothiazolyl, pyrazolyl, pyrrolyl, pyridyl, pyrimidyl, pyrazinyl, piridazinyl, tetrahydroquinolinyl, thiadiazolyl, oxadiazolyl, triazolyl, imidizopyridinyl, tetrazolyl, and indanyl. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

Whenever the term "alkyl" or "aryl" or either of their prefix roots appears in a name of a substituent (e.g., aryl $C_{0-8}$ alkyl), it shall be interpreted as including those limitations given above for "alkyl" and "aryl." Designated numbers of carbon atoms (e.g., $C_{0-8}$) shall refer independently to the number of carbon atoms in an alkyl or cyclic alkyl moiety or to the alkyl portion of a larger substituent in which alkyl appears as its prefix root.

As appreciated by those of skill in the art, "halo" or "halogen" as used herein is intended to include chloro, fluoro, bromo and iodo.

The term "heterocycle" or "heterocyclyl" as used herein is intended to mean a 5- to 14-membered aromatic or nonaromatic ring system containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: azabenzimidazole, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

The terms "arylalkyl" and "alkylaryl" include an alkyl portion where alkyl is as defined above and include an aryl portion where aryl is as defined above. Examples of arylalkyl include, but are not limited to, benzyl, phenylethyl, phenylpropyl, naphthylmethyl, and naphthylethyl. Examples of alkylaryl include, but are not limited to, toluene, ethylbenzene, propylbenzene, methylpyridine, ethylpyridine, propylpyridine and butylpyridine.

The term "oxy" means an oxygen (O) atom. The term "thio" means a sulfur (S) atom. The term "oxo" means "=O". The term "carbonyl" means "C=O."

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

When any variable (e.g., $R^5$, $R^6$, etc.) occurs more than one time in any substituent or in formula I, its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

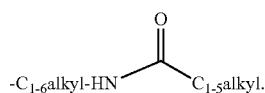

In choosing compounds of the present invention, one of ordinary skill in the art will recognize that the various substituents, i.e. $R^1$, $R^2$, $R^3$, $R^4$, $R^5$ etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

In one embodiment, X is —CH—. In another embodiment, X is —N—.

In one embodiment of the invention, $R^1$, $R^4$, and $R^5$ are each independently chosen from hydrogen, halogen, cyano, perfluoro$C_{1-6}$alkyl, $C_{1-10}$ alkyl, $C_{2-10}$ alkenyl, aryl $C_{0-10}$ alkyl, $C_{3-8}$ cycloalkyl $C_{0-10}$ alkyl, $C_{3-8}$ heterocyclyl $C_{2-10}$ alkyl, $C_{3-8}$ heterocycloalkyl $C_{2-10}$ alkyl, $C_{0-10}$ alkylamino $C_{0-10}$ alkyl, $C_{3-8}$ cycloalkyl $C_{0-10}$ alkylamino $C_{0-10}$ alkyl, aryl $C_{0-10}$ alkylamino $C_{0-10}$ alkyl, $C_{3-8}$ heterocyclyl $C_{0-10}$ alkylamino $C_{0-10}$ alkyl, $C_{3-8}$ heterocycloalkyl $C_{0-10}$ alkylamino $C_{0-10}$ alkyl, $C_{0-10}$ alkyl aminocarbonyl $C_{0-10}$ alkyl, $C_{3-8}$ cycloalkyl $C_{0-10}$ alkyl aminocarbonyl $C_{0-10}$ alkyl, $C_{3-8}$ heterocyclyl $C_{0-10}$ alkyl aminocarbonyl $C_{0-10}$ alkyl, $C_{3-8}$ heterocycloalkyl $C_{0-10}$ alkyl aminocarbonyl $C_{0-10}$ alkyl, aryl $C_{0-10}$ alkyl aminocarbonyl $C_{0-10}$ alkyl, $C_{0-10}$ alkyl carbonylamino $C_{0-10}$ alkyl, $C_{3-8}$ cycloalkyl $C_{0-10}$ alkyl carbonylamino $C_{0-10}$ alkyl, $C_{3-8}$ heterocyclyl $C_{0-10}$ alkyl carbonylamino $C_{0-10}$ alkyl, $C_{3-8}$ heterocycloalkyl $C_{0-10}$ alkyl carbonylamino $C_{0-10}$ alkyl, aryl $C_{0-10}$ alkyl carbonylamino $C_{0-10}$ alkyl, $C_{0-10}$ alkylcarboxy $C_{0-10}$ alkylamino, hydroxycarbonyl $C_{1-10}$ alkyl, hydroxycarbonyl $C_{2-10}$ alkenyl, $C_{1-10}$ alkoxy, $C_{1-10}$alkyloxy $C_{0-10}$alkyl, aryloxy $C_{0-10}$ alkyl, $C_{3-8}$ cycloalkyloxy $C_{0-10}$ alkyl, $C_{3-8}$ heterocyclyl $C_{2-10}$alkyl oxy $C_{0-10}$ alkyl, $C_{3-8}$ heterocycloalkyl$C_{2-10}$alkyloxy $C_{0-10}$ alkyl, $C_{1-10}$ alkylcarbonyloxy $C_{0-10}$ alkyl, $C_{0-10}$ alkyl aminosulfonyl $C_{0-10}$ alkyl, $C_{0-10}$ alkyl sulfonylamino $C_{0-10}$ alkyl, aryl $C_{0-10}$ alkyl sulfonylamino $C_{0-10}$ alkyl, $C_{1-10}$ alkyloxy(carbonyl)$_{0-1}$$C_{0-10}$ alkylamino, $C_{3-8}$ heterocyclyl $C_{0-10}$ alkyloxy(carbonyl)$_{0-1}$ $C_{0-10}$ alkylamino, $C_{3-8}$ heterocycloalkyl $C_{0-10}$ alkyloxy(carbonyl)$_{0-1}$$C_{0-10}$ alkylamino, $C_{3-8}$ cycloalkyl $C_{0-10}$ alkyloxy (carbonyl)$_{0-1}$$C_{0-10}$ alkylamino, aryl $C_{0-10}$ alkyloxy (carbonyl)$_{0-1}$$C_{0-10}$ alkylamino, cyano, and hydroxy $C_{0-10}$alkyl; wherein in $R^1$, $R^4$, and $R^5$, said alkyl, alkenyl, alkynyl, aryl, heterocyclyl, heterocycloalkyl, and cycloalkyl are each optionally substituted with one or more groups chosen from hydroxy, $C_{1-6}$ alkyl, $C_{1-6}$ alkoxy, halogen, $CO_2H$, cyano, $O(C=O)C_1$-$C_6$ alkyl, $NO_2$, trifluoromethoxy, trifluoroethoxy, —$O_{(0-1)}(C_{1-10})$perfluoroalkyl, $C_{0-10}$ alkylaminocarbonylamino, $C_{1-10}$ alkyloxycarbonylamino, $C_{1-10}$ alkylcarbonylamino, $C_{0-10}$ alkylaminosulfonylamino, $C_{1-10}$ alkylsulfonylamino, $C_{1-10}$ alkylsulfonyl, $C_{0-10}$ alkylaminosulfonyl, $C_{0-10}$ alkylaminocarbonyl and $NH_2$.

In other embodiment of the invention, $R^1$, $R^4$, and $R^5$ are each independently chosen from hydrogen, halogen, cyano, perfluoro$C_{1-6}$alkyl, $C_{1-10}$ alkyl, $C_{2-10}$ alkenyl, perfluoro$C_{1-6}$ alkoxy, $C_{2-10}$ alkynyl, $C_{1-10}$ alkylthio, ($C_{1-10}$ alkyl)$_2$amino $C_{0-10}$ alkyl, (aryl $C_{0-10}$ alkyl)$_2$amino $C_{0-10}$ alkyl, ($C_{3-8}$ cycloalkyl $C_{0-10}$ alkyl)$_2$amino $C_{0-10}$ alkyl, ($C_{3-8}$ heterocyclyl $C_{0-10}$ alkyl)$_2$amino $C_{0-10}$ alkyl, ($C_{3-8}$ heterocycloalkyl $C_{0-10}$ alkyl)$_2$amino $C_{0-10}$ alkyl, ($C_{1-10}$ alkyl)$_2$aminocarbonylamino $C_{0-10}$ alkyl, (aryl $C_{0-10}$ alkyl)$_{1-2}$aminocarbonylamino $C_{0-10}$ alkyl, $C_{0-10}$ alkyl aminocarbonylamino $C_{0-10}$ alkyl, $C_{3-8}$ cycloalkyl $C_{0-10}$ alkyl aminocarbonylamino $C_{0-10}$ alkyl, $C_{3-8}$ heterocyclyl $C_{0-10}$ alkyl aminocarbonylamino $C_{0-10}$ alkyl, $C_{3-8}$ heterocycloalkyl $C_{0-10}$ alkyl aminocarbonylamino $C_{0-10}$ alkyl, ($C_{1-10}$ alkyl)$_2$aminocarbonyl $C_{0-10}$ alkyl, (aryl $C_{0-10}$ alkyl)$_{1-2}$aminocarbonyl $C_{0-10}$ alkyl, $C_{0-10}$ alkyloxy carbonylamino $C_{0-10}$ alkyl, $C_{3-8}$ cycloalkyl $C_{0-10}$ alkyloxy carbonylamino $C_{0-10}$ alkyl, $C_{3-8}$ heterocyclyl $C_{0-10}$ alkyloxy carbonylamino $C_{0-10}$ alkyl, $C_{3-8}$ heterocycloalkyl $C_{0-10}$ alkyloxy carbonylamino $C_{0-10}$ alkyl, aryl $C_{0-10}$ alkyloxy carbonylamino $C_{0-10}$ alkyl, $C_{0-10}$ alkyloxy carbonyloxy $C_{0-10}$ alkyl, $C_{3-8}$ cycloalkyl $C_{0-10}$ alkyloxy carbonyloxy $C_{0-10}$ alkyl, $C_{3-8}$ heterocyclyl $C_{0-10}$ alkyloxy carbonyloxy $C_{0-10}$ alkyl hydroxycarbonyl $C_{2-10}$ alkynyl, $C_{3-8}$ heterocycloalkyl $C_{0-10}$ alkyloxy carbonyloxy $C_{0-10}$ alkyl, aryl $C_{0-10}$ alkyloxy carbonyloxy $C_{0-10}$ alkyl, $C_{1-10}$ alkoxy (carbonyl)$_{0-1}C_{0-10}$ alkyl, ($C_{1-10}$ alkyl)$_2$aminosulfonyl $C_{0-10}$ alkyl, (aryl $C_{0-10}$ alkyl)$_{1-2}$-aminosulfonyl $C_{0-10}$ alkyl, $C_{3-8}$ cycloalkyl $C_{0-10}$ alkyl aminosulfonyl $C_{0-10}$ alkyl, $C_{3-8}$ heterocyclyl $C_{0-10}$ alkyl aminosulfonyl $C_{0-10}$ alkyl, $C_{3-8}$ heterocycloalkyl $C_{0-10}$ alkyl aminosulfonyl $C_{0-10}$ alkyl, aryl $C_{0-10}$ alkyl aminosulfonyl $C_{0-10}$ alkyl, $C_{3-8}$ cycloalkyl $C_{0-10}$ alkyl sulfonylamino $C_{0-10}$ alkyl, $C_{3-8}$ heterocyclyl $C_{0-10}$ alkyl sulfonylamino $C_{0-10}$ alkyl, $C_{3-8}$ heterocycloalkyl $C_{0-10}$ alkyl sulfonylamino $C_{0-10}$ alkyl, ($C_{1-10}$ alkyl)$_2$aminocarbonyloxy, (aryl $C_{0-10}$ alkyl)$_{1-2}$aminocarbonyloxy, ($C_{3-8}$ heterocyclyl $C_{0-10}$ alkyl)$_{1-2}$aminocarbonyloxy, ($C_{3-8}$ heterocycloalkyl $C_{0-10}$ alkyl)$_{1-2}$aminocarbonyloxy, cyano, and ($C_{3-8}$ cycloalkyl $C_{0-10}$alkyl)$_{1-2}$ aminocarbonyloxy; wherein in $R^1$, $R^4$, and $R^5$, said alkyl, alkenyl, alkynyl, aryl, heterocyclyl, heterocycloalkyl, and cycloalkyl are each optionally substituted with one or more groups chosen from hydroxy, $C_{1-6}$ alkyl, $C_{1-6}$ alkoxy, halogen, $CO_2H$, cyano, $O(C=O)C_1$-$C_6$ alkyl, $NO_2$, trifluoromethoxy, trifluoroethoxy, —$O_{(0-1)}(C_{1-10})$perfluoroalkyl, $C_{0-10}$ alkylaminocarbonylamino, $C_{1-10}$ alkyloxycarbonylamino, $C_{1-10}$ alkylcarbonylamino, $C_{0-10}$ alkylaminosulfonylamino, $C_{1-10}$ alkylsulfonylamino, $C_{1-10}$ alkylsulfonyl, $C_{0-10}$ alkylaminosulfonyl, $C_{0-10}$ alkylaminocarbonyl and $NH_2$.

In one embodiment of the invention, $R^2$ and $R^3$ are each independently chosen from hydrogen, halogen, amino, hydroxy $C_{0-10}$alkyl, perfluoro$C_{1-6}$ alkyl, perfluoro$C_{1-6}$ alkoxy, $C_{1-10}$ alkyl, $C_{2-10}$ alkenyl, aryl $C_{0-10}$ alkyl, $C_{3-8}$ heterocyclyl $C_{0-10}$ alkyl, ($C_{0-10}$ alkyl)$_{1-2}$ amino $C_{0-10}$ alkyl, (aryl $C_{0-10}$ alkyl)$_{1-2}$amino $C_{0-10}$ alkyl, ($C_{3-8}$ heterocyclyl $C_{0-10}$ alkyl)$_{1-2}$amino $C_{0-10}$ alkyl, ($C_{0-10}$ alkyl)$_{1-2}$aminocarbonyloxy $C_{0-10}$ alkyl, (aryl $C_{0-10}$ alkyl)$_{1-2}$arylaminocarbonyloxy $C_{0-10}$ alkyl, ($C_{0-10}$ alkyl)$_{1-2}$aminocarbonylamino$C_{0-10}$ alkyl, (aryl $C_{0-10}$ alkyl)$_{1-2}$aminocarbonylamino $C_{0-10}$ alkyl, ($C_{3-8}$ heterocyclyl $C_{0-10}$ alkyl)$_{1-2}$aminocarbonyloxy $C_{0-10}$ alkyl, ($C_{0-10}$ alkyl)$_{1-2}$-aminocarbonyl $C_{0-10}$ alkyl, (aryl $C_{0-10}$ alkyl)$_{1-2}$aminocarbonyl $C_{0-10}$ alkyl, $C_{3-8}$ heterocyclyl $C_{0-10}$ alkyl aminocarbonyl $C_{0-10}$ alkyl, ($C_{3-8}$ heterocyclyl $C_{0-10}$ alkyl)$_{1-2}$aminocarbonylamino $C_{0-10}$ alkyl, aryl $C_{0-10}$ alkylcarbonylamino $C_{0-10}$ alkyl, $C_{0-10}$ alkylcarboxy $C_{0-10}$ alkylamino, $C_{1-10}$alkyloxy $C_{0-10}$alkyl, aryloxy, $C_{3-8}$ heterocyclyl$C_{0-10}$alkyloxy, $C_{1-10}$ alkylcarbonyloxy, arylcarbonyloxy$C_{0-10}$ alkyl, $C_{3-8}$ heterocycloalkylcarbonyloxy$C_{0-10}$ alkyl, $C_{3-8}$cycloalkylcarbonyloxy$C_{0-10}$ alkyl, $C_{3-8}$ heterocyclylcarbonyloxy$C_{0-10}$ alkyl, aryl $C_{0-10}$ alkyloxy(carbonyl)$_{0-1}C_{0-10}$ alkylamino, ($C_{0-10}$ alkyl)$_2$aminocarbonyloxy, (aryl $C_{0-10}$alkyl)$_{1-2}$aminocarbonyloxy, wherein in $R^2$, and $R^3$, said alkyl, alkenyl, alkynyl, aryl, heterocyclyl, heterocycloalkyl, and cycloalkyl are each optionally substituted with one or more groups chosen from hydroxy, $C_{1-6}$ alkyl, $C_{1-6}$ alkoxy, halogen, $CO_2H$, cyano, $O(C=O)C_1$-$C_6$ alkyl, $NO_2$, trifluoromethoxy, trifluoroethoxy, —$O_{(0-1)}(C_{1-10})$perfluoroalkyl, $C_{0-10}$ alkylaminocarbonylamino, $C_{1-10}$ alkyloxycarbonylamino, $C_{1-10}$ alkylcarbonylamino, arylcarbonyloxy$C_{0-10}$ alkyl, $C_{3-8}$ heterocycloalkylcarbonyloxy$C_{0-10}$ alkyl, $C_{3-8}$cycloalkylcarbonyloxy$C_{0-10}$ alkyl, $C_{3-8}$ heterocyclylcarbonyloxy$C_{0-10}$ alkyl, $C_{0-10}$ alkylaminosulfonylamino, $C_{1-10}$ alkylsulfonylamino, $C_{1-10}$ alkylsulfonyl, $C_{0-10}$ alkylaminosulfonyl, $C_{0-10}$ alkylaminocarbonyl and $NH_2$.

In one embodiment, $R^2$ and $R^3$ are each independently chosen from cyano, $C_{2-10}$ alkynyl, $C_{3-8}$ cycloalkyl $C_{0-10}$ alkyl, $C_{3-8}$ heterocycloalkyl $C_{0-10}$ alkyl, ($C_{3-8}$ cycloalkyl $C_{0-10}$ alkyl)$_{1-2}$amino $C_{0-10}$ alkyl, ($C_{3-8}$ heterocycloalkyl $C_{0-10}$ alkyl)$_{1-2}$amino $C_{0-10}$ alkyl, ($C_{3-8}$ cycloalkyl $C_{0-10}$ alkyl)$_{1-2}$aminocarbonyloxy $C_{0-10}$ alkyl, ($C_{3-8}$ heterocycloalkyl $C_{0-10}$ alkyl)$_{1-2}$-aminocarbonyloxy $C_{0-10}$ alkyl, ($C_{3-8}$ cycloalkyl $C_{0-10}$ alkyl)$_{1-2}$aminocarbonylamino $C_{0-10}$ alkyl, ($C_{3-8}$ heterocycloalkyl $C_{0-10}$ alkyl)$_{1-2}$aminocarbonylamino $C_{0-10}$ alkyl, $C_{3-8}$ cycloalkyl $C_{0-10}$ alkyl aminocarbonyl $C_{0-10}$ alkyl, $C_{3-8}$ heterocycloalkyl$C_{0-10}$ alkyl aminocarbonyl$C_{0-10}$ alkyl, $C_{0-10}$ alkyl carbonylamino $C_{0-10}$ alkyl, $C_{3-8}$ cycloalkyl $C_{0-10}$ alkyl carbonylamino $C_{0-10}$ alkyl, $C_{3-8}$ heterocyclyl $C_{0-10}$ alkyl carbonylamino $C_{0-10}$ alkyl, $C_{3-8}$ heterocycloalkyl$C_{0-10}$ alkyl carbonylamino $C_{0-10}$ alkyl, $C_{0-10}$ alkyloxy carbonylamino $C_{0-10}$ alkyl, $C_{3-8}$ cycloalkyl $C_{0-10}$ alkyloxy carbonylamino $C_{0-10}$ alkyl, $C_{3-8}$ heterocyclyl $C_{0-10}$ alkyloxy carbonylamino $C_{0-10}$ alkyl, $C_{3-8}$ heterocycloalkyl $C_{0-10}$ alkyloxy carbonylamino $C_{0-10}$ alkyl, aryl $C_{0-10}$ alkyloxy carbonylamino $C_{0-10}$ alkyl, $C_{0-10}$ alkyloxy carbonyloxy $C_{0-10}$ alkyl, $C_{3-8}$ cycloalkyl $C_{0-10}$ alkyloxy carbonyloxy $C_{0-10}$ alkyl, $C_{3-8}$ heterocyclyl $C_{0-10}$ alkyloxy carbonyloxy $C_{0-10}$ alkyl, $C_{3-8}$ heterocycloalkyl $C_{0-10}$ alkyloxy carbonyloxy $C_{0-10}$ alkyl, aryl $C_{0-10}$ alkyloxy carbonyloxy $C_{0-10}$ alkyl, $C_{1-10}$ alkoxy(carbonyl)$_{0-1}C_{0-10}$ alkyl, $C_{3-8}$ cycloalkyloxy, $C_{3-8}$ heterocyclyloxy, $C_{1-10}$ alkyloxy(carbonyl)$_{0-1}C_{0-10}$ alkylamino, $C_{3-8}$ heterocyclyl $C_{0-10}$ alkyloxy(carbonyl)$_{0-1}C_{0-10}$ alkylamino, $C_{3-8}$ heterocycloalkyl $C_{0-10}$ alkyloxy(carbonyl)$_{0-1}C_{0-10}$ alkylamino, $C_{3-8}$ cycloalkyl $C_{0-10}$ alkyloxy(carbonyl)$_{0-1}C_{0-10}$ alkylamino, ($C_{3-8}$ heterocyclyl $C_{0-10}$ alkyl)$_{1-2}$aminocarbonyloxy, ($C_{3-8}$ heterocycloalkyl $C_{0-10}$ alkyl)$_{1-2}$aminocarbonyloxy, and ($C_{3-8}$ cycloalkyl$C_{0-10}$alkyl)$_{1-2}$-aminocarbonyloxy; arylcarbonyloxy$C_{0-10}$ alkyl, $C_{3-8}$ heterocycloalkylcarbonyloxy$C_{0-10}$ alkyl, $C_{3-8}$cycloalkylcarbonyloxy$C_{0-10}$ alkyl, and $C_{3-8}$ heterocyclylcarbonyloxy$C_{0-10}$ alkyl, and wherein in $R^2$, and $R^3$ said alkyl, alkenyl, alkynyl, aryl, heterocyclyl, heterocycloalkyl, and cycloalkyl are each optionally substituted with one or more groups chosen from hydroxy, $C_{1-6}$ alkyl, $C_{1-6}$ alkoxy, halogen, $CO_2H$, cyano, $O(C=O)C_1$-$C_6$ alkyl, $NO_2$, trifluoromethoxy, trifluoroethoxy, —$O_{(0-1)}(C_{1-10})$perfluoroalkyl, $C_{0-10}$ alkylaminocarbonylamino, $C_{1-10}$ alkyloxycarbonylamino, $C_{1-10}$ alkylcarbonylamino, $C_{0-10}$ alkylaminosulfonylamino, $C_{1-10}$ alkylsulfonylamino, $C_{1-10}$ alkylsulfonyl, $CO_{0-10}$ alkylaminosulfonyl, $C_{0-10}$ alkylaminocarbonyl and $NH_2$.

In one embodiment of the compounds of structural formula II, $R^6$ and $R^7$ are each independently chosen from hydrogen, halogen, cyano, amino, hydroxy $C_{0-9}$alkyl, perfluoro$C_{1-6}$ alkyl, perfluoro$C_{1-6}$alkoxy, $C_{1-9}$ alkyl, aryl $C_{0-9}$ alkyl, $C_{3-8}$ cycloalkyl $C_{0-9}$ alkyl, $C_{3-8}$ heterocyclyl $C_{0-9}$ alkyl, ($C_{0-10}$ alkyl)$_{1-2}$ amino $C_{0-9}$ alkyl, (aryl $C_{0-10}$ alkyl)$_{1-2}$amino $C_{0-9}$ alkyl, ($C_{3-8}$ heterocyclyl $C_{0-10}$ alkyl)$_{1-2}$amino $C_{0-9}$ alkyl, ($C_{0-10}$ alkyl)$_{1-2}$aminocarbonyloxy $C_{0-9}$ alkyl, (aryl $C_{0-10}$ alkyl)$_{1-2}$aminocarbonyloxy $C_{0-9}$ alkyl, ($C_{0-10}$ alkyl)$_{1-2}$aminocarbonylamino$C_{0-9}$ alkyl, (aryl$C_{0-10}$ alkyl)$_{1-2}$aminocarbonylamino $C_{0-9}$ alkyl, $C_{0-10}$ alkyl carbonylamino $C_{0-9}$ alkyl, aryl $C_{0-10}$ alkyl carbonylamino $C_{0-9}$ alkyl, $C_{0-10}$ alkyloxy carbonylamino $C_{0-9}$ alkyl, $C_{3-8}$ heterocyclyl $C_{0-10}$ alkyloxy carbonylamino $C_{0-9}$ alkyl, aryl $C_{0-10}$ alkyloxy carbonylamino $C_{0-9}$ alkyl, $C_{0-10}$ alkyloxy carbonyloxy $C_{0-9}$ alkyl, $C_{3-8}$ heterocyclyl$C_{0-10}$alkyloxy $C_{0-9}$ alkyl, and $C_{1-10}$ alkylcarbonyloxy $C_{0-9}$ alkyl, and wherein in $R^6$, and $R^7$, said alkyl, alkenyl, alkynyl, aryl, heterocyclyl, heterocycloalkyl, and cycloalkyl are each optionally substituted with one or more groups chosen from hydroxy, $C_{1-6}$ alkyl, $C_{1-6}$ alkoxy, halogen, $CO_2H$, cyano, $O(C=O)C_1-C_6$ alkyl, $NO_2$, trifluoromethoxy, trifluoroethoxy, $-O_{(0-1)}(C_{1-10})$perfluoroalkyl, $C_{0-10}$ alkylaminocarbonylamino, $C_{1-10}$ alkyloxycarbonylamino, $C_{1-10}$ alkylcarbonylamino, $C_{0-10}$ alkylaminosulfonylamino, $C_{1-10}$ alkylsulfonylamino, $C_{1-10}$ alkylsulfonyl, $C_{0-10}$ alkylaminosulfonyl, $C_{0-10}$ alkylaminocarbonyl and $NH_2$.

In another embodiment, $R^6$ and $R^7$ are each independently chosen from hydrogen, $C_{2-9}$ alkenyl, $C_{2-9}$ alkynyl, $C_{3-8}$ heterocycloalkyl $C_{0-9}$ alkyl, ($C_{3-8}$ cycloalkyl $C_{0-10}$ alkyl)$_{1-2}$ amino $C_{0-9}$ alkyl, ($C_{3-8}$ heterocycloalkyl$C_{0-10}$ alkyl)$_{1-2}$amino $C_{0-9}$ alkyl, ($C_{3-8}$ cycloalkyl $C_{0-10}$ alkyl)$_{1-2}$-aminocarbonyloxy $C_{0-9}$ alkyl, ($C_{3-8}$ heterocyclyl $C_{0-10}$ alkyl)$_{1-2}$aminocarbonyloxy $C_{0-9}$ alkyl, ($C_{3-8}$ heterocycloalkyl $C_{0-10}$ alkyl)$_{1-2}$ aminocarbonyloxy$C_{0-9}$ alkyl, ($C_{3-8}$ cycloalkyl$C_{0-10}$ alkyl)$_{1-2}$ aminocarbonylamino $C_{0-9}$ alkyl, ($C_{3-8}$ heterocyclyl $C_{0-10}$ alkyl)$_{1-2}$aminocarbonylamino $C_{0-9}$ alkyl, ($C_{3-8}$ heterocycloalkyl $C_{0-10}$ alkyl)$_{1-2}$aminocarbonylamino $C_{0-9}$ alkyl, ($C_{0-10}$ alkyl)$_{1-2}$aminocarbonyl $C_{0-9}$ alkyl, (aryl $C_{0-10}$ alkyl)$_{1-2}$ aminocarbonyl $C_{0-9}$ alkyl, $C_{3-8}$ cycloalkyl $C_{0-10}$ alkyl aminocarbonyl $C_{0-9}$ alkyl, $C_{3-8}$ heterocyclyl $C_{0-10}$ alkyl aminocarbonyl $C_{0-9}$ alkyl, $C_{3-8}$ heterocycloalkyl $C_{0-10}$ alkyl aminocarbonyl $C_{0-9}$ alkyl, $C_{3-8}$ cycloalkyl $C_{0-10}$ alkyl carbonylamino $C_{0-9}$ alkyl, $C_{3-8}$ heterocyclyl $C_{0-10}$ alkyl carbonylamino $C_{0-9}$ alkyl, $C_{3-8}$ heterocycloalkyl $C_{0-10}$ alkyl carbonylamino $C_{0-9}$ alkyl, $C_{3-8}$ cycloalkyl $C_{0-10}$ alkyloxy carbonylamino $C_{0-9}$ alkyl, $C_{3-8}$ heterocyclalkyl $C_{0-10}$ alkyloxy carbonylamino $C_{0-9}$ alkyl, $C_{3-8}$ cycloalkyl$C_{0-10}$alkyloxy carbonyloxy $C_{0-9}$ alkyl, $C_{3-8}$ heterocyclyl $C_{0-10}$ alkyloxy carbonyloxy $C_{0-9}$ alkyl, $C_{3-8}$ heterocycloalkyl $C_{0-10}$ alkyloxy carbonyloxy $C_{0-9}$ alkyl, aryl $C_{0-10}$ alkyloxy carbonyloxy $C_{0-9}$ alkyl, $C_{1-10}$ alkoxy(carbonyl)$_{0-1}C_{0-9}$ alkyl, $C_{1-10}$alkyloxy $C_{0-9}$alkyl, aryloxy $C_{0-9}$ alkyl, $C_{3-8}$ cycloalkyloxy $C_{0-9}$ alkyl, $C_{3-8}$ heterocyclyloxy $C_{0-9}$ alkyl, $C_{3-8}$ heterocyclyl$C_{0-10}$alkyloxy $C_{0-9}$ alkyl, and $C_{1-10}$ alkylcarbonyloxy $C_{0-9}$ alkyl, and wherein in $R^6$ and $R^7$, said alkyl, alkenyl, alkynyl, aryl, heterocyclyl, heterocycloalkyl, and cycloalkyl are each optionally substituted with one or more groups chosen from hydroxy, $C_{1-6}$ alkyl, $C_{1-6}$ alkoxy, halogen, $CO_2H$, cyano, $O(C=O)C_1-C_6$ alkyl, $NO_2$, trifluoromethoxy, trifluoroethoxy, $-O_{(0-1)}(C_{1-10})$perfluoroalkyl, $C_{0-10}$ alkylaminocarbonylamino, $C_{1-10}$ alkyloxycarbonylamino, $C_{1-10}$ alkylcarbonylamino, $C_{0-10}$ alkylaminosulfonylamino, $C_{1-10}$ alkylsulfonylamino, $C_{1-10}$ alkylsulfonyl, $C_{0-10}$ alkylaminosulfonyl, $C_{0-10}$ alkylaminocarbonyl and $NH_2$.

In one embodiment, the compounds of the present invention are chosen from (2R)—N-[(5-cyclopropyl-2-fluoropyridin-3-yl)methyl]-2-(3,4-dichlorophenyl)butanamide; (2R)—N-[(5-ethyl-2-fluoropyridin-3-yl)methyl]-2-(3,4-dichlorophenyl)butanamide; (2R)—N-[(5-methyl-2-fluoropyridin-3-yl)methyl]-2-(3,4-dichlorophenyl)butanamide; (2R)—N-(2-fluoro-5-(trifluoromethyl)benzyl)-2-(3-bromophenyl)butanamide; (2R)—N-(5-bromo-2-fluorobenzyl)-2-(3-bromophenyl)butanamide; (2R)—N-(5-(cyclopropyl)-2-fluorobenzyl)-2-(3-bromophenyl)butanamide; (2R)-3,3,3-trifluoro-N-(2-fluoro-5-trifluoromethylbenzyl)-2-hydroxy-2-phenylpropanamide; (2R)—N-(5-chloro-2-fluorobenzyl)-2-(4-bromophenyl)butanamide; (2R)—N-(2-fluoro-5-(trifluoromethyl)benzyl)-2-(4-bromophenyl)butanamide; (2R)—N-(5-bromo-2-fluorobenzyl)-2-(4-bromophenyl)butanamide; (2R)—N-(5-(cyclopropyl)-2-fluorobenzyl)-2-(4-bromophenyl)butanamide; (2R)—N-(2-fluoro-5-(trifluoromethyl)benzyl)-2-hydroxy-2-phenylbutanamide; (2R)—N-(2-fluoro-5-(trifluoromethyl)benzyl)-2-(3-chlorophenyl)-2-hydroxybutanamide; (2R)—N-((2-fluoro-5-methylpyridin-3-yl)methyl)-2-hydroxy-2-phenylbutanamide; (2R)-2-cyclopropyl-N-((2-fluoro-5-methylpyridin-3-yl)methyl)-2-hydroxy-2-phenylacetamide; (2R)—N-((5-ethyl-2-fluoropyridin-3-yl)methyl)-2-hydroxy-2-phenylbutanamide; (2R)-3,3,4,4,4-pentafluoro-N-[(2-fluoro-5-methylpyridin-3-yl)methyl]-2-hydroxy-2-phenylbutanamide; (2R)-2-(4-chloro-3-fluorophenyl)-3,3,3-trifluoro-[2-fluoro-5-(trifluoromethyl)benzyl]-2-hydroxypropanamide; (2R)-3-{[2-fluoro-5-(trifluoromethyl)benzyl]amino}-3-oxo-2-phenylpropyl dimethylcarbamate; (2R)-3-{[2-fluoro-5-(trifluoromethyl)benzyl]amino}-3-oxo-2-phenylpropyl pyrrolidine-1-carboxylate; (2R)-3-{[(2-fluoro-5-methylpyridin-3-yl)methyl]amino}-3-oxo-2-phenylpropyl pyrrolidine-1-carboxylate; (2R)-3-{[(2-fluoro-5-methylpyridin-3-yl)methyl]amino}-3-oxo-2-phenylpropyl dimethylcarbamate; 3-{[2-fluoro-5-(trifluoromethyl)benzyl]amino}-1-methyl-3-oxo-2-phenylpropylpyrrolidine-1-carboxylate; 3-{[2-fluoro-5-(trifluoromethyl)benzyl]amino}-2-hydroxy-3-oxo-2-phenylpropylpyrrolidine-1-carboxylate; and pharmaceutically acceptable salts and stereoisomers thereof.

In another embodiment the compound of formula I is chosen from (2R)-3,3,3-trifluoro-N-(2-fluoro-5-trifluoromethylbenzyl)-2-hydroxy-2-phenylpropanamide, (2R)-3-{[2-fluoro-5-(trifluoromethyl)benzyl]amino}-3-oxo-2-phenylpropyl pyrrolidine-1-carboxylate, and (2R)-2-cyclopropyl-N-((2-fluoro-5-methylpyridin-3-yl)methyl)-2-hydroxy-2-phenylacetamide and pharmaceutically acceptable salts and stereoisomers thereof. In a variant of this embodiment the compound in accordance with this invention is (2R)-3,3,3-trifluoro-N-(2-fluoro-5-trifluoromethylbenzyl)-2-hydroxy-2-phenylpropanamide and pharmaceutically acceptable salts and stereoisomers thereof. Another variant is the compound of formula I is (2R)-2-cyclopropyl-N-((2-fluoro-5-methylpyridin-3-yl)methyl)-2-hydroxy-2-phenylacetamide and pharmaceutically acceptable salts and stereoisomers thereof.

In one embodiment, the compounds of the present invention are chosen from (S)—N-(2-fluoro-5-(trifluoromethyl)benzyl)-2-phenylbutanamide; (S)—N-((2-fluoro-5-(trifluoromethyl)pyridin-3-yl)methyl)-2-phenylbutanamide; (S)—N-(5-bromo-2-fluorobenzyl)-2-phenylbutanamide; (S)—N-(5-ethyl-2-fluorobenzyl)-2-phenylbutanamide; (S)—N-((2-fluoro-5-methylpyridin-3-yl)methyl)-2-phenylbutanamide; (S)—N-((5-ethyl-2-fluoropyridin-3-yl)methyl)-2-phenylbutanamide; (S)—N-((5-cyclopropyl-2-fluoropyridin-3-yl)methyl)-2-phenylbutanamide; (2S)—N-[(5-cyclopropyl-2-fluoropyridin-3-yl)methyl]-2-(3,4-dichlorophenyl)butanamide; (2S)—N-[(5-ethyl-2-fluoropyridin-3-yl)methyl]-2-(3,4-dichlorophenyl)butanamide; (2S)—N-[(5-methyl-2-fluoropyridin-3-yl)methyl]-2-(3,4-dichlorophenyl)butanamide; (2S)—N-(2-fluoro-5-(trifluoromethyl)benzyl)-2-(3-bromophenyl)butanamide; (2S)—N-(5-bromo-2-fluorobenzyl)-2-(3-bromophenyl)butanamide; (2S)—N-(5-(cyclopropyl)-2-fluorobenzyl)-2-(3-bromophenyl)butanamide; (2S)—N-(5-chloro-2-fluorobenzyl)-2-(4-bromophenyl)butanamide; (2S)—N-(2-fluoro-5-(trifluoromethyl)benzyl)-2-(4-bromophenyl)butanamide; (2S)—N-(5-bromo-2-fluorobenzyl)-2-(4-bromophenyl)butanamide; (2S)—N-(5-(cyclopropyl)-2-fluorobenzyl)-2-(4-bromophenyl)butanamide; (2S)—N-(2-fluoro-5-(trifluoromethyl)benzyl)-2-hydroxy-2- phenylbutanamide; (2S)—N-(2-fluoro-5-(trifluoromethyl)benzyl)-2-(3-chlorophenyl)-2-hydroxybutanamide; (2S)—N-((2-fluoro-5-methylpyridin-3-yl)methyl)-2-hydroxy-2-phenylbutanamide; (2S)-2-cyclopropyl-N-((2-fluoro-5-methylpyridin-3-yl)methyl)-2-hydroxy-2-phenylacetamide; (2S)—N-((5-ethyl-2-fluoropyridin-3-yl)methyl)-2-hydroxy-2-phenylbutanamide; (2S)-3,3,4,4,4-pentafluoro-N-[(2-fluoro-5-methylpyridin-3-yl)methyl]-2-hydroxy-2-phenylbutanamide; (2S)-3,3,4,4,4-pentafluoro-N-(2-fluoro-5-cyclopropylbenzyl)-2-hydroxy-2-phenylbutanamide; (2S)-3,3,4,4,4-pentafluoro-N-(2-fluoro-5-trifluoromethylbenzyl)-2-hydroxy-2-phenylbutanamide; (2S)-2-(4-chloro-3-fluorophenyl)-3,3,3-trifluoro-[2-fluoro-5-(trifluoromethyl)benzyl]-2-hydroxypropanamide; (2S)-2-(4-chloro-3-fluorophenyl)-3,3,3-trifluoro-[2-fluoro-5-(trifluoromethyl)benzyl]-2-hydroxypropanamide; (2S)-3-{[2-fluoro-5-(trifluoromethyl)benzyl]amino}-3-oxo-2-phenylpropyl dimethylcarbamate; (2S)-3-{[2-fluoro-5-(trifluoromethyl)benzyl]amino}-3-oxo-2-phenylpropyl pyrrolidine-1-carboxylate; (2S)-3-{[(2-fluoro-5-methylpyridin-3-yl)methyl]amino}-3-oxo-2-phenylpropyl pyrrolidine-1-carboxylate; (2S)-3-{[(2-fluoro-5-methylpyridin-3-yl)methyl]amino}-3-oxo-2-phenylpropyl dimethylcarbamate; and pharmaceutically acceptable salts and stereoisomers thereof.

In another embodiment the compound of formula I is chosen from (2S)-3-{[2-fluoro-5-(trifluoromethyl)benzyl]amino}-3-oxo-2-phenylpropyl dimethylcarbamate, (2S)—N-[(5-methyl-2-fluoropyridin-3-yl)methyl]-2-(3,4-dichlorophenyl)butanamide, and (S)—N-((2-fluoro-5-(trifluoromethyl)pyridin-3-yl)methyl)-2-phenylbutanamide and pharmaceutically acceptable salts and stereoisomers thereof. In a variant of this embodiment the compound in accordance with this invention is (2S)—N-[(5-methyl-2-fluoropyridin-3-yl)methyl]-2-(3,4-dichlorophenyl)butanamide and pharmaceutically acceptable salts and stereoisomers thereof. Another variant is the compound of formula I is (S)—N-((2-fluoro-5-(trifluoromethyl)pyridin-3-yl)methyl)-2-phenylbutanamide and pharmaceutically acceptable salts and stereoisomers thereof.

Compounds of the present invention have been found to be tissue-selective modulators of the androgen receptor (SARMs). In one aspect, compounds of the present invention can be useful to activate the function of the androgen receptor in a mammal, and in particular to activate the function of the androgen receptor in bone and/or muscle tissue and block or inhibit ("antagonize") the function of the androgen receptor in the prostate of a male individual or in the uterus of a female individual.

A further aspect of the present invention is the use of compounds of formula I to attenuate or block the function of the androgen receptor in the prostate of a male individual or in the uterus of a female individual induced by AR agonists, but not in hair-growing skin or vocal cords, and activate the function of the androgen receptor in bone and/or muscle tissue, but not in organs which control blood lipid levels (e.g. liver).

Representative compounds of the present invention typically display submicromolar binding affinity for the androgen receptor. Compounds of this invention are therefore useful in treating mammals suffering from disorders related to androgen receptor function. Therapeutically effective amounts of the compound, including the pharmaceutically acceptable salts thereof, are administered to the mammal, to treat disorders related to androgen receptor function, such as, androgen deficiency, disorders which can be ameliorated by androgen replacement, or which can be improved by androgen replacement, including: enhancement of weakened muscle tone, osteoporosis, osteopenia, glucocorticoid-induced osteoporosis, periodontal disease, bone fracture (for example, vertebral and non-vertebral fractures), bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, pancreatic cancer, inflammatory arthritis and joint repair, HIV-wasting, prostate cancer, benign prostatic hyperplasia (BPH), cancer cachexia, Alzheimer's disease, muscular dystrophies, cognitive decline, sexual dysfunction, sleep apnea, depression, premature ovarian failure, and autoimmune disease. Treatment is effected by administration of a therapeutically effective amount of a compound of structural formula I to a mammal in need of such treatment. In addition, these compounds are useful as ingredients in pharmaceutical compositions alone or in combination with other active agents.

In one embodiment, the compounds of the present invention can be used to treat conditions in a male individual which are caused by androgen deficiency or which can be ameliorated by androgen replacement, including, but not limited to, osteoporosis, osteopenia, glucocorticoid-induced osteoporosis, periodontal disease, HIV-wasting, prostate cancer, cancer cachexia, obesity, arthritic conditions, anemias, such as for example, aplastic anemia, muscular dystrophies, and Alzheimer's disease, cognitive decline, sexual dysfunction, sleep apnea, depression, benign prostatic hyperplasia (BPH), abdominal obesity, metabolic syndrome, type II diabetes, and atherosclerosis, alone or in combination with other active agents. Treatment is effected by administration of a therapeutically effective amount of a compound of structural formula I to a male individual in need of such treatment.

"Arthritic condition" or "arthritic conditions" refers to a disease wherein inflammatory lesions are confined to the joints or any inflammatory conditions of the joints, most notably osteoarthritis and rheumatoid arthritis (Academic Press Dictionary of Science Technology; Academic Press; 1st edition, Jan. 15, 1992). The compounds of Formula I are also useful, alone or in combination, to treat or prevent arthritic conditions, such as Behcet's disease; bursitis and tendinitis; CPPD deposition disease; carpal tunnel syndrome; Ehlers-Danlos syndrome; fibromyalgia; gout; infectious arthritis; inflammatory bowel disease; juvenile arthritis; lupus erythematosus; lyme disease; marfan syndrome; myositis; osteoarthritis; osteogenesis imperfecta; osteonecrosis; polyarteritis; polymyalgia rheumatica; psoriatic arthritis; Raynaud's phenomenon; reflex sympathetic dystrophy syndrome; Reiter's syndrome; rheumatoid arthritis; scleroderma; and Sjogren's syndrome. An embodiment of the invention encompasses the treatment or prevention of an arthritic condition which comprises administering a therapeutically effective amount of a Compound of Formula I. A subembodiment is the treatment or prevention of osteoarthritis, which comprises administering a therapeutically effective amount of a Compound of Formula I. See: Cutolo M, Seriolo B, Villaggio B, Pizzorni C, Craviotto C, Sulli A. *Ann. N.Y. Acad. Sci.* 2002 June; 966: 131-42; Cutolo, *M. Rheum Dis Clin North Am* 2000 November;26(4):881-95; Bijlsma J W, Van den Brink H R. Am J Reprod Immunol 1992 October-December;28(3-4):231-4; Jansson L, Holmdahl R.; *Arthritis Rheum* 2001 September; 44(9):2168-75; and Purdie D W. Br *Med Bull* 2000; 56(3): 809-23. Also, see Merck Manual, 17th edition, pp. 449-451.

When used in combination to treat arthritic conditions, the compounds of Formula I can be used with any of the drugs disclosed herein as useful for combination therapy, or can be used with drugs known to treat or prevent arthritic conditions, such as corticosteroids, cytoxic drugs (or other disease modifying or remission inducing drugs), gold treatment, methotrexate, NSAIDs, and COX-2 inhibitors.

In another embodiment, the compounds of the present invention can be used to treat conditions in a female individual which are caused by androgen deficiency or which can be ameliorated by androgen replacement, including, but not limited to, osteoporosis, osteopenia, aging skin, glucocorticoid-induced osteoporosis, postmenopausal symptoms, periodontal disease, HIV-wasting, cancer cachexia, obesity, anemias, such as for example, aplastic anemia, muscular dystrophies, Alzheimer's disease, premature ovarian failure, cognitive decline, sexual dysfunction, depression, inflammatory arthritis and joint repair, atherosclerosis, and autoimmune disease, alone or in combination with other active agents. Treatment is effected by administration of a therapeutically effective amount of a compound of structural formula I to a female individual in need of such treatment.

The compounds of formula I are also useful in the enhancement of muscle tone in mammals, such as for example, humans. The compounds of structural formula I can also be employed as adjuncts to traditional androgen depletion therapy in the treatment of prostate cancer to restore bone, minimize bone loss, and maintain bone mineral density. In this manner, they can be employed together with traditional androgen deprivation therapy, including GnRH agonists/antagonists, such as those disclosed in P. Limonta, et al., *Exp. Opin. Invest. Drugs*, 10: 709-720 (2001); H. J. Stricker, *Urology*, 58 (Suppl. 2A): 24-27 (2001); R. P. Millar, et al., *British Medical Bulletin*, 56: 761-772 (2000); and A. V. Schally et al., *Advanced Drug Delivery Reviews*, 28: 157-169 (1997). The compounds of structural formula I can be used in combination with antiandrogens, such as flutamide, 2-hydroxyflutamide (the active metabolite of flutamide), nilutamide, and bicalutamide (Casodex™) in the treatment of prostate cancer.

Further, the compounds of the present invention can also be employed in the treatment of pancreatic cancer, either for their androgen antagonist properties or as an adjunct to an antiandrogen, such as flutamide, 2-hydroxyflutamide (the active metabolite of flutamide), nilutamide, and bicalutamide (Casodex™).

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

Compounds of structural formula I can minimize the negative effects on lipid metabolism. Therefore, considering their tissue selective androgen agonistic properties, the compounds of this invention exhibit advantages over existing approaches for hormone replacement therapy in hypogonadic (androgen deficient) male individuals.

Additionally, compounds of the present invention can increase the number of blood cells, such as red blood cells and platelets, and can be used for treatment of hematopoietic disorders, such as aplastic anemia.

In one embodiment of the invention, therapeutically effective amounts of the compound of Formula I, are administered to the mammal, to treat or improve disorders selected from enhancement of weakened muscle tone, osteoporosis, osteopenia, glucocorticoid-induced osteoporosis, periodontal disease, bone fracture, bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, pancreatic cancer, inflammatory arthritis and joint repair, HIV-wasting, prostate cancer, benign prostatic hyperplasia (BPH), cancer cachexia, Alzheimer's disease, muscular dystrophies, cognitive decline, sexual dysfunction, sleep apnea, depression, premature ovarian failure, and autoimmune disease.

In another embodiment, therapeutically effective amounts of the compound can be used to treat or improve a disorder selected from weakened muscle tone, osteoporosis, osteopenia, glucocorticoid-induced osteoporosis, periodontal disease, bone fracture, bone damage following bone reconstructive surgery, sarcopenia, Alzheimer's disease, and frailty.

In another embodiment, the compound in accordance with the invention can be used to treat or improve a disorder such as male hypogonadism, postmenopausal symptoms in women, atherosclerosis, hypercholesterolemia, hyperlipidemia, obesity, aplastic anemia and other hematopoietic disorders, pancreatic cancer, inflammatory arthritis and joint repair, HIV-wasting, prostate cancer, benign prostatic hyperplasia (BPH), cancer cachexia, muscular dystrophies, cognitive decline, sexual dysfunction, sleep apnea, depression, premature ovarian failure, and autoimmune disease.

The compounds of the present invention can be administered in their enantiomerically pure form. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

As used herein, a compound of the present invention which functions as an "agonist" of the androgen receptor can bind to the androgen receptor and initiate a physiological or a pharmacological response characteristic of that receptor. The term "tissue-selective androgen receptor modulator" refers to an androgen receptor ligand that mimics the action of a natural ligand in some tissues but not in others. A "partial agonist" is an agonist which is unable to induce maximal activation of the receptor population, regardless of the amount of compound applied. A "full agonist" induces full activation of the androgen receptor population at a given concentration. A compound of the present invention which functions as an "antagonist" of the androgen receptor can bind to the androgen receptor and block or inhibit the androgen-associated responses normally induced by a natural androgen receptor ligand.

The term "pharmaceutically acceptable salts" refers to salts prepared from pharmaceutically acceptable non-toxic bases or acids including inorganic or organic bases and inorganic or organic acids. Non-limiting representative salts derived from inorganic bases include aluminum, ammonium, calcium, copper, ferric, ferrous, lithium, magnesium, manganic salts, manganous, potassium, sodium, zinc, and the like. In one variant of the invention, the salts are chosen from the ammonium, calcium, lithium, magnesium, potassium, and sodium salts. Non-limiting examples of salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts can be prepared from pharmaceutically acceptable non-toxic acids, including inorganic and organic acids. Representative acids which can be employed include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. In one variant, the acids are selected from citric, fumaric, hydrobromic, hydrochloric, maleic, phosphoric, sulfuric, and tartaric acids.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It would also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The term "therapeutically effective amount" means the amount the compound of structural formula I that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts.

By "pharmaceutically acceptable" it is meant that the carrier, diluent or excipient must be compatible with the other ingredients of the formulation and not be deleterious to the recipient thereof.

The terms "administration of a compound" and "administering a compound" should be understood to mean providing a compound of the invention or a prodrug of a compound of the invention to the individual in need of treatment.

By the term "modulating a function mediated by the androgen receptor in a tissue selective manner" it is meant modulating a function mediated by the androgen receptor selectively (or discriminately) in anabolic (bone and/or muscular) tissue (bone and muscular) in the absence of such modulation at androgenic (reproductive) tissue, such as the prostate, testis, seminal vesicles, ovary, uterus, and other sex accessory tissues. In one embodiment, the function of the androgen receptor in anabolic tissue is activated whereas the function of the androgen receptor in androgenic tissue is blocked or suppressed. In another embodiment, the function of the androgen receptor in anabolic tissue is blocked or suppressed whereas the function of the androgen receptor in androgenic tissue is activated.

The administration of a compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient can concomitantly require, and other factors in the physician's judgment.

If formulated as a fixed dose, such combination products employ the compounds of this invention within the dosage range described below and the other pharmaceutically active agent(s) within its approved dosage range. Compounds of the instant invention can alternatively be used sequentially with known pharmaceutically acceptable agent(s) when a combination formulation is inappropriate.

Generally, the daily dosage of a compound of structural formula I can be varied over a wide range from about 0.01 to about 1000 mg per adult human per day. For example, dosages range from about 0.1 to about 200 mg/day. For oral administration, the compositions can be provided in the form of tablets containing from about 0.01 to about 1000 mg, such as for example, 0.01, 0.05, 0.1, 0.5, 1.0, 2.5, 3.0, 5.0, 6.0, 10.0, 15.0, 25.0, 50.0, 75, 100, 125, 150, 175, 180, 200, 225, and 500 milligrams of the active ingredient for the symptomatic adjustment of the dosage to the mammal to be treated.

The dose can be administered in a single daily dose or the total daily dosage can be administered in divided doses of two, three or four times daily. Furthermore, based on the properties of the individual compound selected for administration, the dose can be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through an intravenous solution, the dosage administration will, of course, be continuous rather than intermittent throughout the dosage regimen.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

Formulations of the tissue-selective androgen receptor modulator employed in the present method for medical use comprise a compound of structural formula I together with an acceptable carrier thereof and optionally other therapeutically active ingredients. The carrier must be pharmaceutically acceptable in the sense of being compatible with the other ingredients of the formulation and not being deleterious to the recipient subject of the formulation.

The present invention, therefore, further provides a pharmaceutical formulation comprising a compound of structural formula I together with a pharmaceutically acceptable carrier thereof. The formulations include those suitable for oral, rectal, intravaginal, intranasal, topical and parenteral (including subcutaneous, intramuscular and intravenous administration). In one embodiment, the formulations are those suitable for oral administration.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to about 5% by weight of the active compound in admixture with a pharmaceutically acceptable vehicle. Transdermal skin patches useful for administering the compounds of the present invention include those well known to those of ordinary skill in that art.

The formulations can be presented in a unit dosage form and can be prepared by any of the methods known in the art of pharmacy. All methods include the step of bringing the active compound in association with a carrier, which constitutes one or more ingredients. In general, the formulations are prepared by uniformly and intimately bringing the active compound in association with a liquid carrier, a waxy solid carrier or a finely divided solid carrier, and then, if needed, shaping the product into the desired dosage form.

Formulations of the present invention suitable for oral administration can be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, or an emulsion.

A tablet can be made by compression or molding, optionally with one or more accessory ingredients. Compressed tablets can be prepared by compressing in a suitable machine the active compound in a free flowing form, e.g., a powder or granules, optionally mixed with accessory ingredients, e.g., binders, lubricants, inert diluents, disintegrating agents or coloring agents. Molded tablets can be made by molding in a suitable machine a mixture of the active compound, preferably in powdered form, with a suitable carrier. Suitable binders include, without limitation, starch, gelatin, natural sugars such as glucose or beta-lactose, corn sweeteners, natural and synthetic gums such as acacia, tragacanth or sodium alginate, carboxymethyl-cellulose, polyethylene glycol, waxes and the like. Non-limiting representative lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral liquid forms, such as syrups or suspensions in suitably flavored suspending or dispersing agents such as the synthetic and natural gums, for example, tragacanth, acacia, methyl cellulose and the like, can be made by adding the active compound to the solution or suspension. Additional dispersing agents which can be employed include glycerin and the like.

Formulations for vaginal or rectal administration can be presented as a suppository with a conventional carrier, i.e., a base that is nontoxic and nonirritating to mucous membranes, compatible with a compound of structural formula I, and is stable in storage and does not bind or interfere with the release of the compound of structural formula I. Suitable bases include: cocoa butter (theobroma oil), polyethylene glycols (such as carbowax and polyglycols), glycol-surfactant combinations, polyoxyl 40 stearate, polyoxyethylene sorbitan fatty acid esters (such as Tween, Myrj, and Arlacel), glycerinated gelatin, and hydrogenated vegetable oils. When glycerinated gelatin suppositories are used, a preservative such as methylparaben or propylparaben can be employed.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention can also be delivered by the use of monoclonal antibodies as individual carriers to which the compound molecules are coupled. The compounds of the present invention can also be coupled with soluble polymers as targetable drug carriers. Such polymers can include polyvinyl-pyrrolidone, pyran copolymer, polyhydroxypropylmethacrylamide-phenol, polyhydroxy-ethylaspartamidephenol, or polyethylene-oxide polylysine substituted with palmitoyl residues. Furthermore, the compounds of the present invention can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Formulations suitable for parenteral administration include formulations that comprise a sterile aqueous preparation of the active compound which can be isotonic with the blood of the recipient. Such formulations suitably comprise a solution or suspension of a compound that is isotonic with the blood of the recipient subject. Such formulations can contain distilled water, 5% dextrose in distilled water or saline and the active compound. Often it is useful to employ a pharmaceutically and pharmacologically acceptable acid addition salt of the active compound that has appropriate solubility for the solvents employed. Useful formulations also comprise concentrated solutions or solids comprising the active compound which on dilution with an appropriate solvent give a solution suitable for parenteral administration.

The pharmaceutical composition and method of the present invention can further comprise other therapeutically active compounds usually applied in the treatment of the above mentioned conditions, including osteoporosis, periodontal disease, bone fracture, bone damage following bone reconstructive surgery, sarcopenia, frailty, aging skin, male hypogonadism, post-menopausal symptoms in women, atherosclerosis, hypercholesterolemia, hyperlipidemia, hematopoietic disorders, such as for example, aplastic anemia, pancreatic cancer, Alzheimer's disease, inflammatory arthritis, and joint repair.

For the treatment and prevention of osteoporosis, the compounds of the present invention can be administered in combination with at least one bone-strengthening agent selected from antiresorptive agents, osteoanabolic agents, and other agents beneficial for the skeleton through mechanisms which are not precisely defined, such as calcium supplements, flavonoids, and vitamin D analogs. The conditions of periodontal disease, bone fracture, and bone damage following bone reconstructive surgery can also benefit from these combined treatments. For example, the compounds of the instant invention can be effectively administered in combination with effective amounts of other agents such as estrogens, bisphosphonates, SERMs, cathepsin K inhibitors, $\alpha v \beta 3$ integrin receptor antagonists, vacuolar ATPase inhibitors, the polypeptide osteoprotegerin, antagonists of VEGF, thiazolidinediones, calcitonin, protein kinase inhibitors, parathyroid hormone (PTH) and analogs, calcium receptor antagonists, growth hormone secretagogues, growth hormone releasing hormone, insulin-like growth factor, bone morphogenetic protein (BMP), inhibitors of BMP antagonism, prostaglandin derivatives, fibroblast growth factors, vitamin D and derivatives thereof, vitamin K and derivatives thereof, soy isoflavones, calcium salts, and fluoride salts. The conditions of periodontal disease, bone fracture, and bone damage following bone reconstructive surgery can also benefit from these combined treatments.

In one embodiment of the present invention, a compound of the instant invention can be effectively administered in combination with an effective amount of at least one bone-strengthening agent chosen from estrogen, and estrogen derivatives, alone or in combination with progestin or progestin derivatives; bisphosphonates; antiestrogens or selective estrogen receptor modulators; αvβ3 integrin receptor antagonists; cathepsin K inhibitors; osteoclast vacuolar ATPase inhibitors; calcitonin; and osteoprotegerin.

In the treatment of osteoporosis, the activity of the compounds of the present invention are distinct from that of the anti-resorptive agents: estrogens, bisphosphonates, SERMs, calcitonin, cathepsin K inhibitors, vacuolar ATPase inhibitors, agents interfering with the RANK/RANKL/Osteoprotegerin pathway, p38 inhibitors or any other inhibitors of osteoclast generation or osteoclast activation. Rather than inhibiting bone resorption, the compounds of structural formula I aid in the stimulation of bone formation, acting, for example, on cortical bone, which is responsible for a significant part of bone strength. The thickening of cortical bone substantially contributes to a reduction in fracture risk, especially fractures of the hip. The combination of the tissue-SARMs of structural formula I with anti-resorptive agents such as for example estrogen or estrogen derivatives, bisphonates, antiestrogens, SERMs, calcitonin, αvβ3 integrin receptor antagonists, HMG-CoA reductase inhibitors, vacuolar ATPase inhibitors, and cathepsin K inhibitors is particularly useful due to the complementary effect of the bone anabolic and antiresorptive actions.

Non-limiting representatives of estrogen and estrogen derivatives include steroidal compounds having estrogenic activity such as, for example, 17β-estradiol, estrone, conjugated estrogen (PREMARIN®), equine estrogen, 17β-ethynyl estradiol, and the like. The estrogen or estrogen derivative can be employed alone or in combination with a progestin or progestin derivative. Nonlimiting examples of progestin derivatives are norethindrone and medroxy-progesterone acetate.

Non-limiting examples of bisphosphonate compounds which can also be employed in combination with a compound of the present invention include:

(a) alendronate (also known as alendronic acid, 4-amino-1-hydroxybutylidene-1,1-bisphosphonic acid, alendronate sodium, alendronate monosodium trihydrate or 4-amino-1-hydroxybutylidene-1,1-bisphosphonic acid monosodium trihydrate. Alendronate is described in U.S. Pat. Nos. 4,922,007, to Kieczykowski et al., issued May 1, 1990; 5,019,651, to Kieczykowski, issued May 28, 1991; 5,510,517, to Dauer et al., issued Apr. 23, 1996; 5,648,491, to Dauer et al., issued Jul. 15, 1997;

(b) [(cycloheptylamino)-methylene]-bis-phosphonate (incadronate), which is described in U.S. Pat. No. 4,970,335, to Isomura et al., issued Nov. 13, 1990;

(c) (dichloromethylene)-bis-phosphonic acid (clodronic acid) and the disodium salt (clodronate), which are described in Belgium Patent 672,205 (1966) and *J. Org. Chem.* 32, 4111 (1967);

(d) [1-hydroxy-3-(1-pyrrolidinyl)-propylidene]-bis-phosphonate (EB-1053);

(e) (1-hydroxyethylidene)-bis-phosphonate (etidronate);

(f) [1-hydroxy-3-(methylpentylamino)propylidene]-bis-phosphonate (ibandronate), which is described in U.S. Pat. No. 4,927,814, issued May 22, 1990;

(g) (6-amino-1-hydroxyhexylidene)-bis-phosphonate (neridronate);

(h) [3-(dimethylamino)-1-hydroxypropylidene]-bis-phosphonate (olpadronate);

(i) (3-amino-1-hydroxypropylidene)-bis-phosphonate (pamidronate);

(j) [2-(2-pyridinyl)ethylidene]-bis-phosphonate (piridronate), which is described in U.S. Pat. No. 4,761,406;

(k) [1-hydroxy-2-(3-pyridinyl)-ethylidene]-bis-phosphonate (risedronate);

(l) {[(4-chlorophenyl)thio]methylene}-bis-phosphonate (tiludronate), which is described in U.S. Pat. No. 4,876,248, to Breliere et al., Oct. 24, 1989;

(m) [1-hydroxy-2-(1H-imidazol-1-yl)ethylidene]-bis-phosphonate (zoledronate); and (n) [1-hydroxy-2-imidazopyridin-(1,2-a)-3-ylethylidene]-bis-phosphonate (minodronate).

In one embodiment of the methods and compositions of the present invention, the bisphosphonate is chosen from alendronate, clodronate, etidronate, ibandronate, incadronate, minodronate, neridronate, olpadronate, pamidronate, piridronate, risedronate, tiludronate, zoledronate, pharmaceutically acceptable salts of these bisphosphonates, and mixtures thereof. In one variant, the bisphosphonate is selected from alendronate, risedronate, zoledronate, ibandronate, tiludronate, and clodronate. In a subclass of this class, the bisphosphonate is alendronate, pharmaceutically acceptable salts and hydrates thereof, and mixtures thereof. A particular pharmaceutically acceptable salt of alendronate is alendronate monosodium. Pharmaceutically acceptable hydrates of alendronate monosodium include the monohydrate and the trihydrate. A particular pharmaceutically acceptable salt of risedronate is risedronate monosodium. Pharmaceutically acceptable hydrates of risedronate monosodium include the hemi-pentahydrate.

Still further, antiestrogenic compounds such as raloxifene (see, e.g., U.S. Pat. No. 5,393,763), clomiphene, zuclomiphene, enclomiphene, nafoxidene, CI-680, CI-628, CN-55, 945-27, Mer-25, U-11,555A, U-100A, and salts thereof, and the like (see, e.g., U.S. Pat. Nos. 4,729,999 and 4,894,373) can be employed in combination with a compound of structural formula I in the methods and compositions of the present invention. These agents are also known as SERMs, or selective estrogen receptor modulators, agents known in the art to prevent bone loss by inhibiting bone resorption via pathways believed to be similar to those of estrogens.

Non-limiting representatives of SERMs include, for example, tamoxifen, raloxifene, lasofoxifene, toremifene, azorxifene, EM-800, EM-652, TSE 424, clomiphene, droloxifene, idoxifene, and levormeloxifene [Goldstein, et al., "A pharmacological review of selective estrogen receptor modulators," *Human Reproduction Update*, 6: 212-224 (2000); Lufiin, et al., *Rheumatic Disease Clinics of North America*, 27: 163-185 (2001), and "Targeting the Estrogen Receptor with SERMs," *Ann. Rep. Med. Chem.* 36:149-158 (2001)].

αvβ3 Integrin receptor antagonists suppress bone resorption and can be employed in combination with the SARMs of structural formula I for the treatment of bone disorders including osteoporosis. Peptidyl as well as peptidomimetic antagonists of the αvβ3 integrin receptor have been described both in the scientific and patent literature. For example, reference is made to W. J. Hoekstra and B. L. Poulter, *Curr. Med. Chem.* 5: 195-204 (1998) and references cited therein; WO 95/32710; WO 95/37655; WO 97/01540; WO 97/37655; WO 98/08840; WO 98/18460; WO 98/18461; WO 98/25892; WO 98/31359; WO 98/30542; WO 99/15506; WO 99/15507; WO 00/03973; EP 853084; EP 854140; EP 854145; U.S. Pat. Nos. 5,204,350; 5,217,994; 5,639,754; 5,741,796; 5,780,426; 5,929,120; 5,952,341; 6,017,925; and 6,048,861.

Other αvβ3 antagonists are described in R. M. Keenan et al., *J. Med. Chem.* 40: 2289-2292 (1997); R. M. Keenan et al.,

*Bioorg. Med. Chem. Lett.* 8: 3165-3170 (1998); and R. M. Keenan et al., *Bioorg. Med. Chem. Lett.* 8: 3171-3176 (1998).

Other non-limiting representative examples of published patent and patent applications that describe various αvβ3 integrin receptor antagonists include: those comprising benzazepine, benzodiazepine and benzocycloheptene—PCT Patent Application Nos. WO 96/00574, WO 96/00730, WO 96/06087, WO 96/26190, WO 97/24119, WO 97/24122, WO 97/24124, WO 98/14192, WO 98/15278, WO 99/05107, WO 99/06049, WO 99/15170, WO 99/15178, WO 97/34865, WO 99/15506, and U.S. Pat. No. 6,159,964; those comprising dibenzpcycloheptene, and dibenzoxapine—PCT Patent Application Nos. WO 97/01540, WO 98/30542, WO 99/11626, WO 99/15508, and U.S. Pat. Nos. 6,008,213 and 6,069,158; those having a phenol constraint—PCT Patent Application Nos. WO 98/00395, WO 99/32457, WO 99/37621, WO 99/44994, WO 99/45927, WO 99/52872, WO 99/52879, WO 99/52896, WO 00/06169, European Patent Nos. EP 0 820,988, EP 0 820,991, and U.S. Pat. Nos. 5,741, 796, 5,773,644, 5,773,646, 5,843,906, 5,852,210, 5,929,120, 5,952,281, 6,028,223 and 6,040,311; those having a monocyclic ring constraint—PCT Patent Application Nos. WO 99/26945, WO 99/30709, WO 99/30713, WO 99/31099, WO 99/59992, WO 00/00486, WO 00/09503, European Patent Nos. EP 0 796,855, EP 0 928,790, EP 0 928,793, and U.S. Pat. Nos. 5,710,159, 5,723,480, 5,981,546, 6,017,926, and 6,066, 648; and those having a bicyclic ring constraint—PCT Patent Application Nos. WO 98/23608, WO 98/35949, and WO 99/33798, European Patent No. EP 0 853,084, and U.S. Pat. Nos. 5,760,028, 5,919,792, and 5,925,655.

Cathepsin K, formerly known as cathepsin O2, is a cysteine protease and is described in PCT International Application Publication No. WO 96/13523; U.S. Pat. Nos. 5,501,969 and 5,736,357. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis. Non-limiting examples of cathespin K inhibitors can be found in PCT International Publications WO 01/49288 and WO 01/77073.

Members of the class of HMG-CoA reductase inhibitors, known as the "statins," have been found to trigger the growth of new bone, replacing bone mass lost as a result of osteoporosis (see *The Wall Street Journal*, Friday, Dec. 3, 1999, page B1). Therefore, the statins hold promise for the treatment of bone resorption. Examples of HMG-CoA reductase inhibitors include statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444, 784); dihydroxy open-acid simvastatin, particularly the ammonium or calcium salts thereof; pravastatin, particularly the sodium salt thereof (see U.S. Pat. No. 4,346,227); fluvastatin, particularly the sodium salt thereof (see U.S. Pat. No. 5,354,772); atorvastatin, particularly the calcium salt thereof (see U.S. Pat. No. 5,273,995); cerivastatin, particularly the sodium salt thereof (see U.S. Pat. No. 5,177,080), rosuvastatin, also known as ZD-4522 (see U.S. Pat. No. 5,260,440) and pitavastatin, also referred to as NK-104, itavastatin, or nisvastatin (see PCT international application publication number WO 97/23200).

Osteoclast vacuolar ATPase inhibitors, also called proton pump inhibitors, can be employed together with the SARMs of structural formula I. The proton ATPase which is found on the apical membrane of the osteoclast has been reported to play a significant role in the bone resorption process. Therefore, this proton pump represents an attractive target for the design of inhibitors of bone resorption which are potentially useful for the treatment and prevention of osteoporosis and related metabolic diseases [see C. Farina et al., *DDT,* 4: 163-172 (1999)].

The angiogenic factor VEGF has been shown to stimulate the bone-resorbing activity of isolated mature rabbit osteoclasts via binding to its receptors on osteoclasts [see M. Nakagawa et al., *FEBS Letters,* 473: 161-164 (2000)]. Therefore, the development of antagonists of VEGF binding to osteoclast receptors, such as KDR/Flk-1 and Flt-1, can provide yet a further approach to the treatment or prevention of bone resorption.

Activators of the peroxisome proliferator-activated receptor-γ(PPARγ), such as the thiazolidinediones (TZD's), inhibit osteoclast-like cell formation and bone resorption in vitro. Results reported by R. Okazaki et al. in *Endocrinology,* 140: 5060-5065 (1999) point to a local mechanism on bone marrow cells as well as a systemic one on glucose metabolism. Nonlimiting examples of PPARγ, activators include the glitazones, such as troglitazone, pioglitazone, rosiglitazone, and BRL 49653.

Calcitonin can also be employed together with the SARMs of structural formula I. Calcitonin is preferentially employed as salmon nasal spray (Azra et al., *Calcitonin.* 1996. In: J. P. Bilezikian, et al., Ed., *Principles of Bone Biology*, San Diego: Academic Press; and Silverman, "Calcitonin," *Rheumatic Disease Clinics of North America,* 27: 187-196, 2001)

Protein kinase inhibitors can also be employed together with the SARMs of structural formula I. Kinase inhibitors include those disclosed in WO 01/17562 and are in one embodiment selected from inhibitors of p38. Non-limiting examples of p38 inhibitors useful in the present invention include SB 203580 [Badger et al., *J. Pharmacol. Exp. Ther.,* 279: 1453-1461 (1996)].

Osteoanabolic agents are those agents that are known to build bone by increasing the production of the bone protein matrix. Such osteoanabolic agents include, for example, parathyroid hormone (PTH) and fragments thereof, such as naturally occurring PTH (1-84), PTH (1-34), analogs thereof, native or with substitutions and particularly parathyroid hormone subcutaneous injection. PTH has been found to increase the activity of osteoblasts, the cells that form bone, thereby promoting the synthesis of new bone (*Modern Drug Discovery*, Vol. 3, No. 8, 2000). An injectable recombinant form of human PTH, Forteo (teriparatide), has received regulatory approval in the U.S. for the treatment of osteoporosis.

Also useful in combination with the SARMs of the present invention are calcium receptor antagonists which induce the secretion of PTH as described by Gowen et al., *J. Clin. Invest.* 105: 1595-604 (2000).

Additional osteoanabolic agents include growth hormone secretagogues, growth hormone, growth hormone releasing hormone and the like can be employed with the compounds according to structural formula I for the treatment of osteoporosis. Representative growth hormone secretagogues are disclosed in U.S. Pat. Nos. 3,239,345, 4,036,979, 4,411, 890, 5,206,235, 5,283,241, 5,284,841, 5,310,737, 5,317,017, 5,374,721, 5,430,144, 5,434,261, 5,438,136, 5,494,919, 5,494,920, 5,492,916 and 5,536,716; European Patent Pub. Nos. 0,144,230 and 0,513,974; PCT Patent Pub. Nos. WO 94/07486, WO 94/08508, WO 94/11012; WO 94/13696, WO 94/19367, WO 95/03289, WO 95/03290, WO 95/09633, WO 95/11029, WO 95/12598, WO 95/13069, WO 95/14666, WO 95/16675, WO 95/16692, WO 95/17422, WO 95/17423, WO 95/34311, and WO 96/02530; articles, *Science*, 260, 1640-1643 (Jun. 11, 1993); *Ann. Rep. Med. Chem.*, 28: 177-186 (1993); *Bioorg. Med. Chem. Lett.*, 4: 2709-2714 (1994); and *Proc. Natl. Acad. Sci. USA*, 92: 7001-7005 (1995).

Insulin-like growth factor (IGF) can also be employed together with the SARMs of structural formula I. Insulin-like growth factors can be selected from Insulin-like Growth Factor I, alone or in combination with IGF binding protein 3 and IGF II [See Johannson and Rosen, "The IGFs as potential therapy for metabolic bone diseases," 1996, In: Bilezikian, et al., Ed., *Principles of Bone Biology*, San Diego: Academic Press; and Ghiron et al., *J. Bone Miner. Res.* 10: 1844-1852 (1995)].

Bone morphogenetic protein (BMP) can also be employed together with the SARMs of structural formula I. Bone morphogenetic protein includes BMP 2, 3, 5, 6, 7, as well as related molecules TGF beta and GDF 5 [Rosen et al., "Bone morphogenetic proteins," 1996. In: J. P. Bilezikian, et al., Ed., *Principles of Bone Biology*, San Diego: Academic Press; and Wang E A, *Trends Biotechnol.*, 11: 379-383 (1993)].

Inhibitors of BMP antagonism can also be employed together with the SARMs of structural formula I. In one embodiment, BMP antagonist inhibitors are chosen from inhibitors of the BMP antagonists SOST, noggin, chordin, gremlin, and dan [see Massague and Chen, "Controlling TGF-beta signaling,"*Genes Dev.*, 14: 627-644, 2000; Aspenberg et al., *J. Bone Miner. Res.* 16: 497-500, 2001; and Brunkow et al., *Am. J. Hum. Genet.* 68: 577-89 (2001)].

The tissue-selective androgen receptor modulators of the present invention can also be combined with the polypeptide osteoprotegerin for the treatment of conditions associated with bone loss, such as osteoporosis. The osteoprotegerin can be selected from mammalian osteoprotegerin and human osteoprotegerin. The polypeptide osteoprotegerin, a member of the tumor necrosis factor receptor super-family, is useful to treat bone diseases characterized by increased bone loss, such as osteoporosis. Reference is made to U.S. Pat. No. 6,288, 032.

Prostaglandin derivatives can also be employed together with the SARMs of structural formula I. Non-limiting representatives of prostaglandin derivatives are selected from agonists of prostaglandin receptors EP1, EP2, EP4, FP, IP and derivatives thereof [Pilbeam et al., "Prostaglandins and bone metabolism," 1996. In: Bilezikian, et al. Ed. Principles of Bone Biology, San Diego: Academic Press; Weinreb et al., *Bone*, 28: 275-281 (2001)].

Fibroblast growth factors can also be employed together with the SARMs of structural formula I. Fibroblast growth factors include aFGF, bFGF and related peptides with FGF activity [Hurley Florkiewicz, "Fibroblast growth factor and vascular endothelial growth factor families," 1996. In: J. P. Bilezikian, et al., Ed. Principles of Bone Biology, San Diego: Academic Press].

In addition to bone resorption inhibitors and osteoanabolic agents, there are also other agents known to be beneficial for the skeleton through mechanisms which are not precisely defined. These agents can also be favorably combined with the SARMs of structural formula I.

Vitamin D, vitamin D derivatives and analogs can also be employed together with the SARMs of structural formula I. Vitamin D and vitamin D derivatives include, for example, $D_3$ (cholecaciferol), $D_2$ (ergocalciferol), 25-OH-vitamin $D_3$, $1\alpha,25(OH)_2$ vitamin $D_3$, $1\alpha$-OH-vitamin $D_3$, $1\alpha$-OH-vitamin $D_2$, dihydrotachysterol, 26,27-F6-$1\alpha,25(OH)_2$ vitamin $D_3$, 19-nor-$1\alpha,25(OH)_2$ vitamin $D_3$, 22-oxacalcitriol, calcipotriol, $1\alpha,25(OH)_2$-16-ene-23-yne-vitamin $D_3$ (Ro 23-7553), EB1089, 20-epi-$1\alpha,25(OH)_2$ vitamin $D_3$, KH1060, ED71, $1\alpha,24(S)$-$OH)_2$ vitamin $D_3$, $1\alpha,24(R)$-$(OH)_2$ vitamin $D_3$ [See, Jones G., "Pharmacological mechanisms of therapeutics: vitamin D and analogs," 1996. In: J. P. Bilezikian, et al. Ed. Principles of Bone Biology, San Diego: Academic Press].

Vitamin K and Vitamin K derivatives can also be employed together with the SARMs of structural formula I. Vitamin K and vitamin K derivatives include menatetrenone (Vitamin K2) [see Shiraki et al., *J. Bone Miner. Res.*, 15: 515-521 (2000)].

Soy isoflavones, including ipriflavone, can be employed together with the SARMs of structural formula I.

Fluoride salts, including sodium fluoride (NaF) and monosodium fluorophosphate (MFP), can also be employed together with the SARMs of structural formula I. Dietary calcium supplements can also be employed together with the SARMs of structural formula I. Dietary calcium supplements include calcium carbonate, calcium citrate, and natural calcium salts (Heaney. Calcium. 1996. In: J. P. Bilezikian, et al., Ed., Principles of Bone Biology, San Diego: Academic Press).

Daily dosage ranges for bone resorption inhibitors, osteoanabolic agents and other agents which can be used to benefit the skeleton when used in combination with a compound of structural formula I are those which are known in the art. In such combinations, generally the daily dosage range for the SARMs of structural formula I ranges from about 0.01 to about 1000 mg per adult human per day, such as for example, from about 0.1 to about 200 mg/day. However, adjustments to decrease the dose of each agent can be made due to the increased efficacy of the combined agent.

In particular, when a bisphosphonate is employed, dosages from about 2.5 to about 100 mg/day (measured as the free bisphosphonic acid) are appropriate for treatment, such as for example ranging from 5 to 20 mg/day, or about 10 mg/day. Prophylactically, doses of about 2.5 to about 10 mg/day and especially about 5 mg/day should be employed. For reduction in side-effects, it can be desirable to administer the combination of a compound of structural formula I and the bisphosphonate once a week. For once weekly administration, doses ranging from about 15 mg to about 700 mg per week of bisphosphonate and from about 0.07 to about 7000 mg of a compound of structural formula I can be employed, either separately, or in a combined dosage form. A compound of structural formula I can be favorably administered in a controlled-release delivery device, particularly for once weekly administration.

For the treatment of atherosclerosis, hypercholesterolemia, and hyperlipidemia, the compounds of structural formula I can be effectively administered in combination with one or more additional active agents. The additional active agent or agents can be chosen from lipid-altering compounds such as HMG-CoA reductase inhibitors, agents having other pharmaceutical activities, and agents that have both lipid-altering effects and other pharmaceutical activities. Non-limiting examples of HMG-CoA reductase inhibitors include statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444,784); dihydroxy open-acid simvastatin, particularly the ammonium or calcium salts thereof; pravastatin, particularly the sodium salt thereof (see U.S. Pat. No. 4,346,227); fluvastatin, particularly the sodium salt thereof (see U.S. Pat. No. 5,354,772); atorvastatin, particularly the calcium salt thereof (see U.S. Pat. No. 5,273, 995); cerivastatin, particularly the sodium salt thereof (see U.S. Pat. No. 5,177,080), and nisvastatin, also referred to as NK-104 (see PCT international application publication number WO 97/23200).

Additional active agents which can be employed in combination with a compound of structural formula I include, but are not limited to, HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; cholesterol absorption inhibitors, such as SCH-58235, also known as ezetimibe and 1-(4-fluorophenyl)-3(R)-[3(S)-(4-fluorophenyl)-3-hydroxypropyl)]-4(S)-(4-hydroxyphenyl)-2-azetidinone, which is described in U.S. Pat. Nos. 5,767,115 and 5,846,966; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ), agonists, including the compounds commonly referred to as glitazones, for example troglitazone, pioglitazone and rosiglitazone and, including those compounds included within the structural class known as thiazolidinediones as well as those PPARγ, agonists outside the thiazolidinedione structural class; PPARα agonists, such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors, such as enalapril and captopril; calcium channel blockers, such as nifedipine and diltiazem; endothelin antagonists; agents such as LXR ligands that enhance ABC1 gene expression; bisphosphonate compounds, such as alendronate sodium; and cyclooxygenase-2 inhibitors, such as rofecoxib and celecoxib, as well as other agents known to be useful in the treatment of these conditions.

Daily dosage ranges for HMG-CoA reductase inhibitors when used in combination with the compounds of structural formula I correspond to those which are known in the art. Similarly, daily dosage ranges for the HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; cholesterol absorption inhibitors including ezetimibe; bile acid sequestrants; LDL (low density lipoprotein) receptor inducers; platelet aggregation inhibitors, including glycoprotein IIb/IIIa fibrinogen receptor antagonists and aspirin; human peroxisome proliferator activated receptor gamma (PPARγ) agonists; PPARα agonists; PPAR dual α/γ agonists; vitamin $B_6$; vitamin $B_{12}$; folic acid; anti-oxidant vitamins; beta-blockers; angiotensin II antagonists; angiotensin converting enzyme inhibitors; calcium channel blockers; endothelin antagonists; agents such as LXR ligands that enhance ABC1 gene expression; bisphosphonate compounds; and cyclooxygenase-2 inhibitors also correspond to those which are known in the art, although due to the combined action with the compounds of structural formula I, the dosage can be somewhat lower when administered in combination.

One embodiment of the invention is a method for affecting a bone turnover marker in a mammal comprising administering a therapeutically effective amount of a compound according to formula I. Non-limiting examples of bone turnover markers can be selected from urinary C-telopeptide degradation products of type I collagen (CTX), urinary N-telopeptide cross-links of type I collagen (NTX), osteocalcin (bone Gla protein), dual energy x-ray absorptionmetry (DXA), bone specific alkaline phosphatase (BSAP), quantitative ultrasound (QUS), and deoxypyridinoline (DPD) crosslinks.

In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating diseases caused by androgen deficiency or that can be ameliorated by addition of androgen.

| Abbreviations Used in the Description of the Preparation of the Compounds of the Present Invention: | |
|---|---|
| AcOH | Acetic acid |
| Dess-Martin | Dess Martin periodinane |
| DHT | Dihydrotestosterone |
| DIPEA | diisopropylethylamine |
| DMAP | 4-Dimethylaminopyridine |
| DMEM | Dulbecceo modified eagle media |
| DMSO | Dimethylsulfoxide |
| DMF | N,N-Dimethylformamide |
| EA | Ethyl acetate |
| EDC | 1-(3-Dimethylaminopropyl)3-ethylcarbodiimide HCl |
| EDTA | Ethylenediaminetetraacetic acid |
| EtOH | Ethanol |
| $Et_3B$ | triethylborane |
| $Et_3N$ | Triethylamine |
| FCS | Fetal calf serum |
| h | hour |
| HEPES | (2-Hydroxyethyl)-1-piperazineethanesulfonic acid |
| HOAt or HOAT | 1-hydroxy-7-azabenzotriazole |
| HPLC | High-performance liquid chromatography |
| KHMDS | Potassium bistrimethylsilylamide |
| LC/MS | Liquid chromotography/mass spectroscopy |
| LDA | Lithium diisopropylamide |
| LG | Leaving group |
| MeOH | Methanol |
| NBS | N-bromosuccinimide |
| n-Bu4NI | Tetra-n-butylammonium iodide |
| $Pd(PPh_3)_4$ | Tetrakis(triphenyl phosphine) palladium(0) |
| PMBCL | p-Methoxybenzyl chloride |
| p-TosCl | p-Toluenesulfonyl chloride |
| PyBop | benzotriazol-1-yloxytripyrrolidinophosphonium hexafluorophosphate |
| Rt or rt | Room temperature |
| $^tBuSONH_2$ | t-butylsulfinamide |
| TFA | Trifluoroacetic acid |
| TLC | Thin-layer chromatography |

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

Schemes A-F provides general guidelines for making compounds of Formula I. Scheme A shows the preparations of the amides starting from the commercially available 2-phenylbutanoic chloride or (2S)-phenylbutanoic acid. Scheme B indicates the synthetic routes to functionalize 3-position and to introduce various 5-alkyl groups to the 2-pyridine moiety starting from the commercially available 5-bromo-2-fluoropyridine (B-1). Scheme C is the synthetic routes to construct 2-fluoropyridine portion with various $R_4$ starting from the commercially available 5-substituted-2aminopyridines (C-1). Scheme D shows the synthetic methodology for introducing the difluoromethylene groups at the 5-position of the benzylamine moiety. Chemical transformations shown in Scheme E highlight the preparation of 2-alkyl-2-hydroxyphenylacetic acids (E-3) starting from the commercially available benzoylformic acids (E-1). Scheme F shows two different synthetic routes to synthesize the 2-hydroxy-2-perfluoroalkyl-2-arylacetic acid (F-5) either from F-1 or F-3. Scheme G, indicates that $R_3$, which can be chosen from halides or any group that can be introduced by the cross-coupling reactions, can be added to the benzylamine portion (G-1). Scheme H highlights the synthetic pathways to introduce the aminoacyloxymethyl group at 2-position of the phenylacetic acid moiety starting from the commercially available tropic acid (H-1).

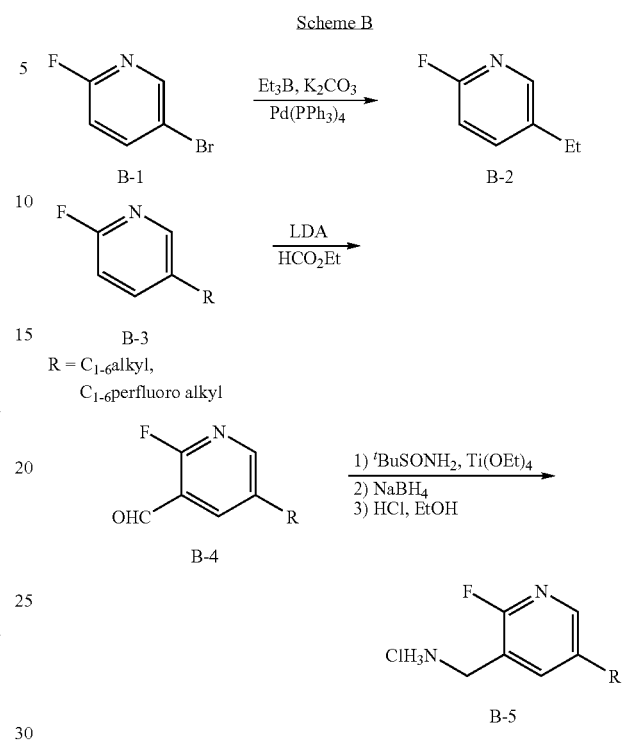

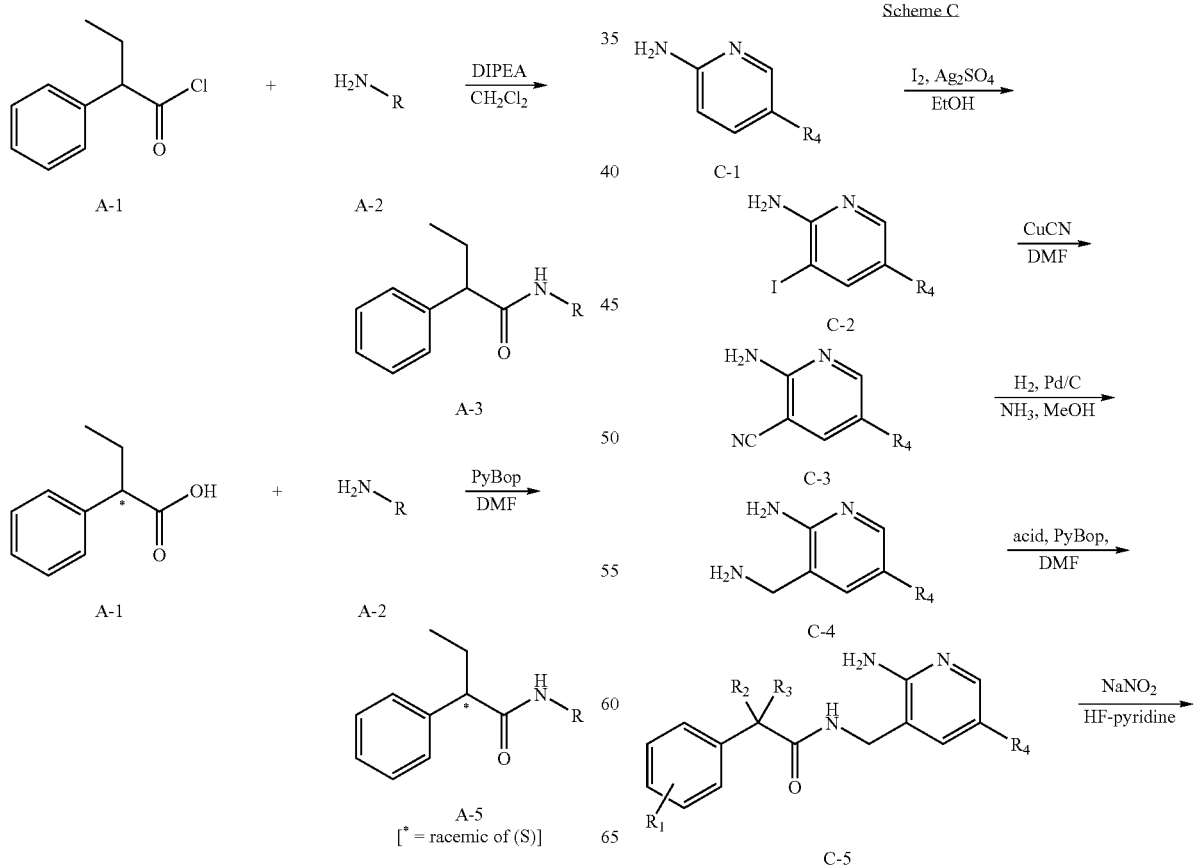

-continued
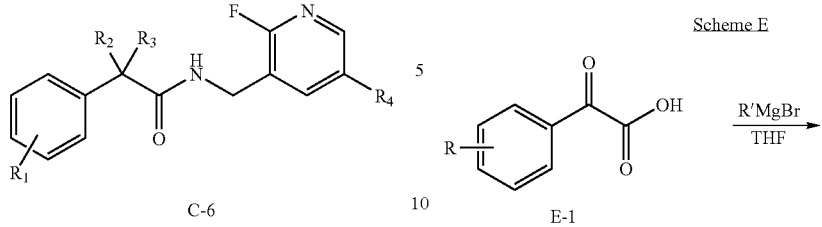
C-6
Scheme D
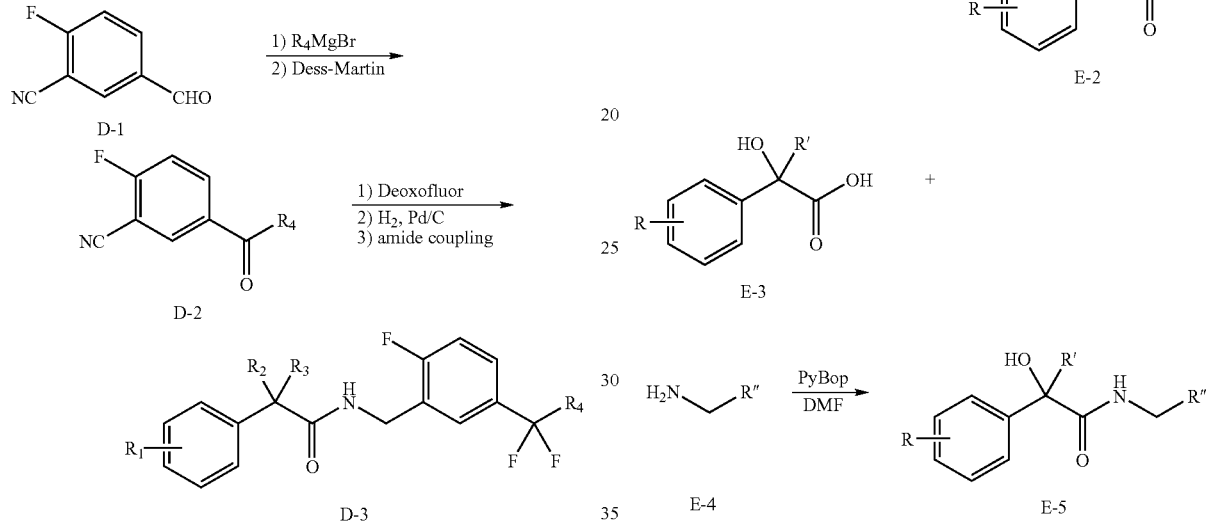
Scheme E
Scheme F
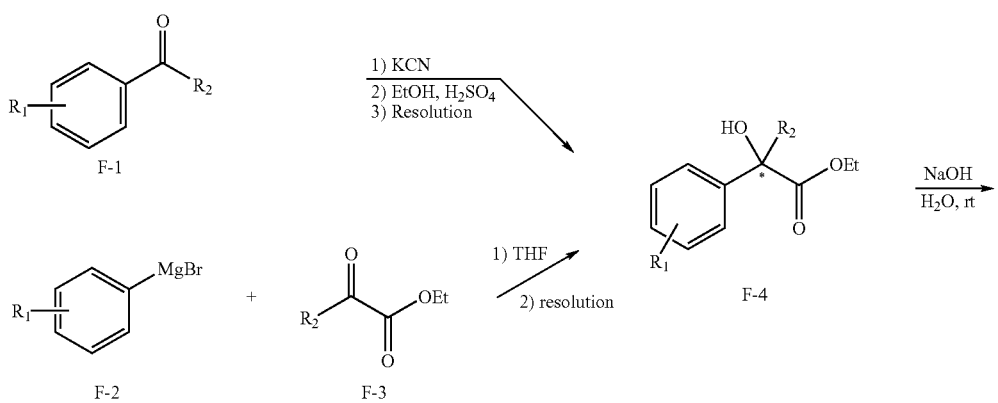
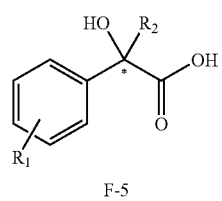
F-5

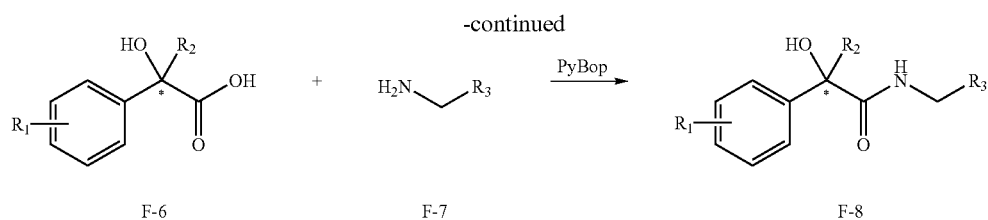
Scheme G
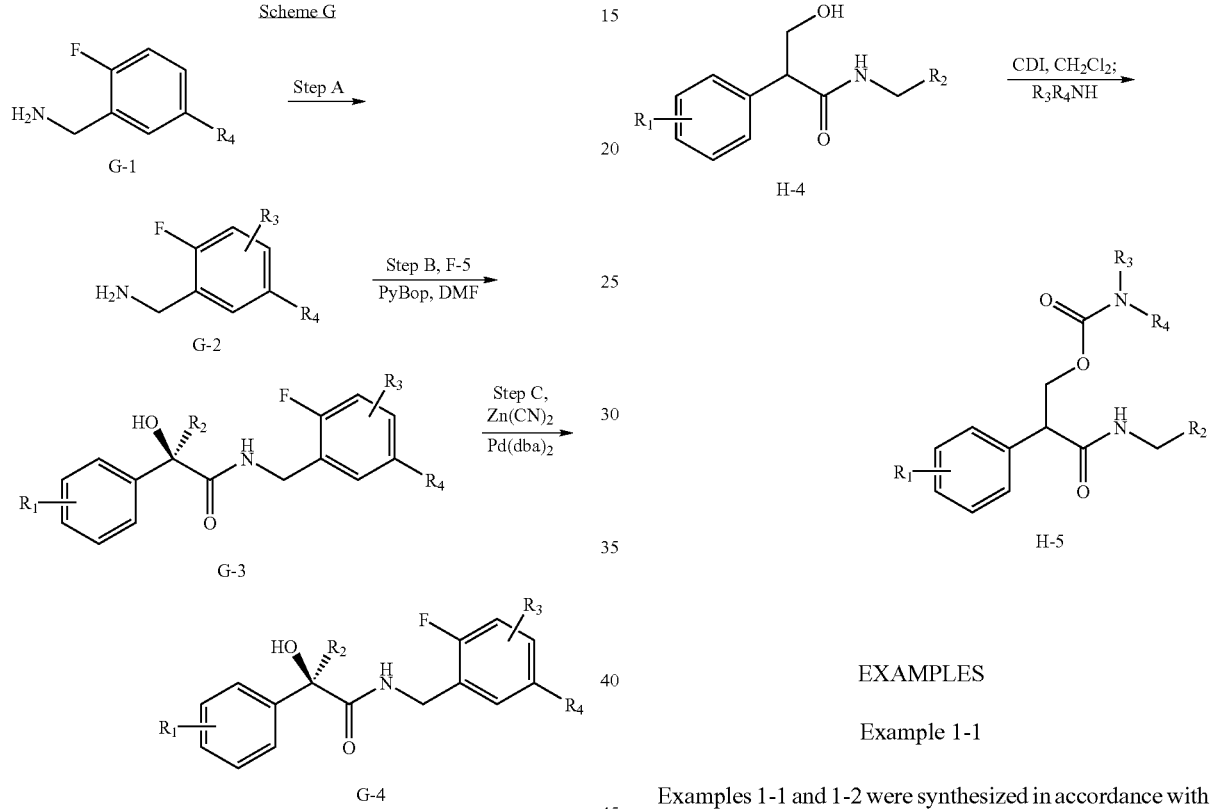
Scheme H
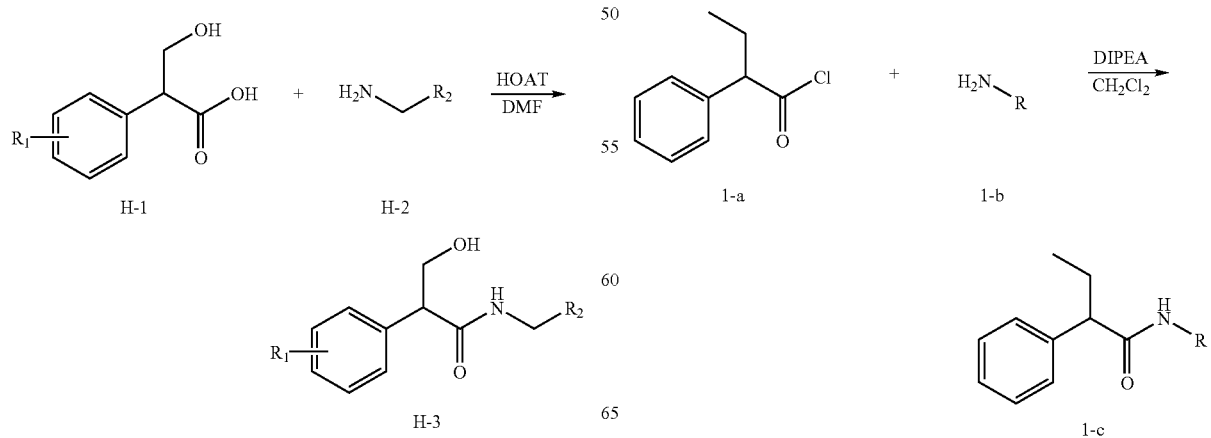
EXAMPLES
Example 1-1
Examples 1-1 and 1-2 were synthesized in accordance with Scheme 1.

-continued

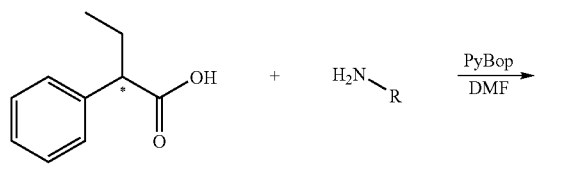

R = substituted phenyl or substituted 3-pyridyl
* = racemic or (S)

(S)—N-(2-fluoro-5-(trifluoromethyl)benzyl)-2-phenylbutanamide (1-1)

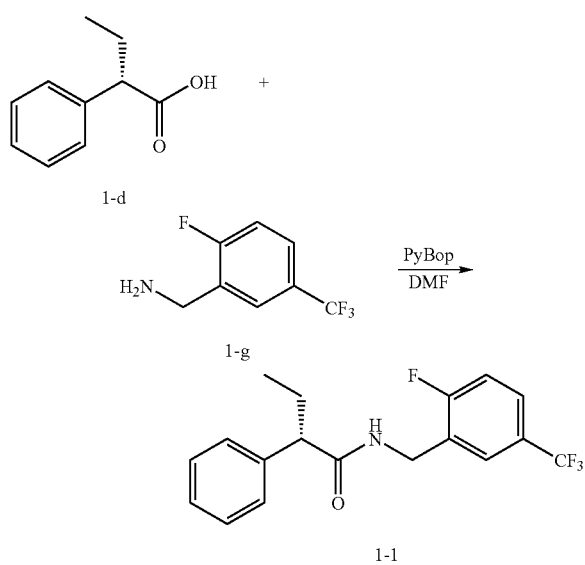

A solution of (S)-2-phenylbutanoic acid (1-d, 50 mg, 0.30 mmol, Sigma-Aldrich, Milwaukee, Wis.) and diisopropylethylamine (98 uL, 0.60 mmol) in N,N-dimethylformamide (1 mL) was treated at room temperature with benzotriazol-1-yloxytripyrrolidinophosphonium hexafluorophosphate (PyBop, 158 mg, 0.30 mmol). After 15 min, (2-fluoro-5-(trifluoromethyl)phenyl)methanamine (1-g, 60 mg, 0.30 mmol, Synthesis, Inc., Wyndham, N.H.) was added. The reaction mixture was stirred for 3 h, partitioned between dichloromethane and 0.5N—NaOH. The aqueous layer was removed and the organic layer was washed with 0.5N—HCl. The aqueous layer was removed by filtering through a plastic frit. The organic layer was concentrated in vacuo to give the desired product (1-1); HRMS (M+1)=340.129; $^1$H NMR (500 MHz, CDCl$_3$) δ7.49 (bs, 1H), 7.41 (d, 1H, J=6.5 Hz), 7.34-7.26 (m, 5H), 7.10 (t, 1H, J=9.0 Hz), 5.77 (bs, 1H), 4.47 (d, 1H, J=3.0 Hz), 3.30 (t, 2H, J=7.5 Hz), 2.22 (m, 1H), 1.82 (m, 1H), 0.89 (t, 3H, J=7.5 Hz).

Example 1-2

N-(2-fluoro-5-methylbenzyl)-2-phenylbutanamide (1-2)

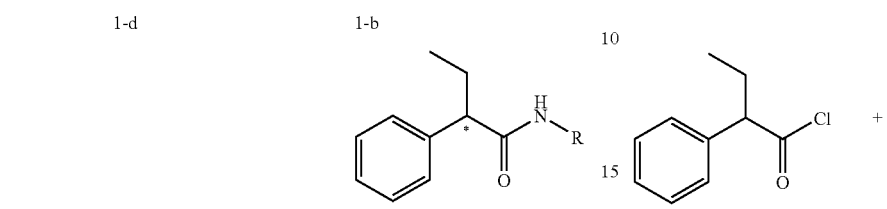

A solution of (2-fluoro-5-methylphenyl)methanamine (1-f, 50 mg, 0.26 mmol, Oakwood Products, Inc., West Columbia, S.C.) and diisopropylethylamine (88 uL, 0.52 mmol) in dichloromethane (1 mL) was treated at room temperature with 2-phenylbutanoyl chloride (1-a, 47 mg, 0.26 mmol). The reaction mixture was stirred for 30 mm, partitioned between dichloromethane and 0.1N—NaOH. The aqueous layer was removed and the organic layer was washed with 0.1N—HCl. The aqueous layer was removed by filtering through a plastic frit. The organic layer was evaporated in vacuo to give the desired product (1-2); HRMS (M+1)= 286.1586.

Additionally, Examples 1-3 through 1-28 in Table 1 below were prepared by the general protocols described in Scheme 1. Specific details of the synthesis of particular compounds are presented below.

Examples 1-6 through 1-9 were obtained by direct introduction of ethyl, vinyl or cyclopropyl group to the corresponding bromide (1-4 or 1-15) by a protocol shown in Scheme 2 (1-6 and 1-7) or known synthetic methods disclosed in Weichert, A. et al., *Synlett* 1996, 473, and Krolski, M. E., et al. *J. Org. Chem.* 1988, 53, 1171 (1-8 and 1-9).

The 2-arylbutanoic acid portion in the compounds of Examples 1-10, 1-11, 1-16 and 1-17 was prepared by alkylation (lithium diisopropylamide; ethyl iodide) of the corresponding ethyl arylacetate followed by the hydrolysis (KOH in MeOH).

The 2-arylbutanoic acid portion in Example 1-19 and 1-20 through 1-28 was prepared according to the procedure described in Myers, A. G., et al.; *J Am Chem. Soc,* 1994, 116, 9361.

The benzylamine portions of the compounds of Examples 1-13, 1-14 and 1-18 (2-e, 2-g and 2-k), respectively, were synthesized as shown below in Scheme 2.

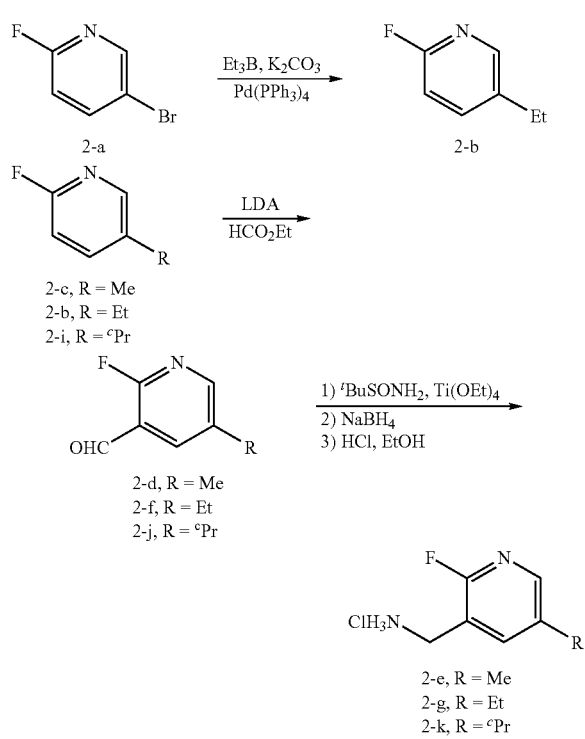

Step A. 5-Ethyl-2-fluoropyridine (2-b)

A mixture of 5-bromo-2-fluoropyridine (2-a, 5.03 g, 28.6 mmol, Lancaster Synthesis, Inc., Wyndham, N.H.), triethylborane (1M in tetrahydrofuran, 42.8 mL, 42.8 mmol), K₂CO₃ (15.8 g, 114.2 mmol) and Pd(PPh₃)₄ (1.65 g, 1.43 mmol) in N,N-dimethylformamide was heated at 85 C for 4 h. The reaction mixture was diluted with water and extracted with hexanes. The organic layer was then washed with water (×2), separated, dried (MgSO₄), and concentrated in vacuo. Chromatography (50%, CH₂Cl₂ in hexanes) afforded the desired product (2-b); ¹H NMR (500 MHz, CDCl₃) δ 8.04 (d, 1H, J =1.0 Hz), 7.60 (dt, 1H, J=8.0, 2.5 Hz), 6.85 (dd, 1H, J=8.3, 2.8 Hz), 2.65 (q, 2H, J=7.8 Hz), 1.21 (t, 3H, J=7.7Hz)

Step B. 5-Ethyl-2-fluoropyridine-3-carbaldehyde (2-f)

A solution of diisopropylamine (1.01 mL, 7.19 mmol) in tetrahydrofuran (20 mL) was treated in ice-bath with n-butyllithium (2.5M, 2.9 mL, 7.19 mmol) and stirred for 30 min. The resulting solution was reacted at −78° C. with 5-ethyl-2-fluoropyridine (2-b, 0.75 g, 5.99 mmol), stirred for 4 h, and treated with N,N-dimethylforninamide (482 mg, 6.59 mmol). The reaction mixture was quenched with acetic acid (1 mL), partitioned between ethyl acetate and water. The organic layer was washed with 0.5N—HCl and then with brine, separated, dried (MgSO₄) and concentrated in vacuo. Chromatography (30% ethyl acetate in hexanes) afforded the desired compound (2-f); ¹H NMR (500 MHz, CDCl₃) δ10.3 (s, 1H), 8.29 (d, 1H, J=2.0 Hz), 8.12 (dd, 1H, J=9.0, 2.5 Hz), 2.73 (q, 2H, J =7.8 Hz), 1.29 (t, 3H, J=7.5 Hz).

Step C. (5-Ethyl-2-fluoropyridin-3-yl)methanamine-hydrogen chloride (2-2)

A solution of 5-ethyl-2-fluoropyridine-3-carbaldehyde (2-f, 152 mg, 0.99 mmol), t-butylsulfinamide (144 mg, 1.19 mmol) and titanium tetraethoxide (679 mg, 2.98 mmol) in tetrahydrofuran (5 mL) was heated at reflux for 2 h. The reaction mixture was cooled to 0° C. and sodium borohydride (150 mg, 3.97 mmol) was introduced. The resulting mixture was stirred at room temperature for 30 min and quenched with methanol. The thick suspension was filtered through a pad of celite and washed with ethyl acetate. The filtrate solution was washed with brine, dried (MgSO₄) and concentrated in vacuo to give the intermediate sulfinamide (148 mg, 58%); The intermediate (148 mg, 0.57 mmol) was treated with ethanol saturated with HCl (5 mL). The reaction mixture was allowed ar room temperature to stir for 30 min and diluted with ethanol (20 mL). All the volatiles were removed in vacuo to give (5-ethyl-2-fluoropyridin-3-yl)methanamine-hydrogen chloride (2-g); ¹H NMR (500 MHz, DMSO-d₆) δ 8.49 (bs, 3H), 8.10 (bs, 1H), 8.03 (dd, 1H, J=9.5, 2.5 Hz), 4.05 (d, 2H, J=5.0 Hz), 2.64 (q, 2H, J=7.5 Hz), 1.21 (t, 3H, J=7.7 Hz).

(2-Fluoro-5-methylpyridin-3-yl)methanamine (2-e)

(2-fluoro-5-methylpyridin-3-yl)methanamine (2-e) was prepared by the same synthetic route as that of (2-g) but utilizing the commercially available 2-fluoro-5-methylpyridine (2-c) as a starting material; ¹H NMR (500 MHz, DMSO-d₆) δ 8.65 (bs, 3H), 8.07 (d, 1H, J=1.0 Hz), 8.01 (dd, 1H, J=15.5, 3.0 Hz), 4.02 (s, 2H), 2.30 (s, 3H).

Example 1-3

Compound 1-3 was synthesized as shown in Scheme 3 and described below.

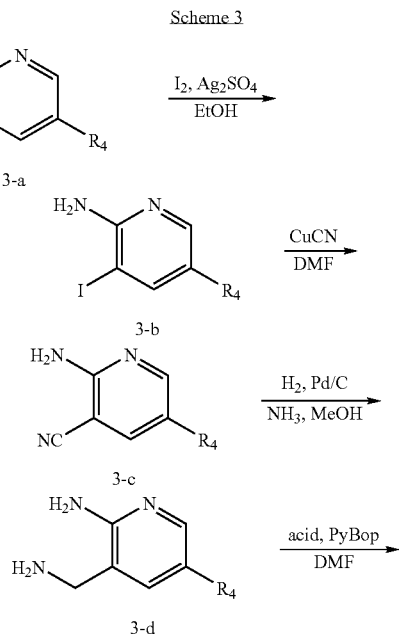

-continued

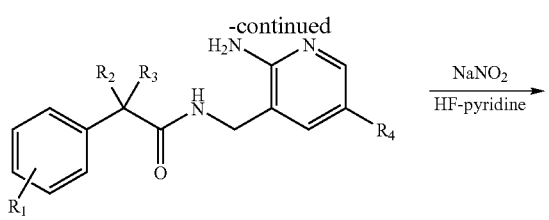

3-e

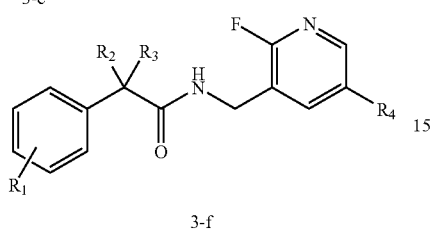

3-f $R_1$ = H, F, Cl, $C_{1-6}$alkyl, $C_{1-6}$ cycloalkyl
$R_2$, $R_3$ = independently H, OH, $C_{1-6}$alkyl, $C_{1-6}$cycloalkyl, $C_{1-6}$ perfluoroalkyl
$R_4$ = independently H, $C_{1-6}$ alkyl or form 5,6-membered ring together Step A (S)—N-((2amino-5-(trifluoromethyl)pyridin-3-yl)methyl)-2-phenylbutanamide (3-g)

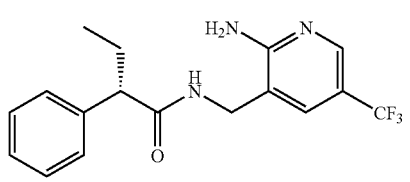

A solution of 5-(trifluoromethyl)pyridin-2-amine (3-a with $R_4$=$CF_3$, 1.6 g, 9.87 mmol) (Maybridge Chemical company, Cornwall, England) in N,N-dimethylformamide (30 mL) was treated at room temperature with silver sulfate (3.1 g, 9.87 mmol) and iodine (2.5 g, 9.87 mol). The reaction mixture was stirred for 14 h and filtered. The filtrated solution was concentrated in vacuo. The residue was chromatographed (SiO$_2$, 25% ethyl acetate in hexanes) to give 5-(trifluoromethyl)-3-iodopyridin-2-amine (3-b, with $R_4$=$CF_3$). The iodide (3-b, with $R_4$=$CF_3$, 1.0 g, 3.47 mmol) and cuprous cyanide (CuCN, 78 g, 8.68 mmol) was dissolved in N,N-dimethylformamide (6 mL) and heated under the microwave at 100 C for 30 min, cooled to ambient temperature, and diluted with ethyl acetate. The precipitates were removed by filtration. The filtrated solution was partitioned between ethyl acetate and water. The organic layer was washed with brine, separated, dried (MgSO$_4$) and concentrated in vacuo. Trituration of the residue with hexanes afforded the desired product, 2amino-5-(trifluoromethyl)pyridine-3-carbonitrile (3-c, with $R_4$=$CF_3$). 2amino-5-(trifluoromethyl)pyridine-3-carbonitrile (3-c, with $R_4$=$CF_3$, 545 mg, 29.2 mmol) was stirred in methanol (10 mL, saturated with ammonia) under hydrogen atmosphere in the presence of Pd/C (200 mg) overnight. The reaction mixture was filtered and the filtrate solution was concentrated in vacuo to afford the crude amine (3-d, with $R_4$=$CF_3$). A solution of (S)-2-phenylbutanoic acid (300 mg, 18.3 mmol) and diisopropylethylamine (888 uL, 52.4 mmol) in N,N-dimethylformamide (5 mL) was treated at room temperature with benzotriazol-1-yloxytripyrrolidinophosphonium hexafluorophosphate (PyBop, 953 mg, 18.3 mmol).

After 15 min, 3-(aminomethyl)-5-(trifluoromethyl)pyridin-2-amine (500 mg, 26.2 mmol) was added. The reaction mixture was stirred for 2 h, partitioned between ethyl acetate and 0.5N—NaOH. The aqueous layer was removed and the organic layer was washed with brine. The organic layer was separated, dried (MgSO$_4$) and concentrated in vacuo to give the desired product (3-g); HRMS (M+1)=338.1405.

Step B (2S)—N-((2-fluoro-5-(trifluoromethyl)pyridin-3-yl)methyl)-2-phenylbutanamide (1-3)

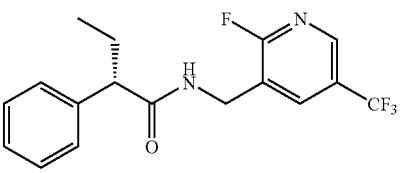

To a solution of 3-g (100 mg, 0.30 mmol) in HF-pyridine (2 mL, in a PEG culture tube) was added while in ice-bath sodium nitrite (61.5 mg, 0.89 mmol) in portions. The reaction mixture was stirred for 30 min, poured in ice, partitioned between ethyl acetate and saturated in aqueous sodium bicarbonate. The organic layer was washed with brine, separated (MgSO$_4$) and concentrated in vacuo. Chromatography (SiO$_2$, 15% ethyl acetate in hexanes) afforded (S)—N-((2-fluoro-5-(trifluoromethyl)pyridin-3-yl)methyl)-2-phenylbutanamide (1-3); HRMS (M+1)=341.1283; $^1$H NMR (500 MHz, CDCl$_3$) δ 8.37 (s, 1H), 7.76 (d, 1H, J=8.5 Hz), 7.37-7.34 (m, 2H), 7.31-7.26 (m, 3H), 5.84 (bs, 1H), 4.50 (dd, 1H, J=16.0, 6.0 Hz), 4.40 (dd, 1H, J=16.0, 6.0 Hz), 3.31 (t, 2H, J=7.8 Hz), 2.20 (m, 1H), 1.82 (m, 1H), 0.88 (t, 3H, J=7.5 Hz).

Example 1-29

Compound 1-29 was synthesized as shown in Scheme 4 and described below.

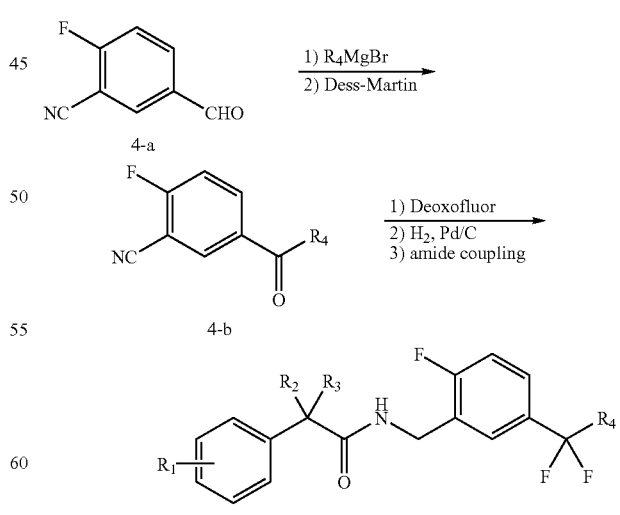

$R_1$ = H, F, Cl, $C_{1-6}$ alkyl, $C_{1-6}$ cycloalkyl
$R_2$, $R_3$ = independently H, OH, $C_{1-6}$ alkyl, $C_{1-6}$ cycloalkyl, $C_{1-6}$ perfluoroalkyl
$R_4$ = independently H, $C_{1-6}$ alkyl or form 5,6-membered ring together

Step A 5-acetyl-2-fluorobenzonitrile (4-d)

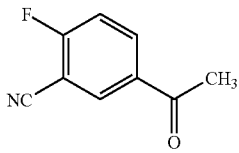

To a stirred solution of 2-fluoro-5-formylbenzonitrile (110 mg, 0.74 mmol) in THF (5 mL) was added at −78 C a solution of methylmagnesium bromide (3M in THF, 0.27 mL, 0.81 mmol). The reaction mixture was stirred at the same temperature for 6 h, warmed up to the room temperature, partitioned between ethyl acetate and saturated NH$_4$Cl. The organic layer was washed with brine, separated, dried (MgSO$_4$) and concentrated in vacuo to give the crude product which was oxidized to the ketone; A solution of the crude alcohol obtained above in CH$_2$Cl$_2$ (10 mL) was reacted at room temperature with Dess-Martin periodinane (493 mg, 1.16 mmol) for 2 h. The reaction mixture was partitioned between CH$_2$Cl$_2$ and 0.5N—NaOH. The organic layer was separated, dried (MgSO$_4$) and concentrated in vacuo to give the crude product which was triturated with hexanes (4-d, 106 mg); $^1$H NMR (500 MHz, CDCl$_3$) δ 8.26-8.21 (m, 2H), 7.34 (t, 1H, J=8.5 Hz), 2.63 (s, 3H).

Step B N-[5-(1,1-difluoroethyl)-2-fluorobenzyl]-2-phenylbutanamide (1-29)

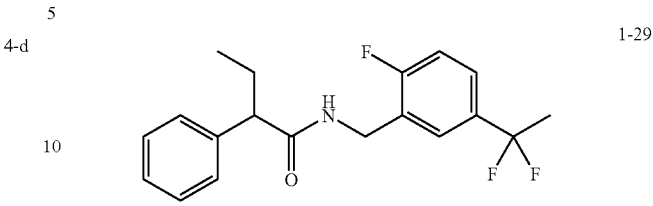

To a stirred solution of the ketone (4-d, 106 mg, 0.65 mmol) in CH$_2$Cl$_2$ (5 mL) was added at 0 C dropwise [bis(2-methoxyethyl)amino]sulfur trifluoride (717 mg, 3.25 mmol). The reaction mixture was stirred at room temperature for 1 h, portioned between ethyl acetate and saturated aqueous NaHCO$_3$. The organic layer was washed with brine, separated, dried (MgSO$_4$) and concentrated in vacuo. The crude product was diluted in MeOH (10 mL) and stirred under H$_2$ atmosphere in the presence of Pd/C (50 mg). After 3 h, the reaction mixture was filtered and the filtrate solution was concentrated in vacuo. The crude amine was diluted with CH$_2$Cl$_2$ (5 mL) and reacted with 2-phenylbutanoyl chloride (119 mg) in the presence of DIEA (0.45 mL, 2.6 mmol). After 3 h, the reaction mixture was concentrated in vacuo and chromatographed (SiO$_2$, 20% ethyl acetate in hexanes) to give the desired product (1-29); HRMS (M+1)=336.1573; $^1$H NMR (500 MHz, CDCl$_3$) δ 7.27 (m, 7H), 7.04 (t, 1H, J=8.5 Hz), 5.78 (s, 1H), 4.47 (d, 1H, J=6.0 Hz), 3.28 (t, 1H, J=7.5 Hz), 2.21 (m, 1H), 1.82 (t, 1H, J=18.0 Hz), 0.89 (t, 1H, J=7.5 Hz)

TABLE 1

| Ex. | Structure | Nomenclature | (LC/MS) or (HRMS) (M + 1 or M + 1 − H$_2$O) |
|---|---|---|---|
| 1-1 | 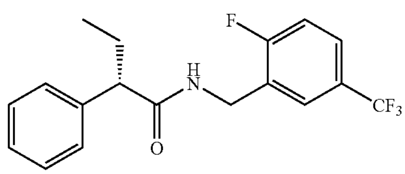 | (S)-N-(2-fluoro-5-(trifluoromethyl)benzyl)-2-phenylbutanamide | 340.1294 |
| 1-2 | 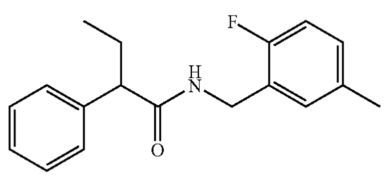 | N-(2-fluoro-5-methylbenzyl)-2-phenylbutanamide | 286.1586 |
| 1-3 | 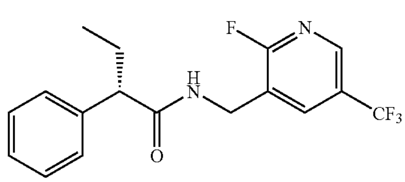 | (S)-N-((2-fluoro-5-(trifluoromethyl)pyridin-3-yl)methyl)-2-phenylbutanamide | 341.1283 |

TABLE 1-continued

| Ex. | Structure | Nomenclature | (LC/MS) or (HRMS) (M + 1 or M + 1 − H₂O) |
|---|---|---|---|
| 1-4 | 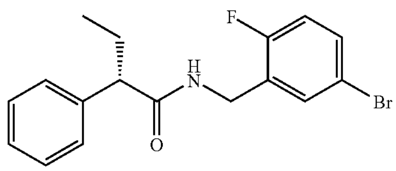 | (S)-N-(5-bromo-2-fluorobenzyl)-2-phenylbutanamide | 350.0478 |
| 1-5 | 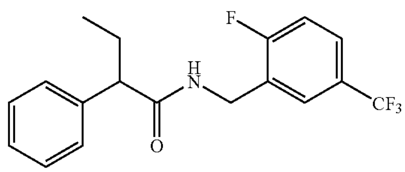 | N-(2-fluoro-5-(trifluoromethyl)benzyl)-2-phenylbutanamide | 340.1255 |
| 1-6 | 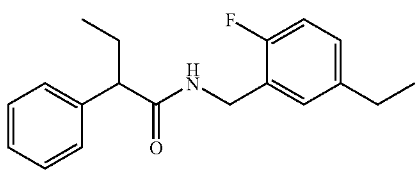 | N-(5-ethyl-2-fluorobenzyl)-2-phenylbutanamide | 300.1770 |
| 1-7 | 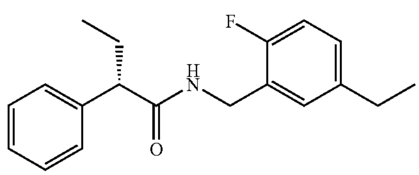 | (S)-N-(5-ethyl-2-fluorobenzyl)-2-phenylbutanamide | 300.1768 |
| 1-8 | 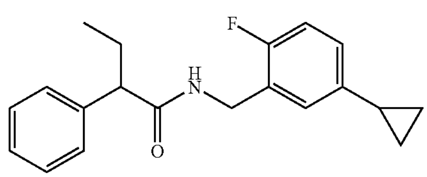 | N-(5-cyclopropyl-2-fluorobenzyl)-2-phenylbutanamide | 312.1739 |
| 1-9 | 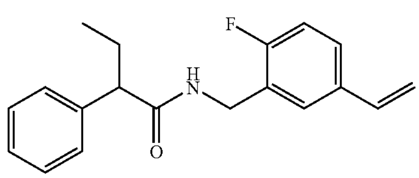 | N-(2-fluoro-5-vinylbenzyl)-2-phenylbutanamide | 298.1585 |
| 1-10 | 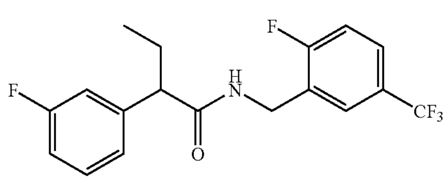 | N-(2-fluoro-5-(trifluoromethyl)benzyl)-2-(3-fluorophenyl)butanamide | 358.1235 |
| 1-11 | 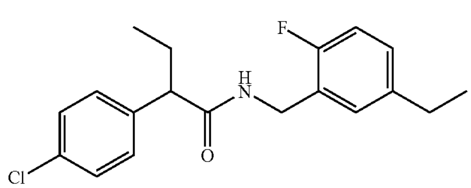 | N-(5-ethyl-2-fluorobenzyl)-2-(4-chlorophenyl)butanamide | 334.1373 |

TABLE 1-continued

| Ex. | Structure | Nomenclature | (LC/MS) or (HRMS) (M + 1 or M + 1 − H₂O) |
|---|---|---|---|
| 1-12 | 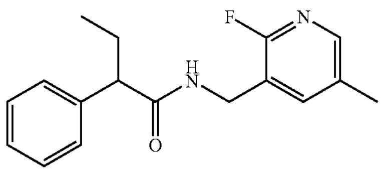 | N-((2-fluoro-5-methylpyridin-3-yl)methyl)-2-phenylbutanamide | 287.1540 |
| 1-13 | 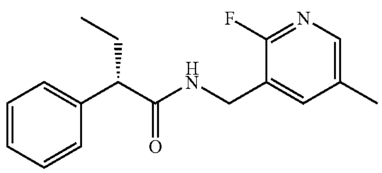 | (S)-N-((2-fluoro-5-methylpyridin-3-yl)methyl)-2-phenylbutanamide | 287.1539 |
| 1-14 | 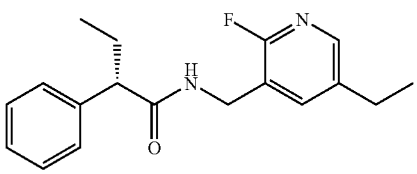 | (S)-N-((5-ethyl-2-fluoropyridin-3-yl)methyl)-2-phenylbutanamide | 301.1725 |
| 1-15 | 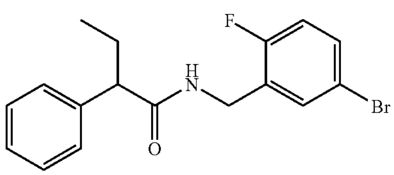 | N-(5-bromo-2-fluorobenzyl)-2-phenylbutanamide | 350.0481 |
| 1-16 | 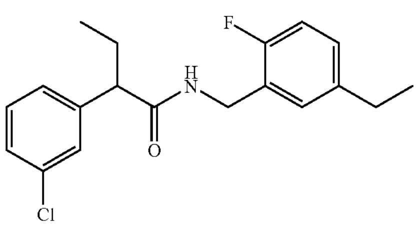 | N-(5-ethyl-2-fluorobenzyl)-2-(3-chlorophenyl)butanamide | 334.1374 |
| 1-17 | 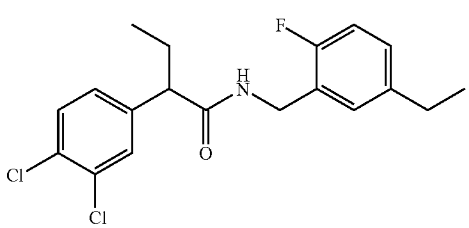 | N-(5-ethyl-2-fluorobenzyl)-2-(3,4-dichlorophenyl)butanamide | 368.0989 |
| 1-18 | 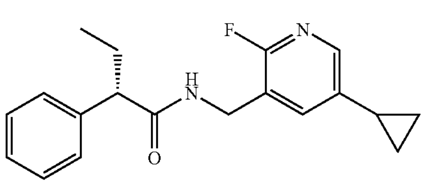 | (S)-N-((5-cyclopropyl-2-fluoropyridin-3-yl)methyl)-2-phenylbutanamide | 313.1685 |

TABLE 1-continued

| Ex. | Structure | Nomenclature | (LC/MS) or (HRMS) (M + 1 or M + 1 − H$_2$O) |
|---|---|---|---|
| 1-19 | 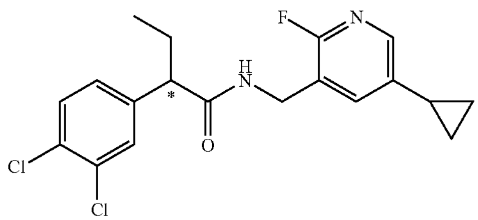 | (2R or 2S)-N-[(5-cyclopropyl-2-fluoropyridin-3-yl)methyl]-2-(3,4-dichlorophenyl)butanamide | 381.0927 |
| 1-20 | 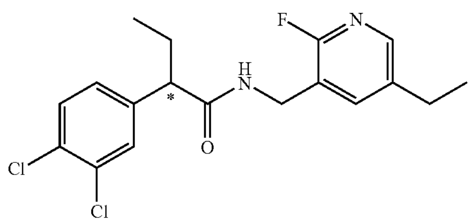 | (2R or 2S)-N-[(5-ethyl-2-fluoropyridin-3-yl)methyl]-2-(3,4-dichlorophenyl)butanamide | (LC/MS) 369.1 |
| 1-21 | 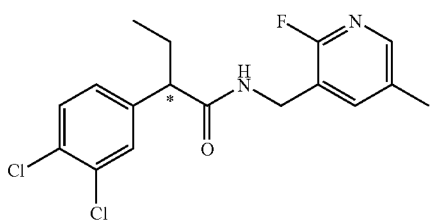 | (2R or 2S)-N-[(5-methyl-2-fluoropyridin-3-yl)methyl]-2-(3,4-dichlorophenyl)butanamide | (LC/MS) 355.0 |
| 1-22 | 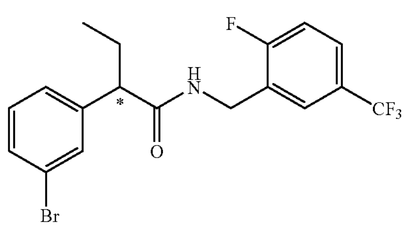 | (2R or 2S)-N-(2-fluoro-5-(trifluoromethyl)benzyl)-2-(3-bromophenyl)butanamide | (LC/MS) 418.0 |
| 1-23 | 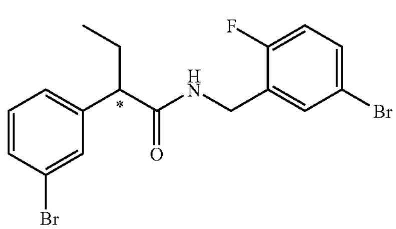 | (2R or 2S)-N-(5-bromo-2-fluorobenzyl)-2-(3-bromophenyl)butanamide | (LC/MS) 428.0 |
| 1-24 | 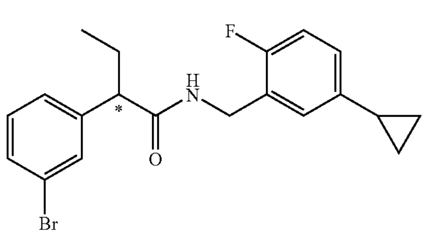 | (2R or 2S)-N-(5-(cyclopropyl)-2-fluorobenzyl)-2-(3-bromophenyl)butanamide | (LC/MS) 390.0 |

TABLE 1-continued

| Ex. | Structure | Nomenclature | (LC/MS) or (HRMS) (M + 1 or M + 1 − H₂O) |
|---|---|---|---|
| 1-25 | 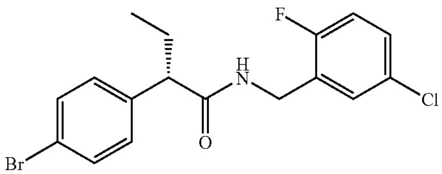 | (2R or 2S)-N-(5-chloro-2-fluorobenzyl)-2-(4-bromophenyl)butanamide | (LC/MS) 384.0 |
| 1-26 | 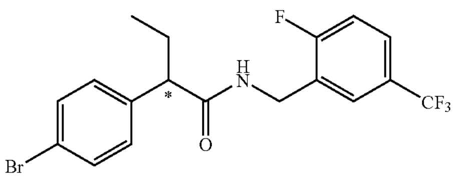 | (2R or 2S)-N-(2-fluoro-5-(trifluoromethyl)benzyl)-2-(4-bromophenyl)butanamide | (LC/MS) 418.0 |
| 1-27 | 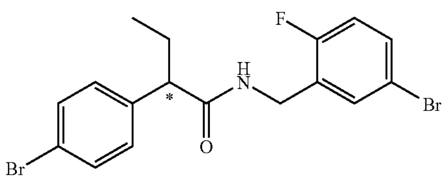 | (2R or 2S)-N-(5-bromo-2-fluorobenzyl)-2-(4-bromophenyl)butanamide | (LC/MS) 428.0 |
| 1-28 | 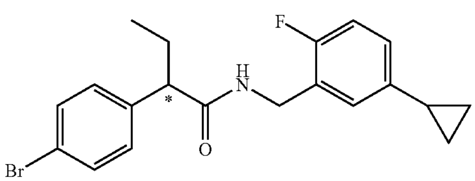 | (2R or 2S)-N-(5-(cyclopropyl)-2-fluorobenzyl)-2-(4-bromophenyl)butanamide | (LC/MS) 390.0 |
| 1-29 | 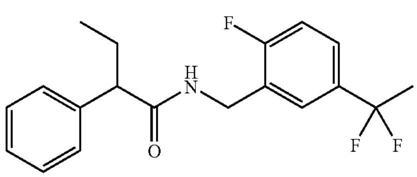 | N-[5-(1,1-difluoroethyl)-2-fluorobenzyl]-2-phenylbutanamide | 336.1573 |

Example 2-1

Compound 2-1 was synthesized in accordance with the procedure outlined in Scheme 5 and described below.

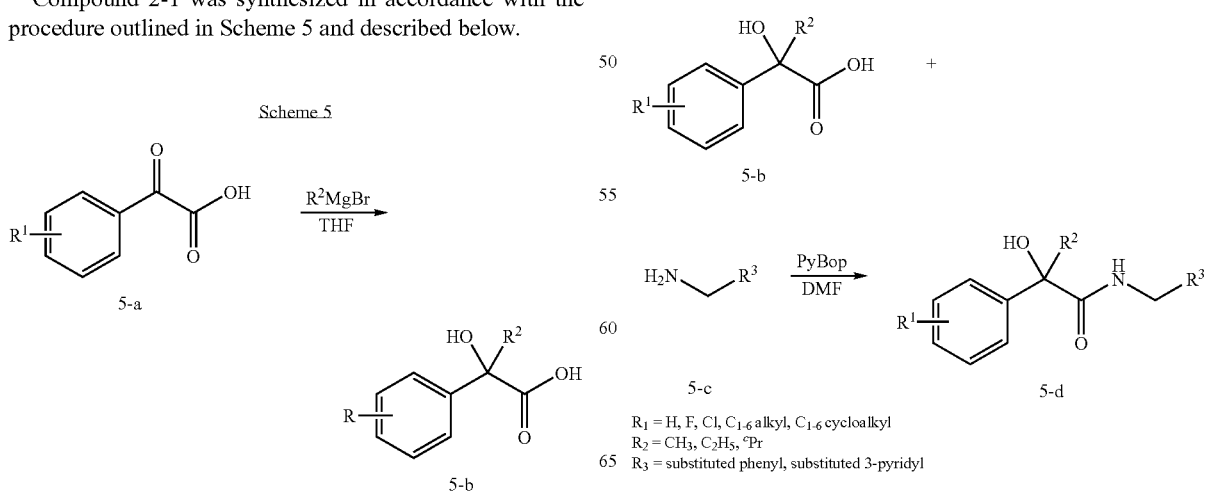

Scheme 5

$R_1$ = H, F, Cl, $C_{1-6}$ alkyl, $C_{1-6}$ cycloalkyl
$R_2$ = $CH_3$, $C_2H_5$, $^cPr$
$R_3$ = substituted phenyl, substituted 3-pyridyl

(2R or 2S)—N-(2-fluoro-5-(trifluoromethyl)benzyl)-2-hydroxy-2-phenylbutanamide (2-1)

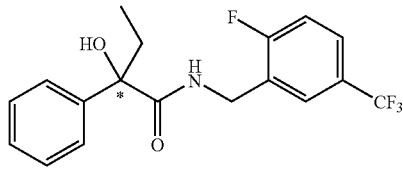

A solution of 2-oxo-2-phenylacetic acid (10 g, 66.6 mmol) (Acros Organics B.V.B.A., Belgium) in tetrahydrofuran (THF, 200 mL) was treated at room temperature with ethylmagnesium bromide (2.5 M, 80 mL, 200 mmol). The reaction mixture was stirred for 5 h, partitioned between ethyl acetate and 1N—HCl. The organic layer was separated, dried (MgSO$_4$) and concentrated in vacuo to afford 2-hydroxy-2-phenylbutanoic acid. A solution of 2-hydroxy-2-phenylbutanoic acid (100 mg, 0.55 mmol) and diisopropylethylamine (188 uL, 1.11 mmol) in N,N-dimethylformamide (2 mL) was treated at room temperature with benzotriazol-1-yloxytripyrrolidinophosphonium hexafluorophosphate (PyBop, 290 mg, 0.55 mmol). After 15 min, (3-fluoro-5-(trifluoromethyl)phenyl)methanamine (107 mg, 0.55 mmol) was added. The reaction mixture was stirred for 3 h, partitioned between dichloromethane and 0.5N—NaOH. The aqueous layer was removed and the organic layer was washed with 0.5N—HCl. The aqueous layer was removed by filtering through a plastic fit. The organic layer was evaporated in vacuo to give the racemic mixture of the amide which was resolved using the chiral column (CiralPak AD) to give the desired product (2-1); HRMS (M+H−H$_2$O)=338.1167; $^1$H NMR (500 MHz, CDCl$_3$) δ 7.59 (d, 1H, J=7.5 Hz), 7.51 (m, 1H), 7.42 (d, 1H, J=5.0 Hz), 7.37 (t, 1H, J=7.5 Hz), 7.32 (d, 1H, J=7.0 Hz), 7.13 (t, 1H, J=9.0 Hz), 7.01 (bs, 1H), 4.52 (dq, 2H, J=15.6, 6.4 Hz), 2.83 (s, 1H), 2.36 (m, 1H), 2.12 (m, 1H), 0.94 (t, 3H, J=7.2 Hz).

Compounds, 2-1 through 2-5, exemplified in Table 2 were synthesized as shown in Scheme 5. The acid portion of the compound of Example 2-2 was prepared by a known method (Negishi, E., et al., *Tetrahedron Lett.* 1983, 24, 5181) followed by Grignard reaction (EtMgBr) and the hydrolysis of the ester (KOH in aq. EtOH).

TABLE 2

| Ex. | Structure | Nomenclature | HRMS (M + 1 or M + 1 − H$_2$O) |
|---|---|---|---|
| 2-1 | 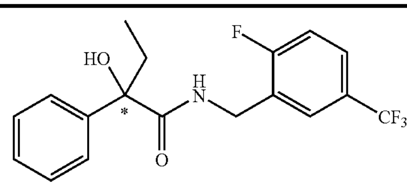 | (2R or 2S)-N-(2-fluoro-5-(trifluoromethyl)benzyl)-2-hydroxy-2-phenylbutanamide | 338.1167 |
| 2-2 | 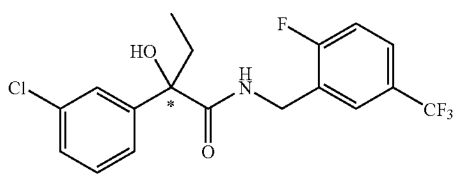 | (2R or 2S)-N-(2-fluoro-5-(trifluoromethyl)benzyl)-2-(3-chlorophenyl)-2-hydroxybutanamide | 389.0811 |
| 2-3 | 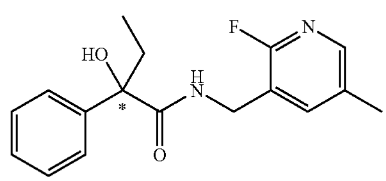 | (2R or 2S)-N-((2-fluoro-5-methylpyridin-3-yl)methyl)-2-hydroxy-2-phenylbutanamide | 303.1518 |
| 2-4 | 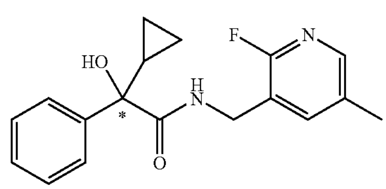 | (2R or 2S)-2-cyclopropyl-N-((2-fluoro-5-methylpyridin-3-yl)methyl)-2-hydroxy-2-phenylacetamide | 315.1521 |
| 2-5 | 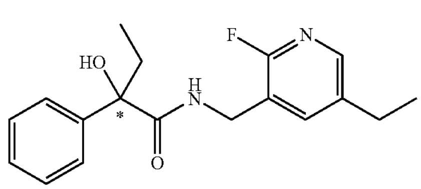 | (2R or 2S)-N-((5-ethyl-2-fluoropyridin-3-yl)methyl)-2-hydroxy-2-phenylbutanamide | 317.1680 |

Example 3-1

Compound 3-1 was synthesized in accord with the general procedure outlined in Scheme 6 below.

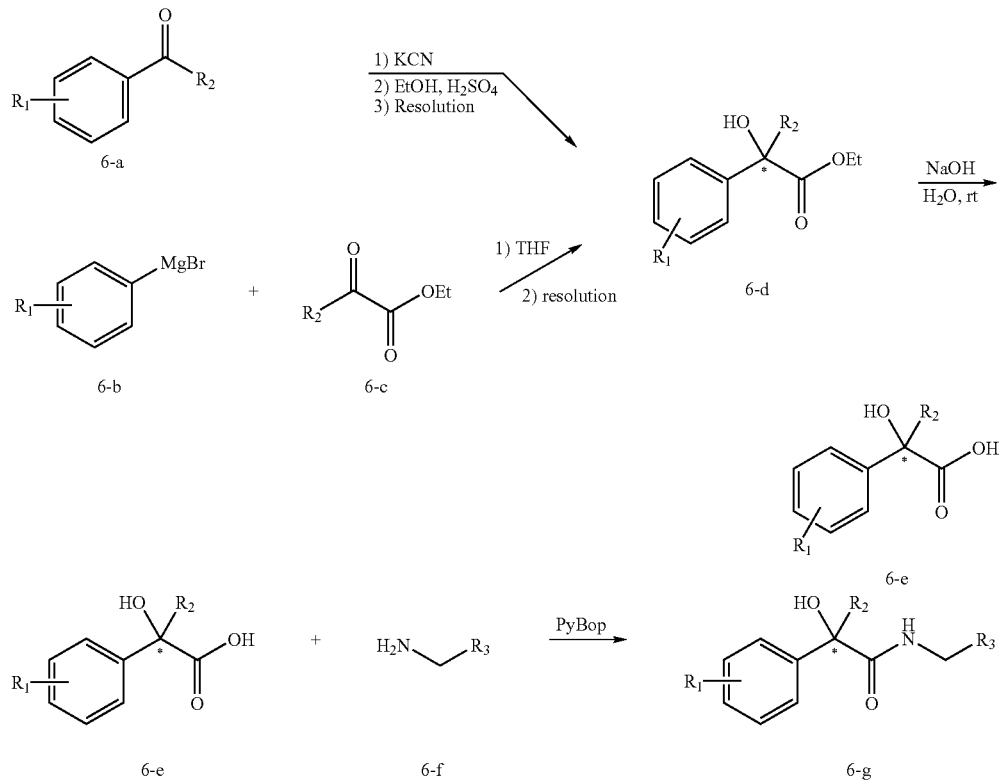

$R_1$ = H, F, Cl, $C_{1-6}$alkyl, $C_{1-6}$ cycloalkyl
$R_2$ = $CF_3$, $C_2F_5$
$R_3$ = substituted phenyl, substituted 3-pyridyl (2R)-3(3,3-trifluoro-N-[(2-fluoro-5-methylpyridin-3-yl)methyl]-2-hydroxy-2-phenylpropanamide (3-1)

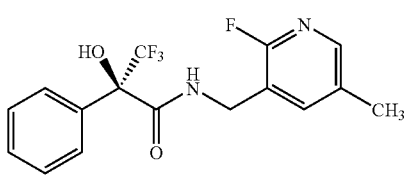

A solution of (2R)-3,3,3-trifluoro-2-hydroxy-2-phenylpropanoic acid (6-e with R=$CF_3$ and R'=H, 105 mg, 0.48 mmol), the amine (2-e, 67 mg, 0.48 mmol) and diisopropylethylamine (415 uL, 2.4 mmol) in N,N-diinethylformainide (1 mL) was treated at room temperature with benzotriazol-1-yloxytripyrrolidinophosphonium hexafluorophosphate (Py-Bop, 274 mg, 0.53 mmol). After 14 h, the reaction mixture was partitioned between ethyl acetate and 0.5N—NaOH. The aqueous layer was removed and the organic layer was washed with 0.5N—HCl. The aqueous layer was removed by filtering through a plastic fit. The organic layer was evaporated in vacuo to give the desired product (3-1); HRMS (M+H)= 343.1059; $^1$H NNMR (500 MHz, $CDCl_3$) δ 7.89 (bs, 1H), 7.63 (m, 2H), 7.43 (m, 3H), 7.39 (d, 1H, J=7.8 Hz), 6.67 (br, 1H), 4.72 (m, 1H), 4.48 (d, 2H, J=6.1 Hz), 2.26 (s, 3H);

compound 3-3 [(2R)-3,3,3-trifluoro-N-(2-fluoro-5-trifluoroinethylbenzyl)-2-hydroxy-2-phenylpropanamide] was prepared by the same procedure (2-fluoro-5-trifluoromethylbenzylainine was purchased from Alfa Aesar); HRMS (M+H)= 396.0825; $^1$H NMR (500 MHz, DMSO-$d_6$) δ 8.95 (t, 1H), 7.95 (s, 1H), 7.65 (in, 3H), 7.39 (m, 5H), 4.40 (dq, 2H).

The carboxylic acid moieties of 3-1 through 3-10, 3-11 in Table 3 were prepared from 6-a as shown in Scheme 6 by a known method (Mosher, H. S., et at., *J. Org. Chem.* 1969, 34, 2543). Resolution of the enantioineric mixture of the ester was carried out with the ChiralPack AD [360 nm, 95% Hexanes (0.1% diethylainine) and 5% MeOH/EtOH (1:1)] instead of the fractional crystallization of the acid as reported in the literature. The absolute configuration of (2R)-3,3,3-trifluoro-2-hydroxy-2-phenylpropanoic acid (6-e with $R_1$=H and $R_2$=$CF_3$) was determined to be R (measured $[α]_D$+24.8, c 0.1, MeOH; literature $[α]_D$+29.8, c 0.8, MeOH, Sharpless, K. B. et al., *Tetrahedron: Asymmetry* 1994, 5, 1473). The absolute configuration of resolved 3,3,4,4,4-pentafluoro-2-hydroxy-2-phenylbutanoic acid has not been established. Under the same resolution condition, the pentafluoroethyl analog (6-d with $R_1$=H and $R_2$=$C_2F_5$) gave two peaks at 18 and 21 minutes, respectively. The acid (6-e with $R_1$=H and $R_2$=$C_2F_5$) that afforded the active coupled compound (for example, (2R)-3-2 or (2S)-3-2, Table 3) in the biochemical assays was that of the second peak (RT=21 min, $[\alpha]_D$+4.4, c 0.1, MeOH).

Example 3-12

Compound 3-12 was also synthesized in accord with the general procedure outlined in Scheme 6.

(2R or 2S)-2-(4-chloro-3-fluorophenyl)-3,3,3-trifluoro-[2-fluoro-5-(trifluoromethyl)benzyl]-2-hydroxypropanamide (3-12)

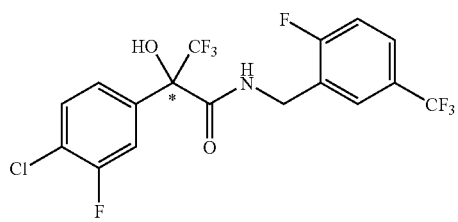

To a stirred solution of the pyruvate (6-c with R=CF$_3$, 4 g, 23.5 mmol) in tetrahydrofuran (100 mL) was added at −78 C a solution of the Grignard reagent (6-b with R'=4-Chloro-3-fluoro, 1M, 24.7 mL, 24.7 mmol). After 1 h, the dry-ice bath was removed. The reaction mixture was stirred overnight, quenched with 1N—HCl, partitioned between diethylether, washed with brine, dried (MgSO$_4$) and concentrated in vacuo. Chromatography (SiO$_2$, 20% ethyl acetate in hexanes) afforded 4.5 g of the desired ester which was subsequently resolved [6-d, Chiracel AD, 10 cm, 5%-(EtOH/MeOH, 1:1)/hexanes (with 1% diethylamine)], hydrolyzed (6-e, KOH, aqueous ethanol) and coupled to the amine to give 3-12, HRMS (M+H)=448.0340; $^1$H NMR (500 MHz, CDCl$_3$) δ 7.57 (m, 1H), 7.50-7.44 (m, 3H), 7.40 (d, 1H, J=8.6 Hz), 7.17 (t, 1H, J=9.0 Hz), 6.67 (bs, 1H), 4.60 (d, 2H, J=5.8 Hz), 4.58 (d, 1H, J=2.0 Hz).

Examples 3-13, 3-14 and 3-15

Compounds 3-13, 3-14 and 3-15 in Table 3 were prepared as shown in Scheme 7.

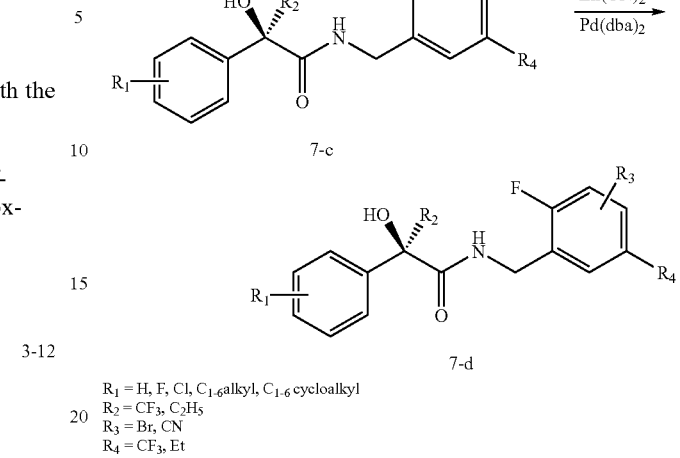

R$_1$ = H, F, Cl, C$_{1-6}$alkyl, C$_{1-6}$ cycloalkyl
R$_2$ = CF$_3$, C$_2$H$_5$
R$_3$ = Br, CN
R$_4$ = CF$_3$, Et Step A:

To a suspension of 2-fluoro-5-trifluoromethylbenzylamine (0.2 g, 11.0 mmol) and 1,3-dibromo-5,5-dimethylhydantoin (0.15 g, 0.5 mmol) in 3 mL anhydrous CH$_2$Cl$_2$ was added triflic acid (0.4 g, 2.9 mmol). The reaction mixture was shielded from light and stirred at room temperature for overnight. 10 mL water was added. The organic layer was separated. The water layer was basified by K$_2$CO$_3$ and concentrated to yield a solid which was extracted by ether. The combined ether layer was concentrated to afford the desired product (7-e, LC/MS found: 273.9); 7-f was prepared with the same protocol;
LC/MS: 232.03.

Step B:

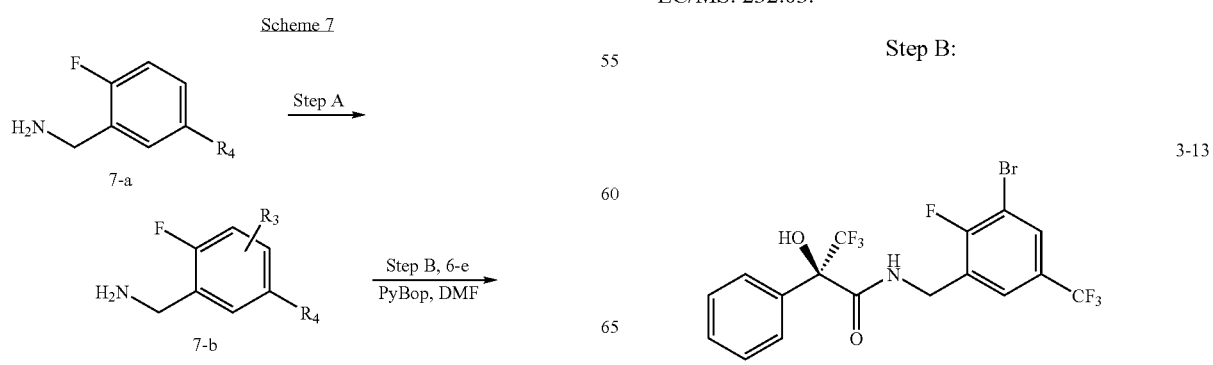

-continued

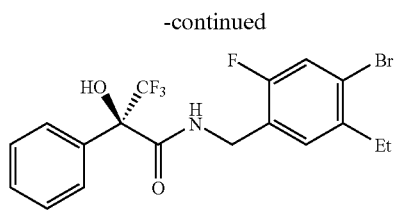
7-g

A protocol described for the preparation of 3-1, from 7-e or 7-f, was used to prepare 3-13 and 7-g, respectively (MS found: 473.9924 for 3-13 and 434.0 for 7-g).

Step C:

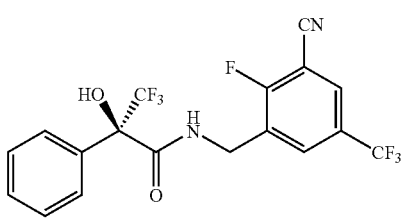
3-14

-continued

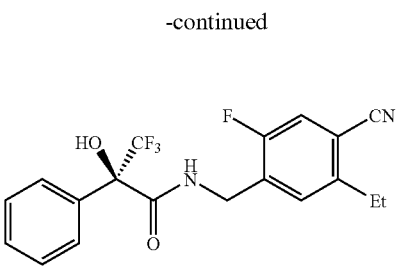
3-15

A mixture of 3-13 (0.2 g, 0.4 mmol), $Zn(CN)_2$ (0.1 g, 0.8 mmol), Zn (0.003 g, 0.04 mmol), $Pd_2(dba)_3$ (0.02 g, 0.02 mmol) and dppf (0.02 g, 0.04 mmol) in 3 mL DMF was bubbled $N_2$ for 5 mins. The mixture was heated in a microwave reactor at 150° C. for 30 mins. The mixture was filtered and loaded to Gilson™ reverse phase chromatography (5-85% Acetonitrile over 20 mins) to afford the desired product 3-14 (MS found: 421.0780); 3-15 was prepared by the same method from 7-g (MS found: 381.1216).

Compounds in Table 3 were prepared as shown in Scheme 6 (3-1 through 3-12) or Scheme 7 (3-13 through 3-15).

TABLE 3

| Ex. | Structure | Nomenclature | (LC/MS) or (HRMS) (M + 1 or M + 1 − $H_2O$) |
|---|---|---|---|
| 3-1 | 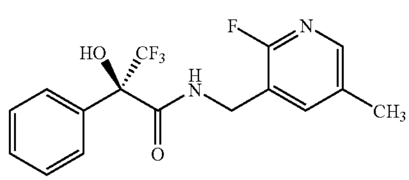 | (2R)-3,3,3-trifluoro-N-[(2-fluoro-5-methylpyridin-3-yl)methyl]-2-hydroxy-2-phenylpropanamide | 343.1059 |
| 3-2 | 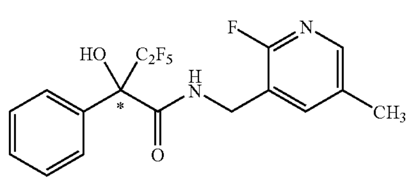 | (2R or 2S)-3,3,4,4,4-pentafluoro-N-[(2-fluoro-5-methylpyridin-3-yl)methyl]-2-hydroxy-2-phenylbutanamide | 393.1035 |
| 3-3 | 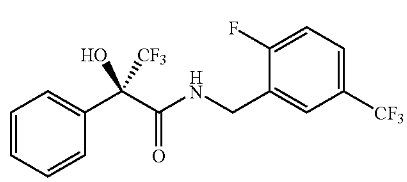 | (2R)-3,3,3-trifluoro-N-(2-fluoro-5-trifluoromethylbenzyl)-2-hydroxy-2-phenylpropanamide | 396.0825 |
| 3-4 | 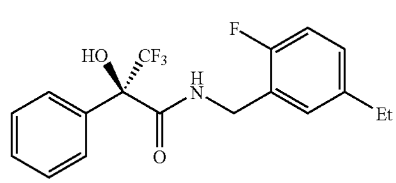 | (2R)-3,3,3-trifluoro-N-(2-fluoro-5-ethylbenzyl)-2-hydroxy-2-phenylpropanamide | 362.0562 |

TABLE 3-continued

| Ex. | Structure | Nomenclature | (LC/MS) or (HRMS) (M + 1 or M + 1 − H$_2$O) |
|---|---|---|---|
| 3-5 | 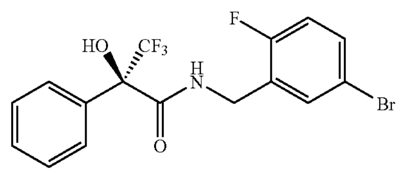 | (2R)-3,3,3-trifluoro-N-(2-fluoro-5-bromobenzyl)-2-hydroxy-2-phenylpropanamide | 406.0060 |
| 3-6 | 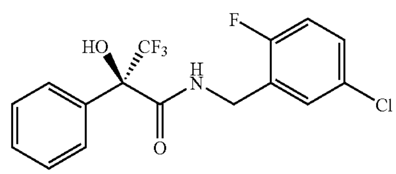 | (2R)-3,3,3-trifluoro-N-(2-fluoro-5-chlorobenzyl)-2-hydroxy-2-phenylpropanamide | 362.0562 |
| 3-8 | 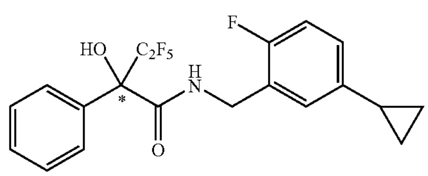 | (2R or 2S)-3,3,4,4,4-pentafluoro-N-(2-fluoro-5-cyclopropylbenzyl)-2-hydroxy-2-phenylbutanamide | 418.1238 |
| 3-9 | 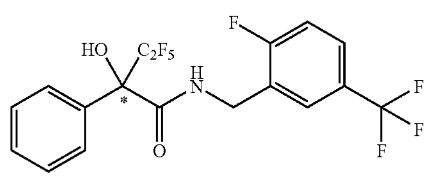 | (2R or 2S)-3,3,4,4,4-pentafluoro-N-(2-fluoro-5-trifluoromethylbenzyl)-2-hydroxy-2-phenylbutanamide | 446.0796 |
| 3-10 | 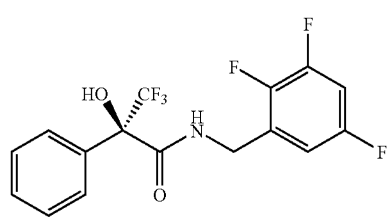 | (2R)-3,3,3-trifluoro-N-(2,3,5-trifluorobenzyl)-2-hydroxy-2-phenylpropanamide | 364.7592 |
| 3-11 | 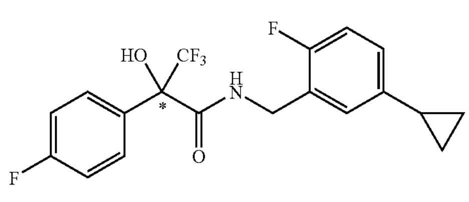 | (2R or 2S)-2-(4-fluorophenyl)-3,3,3-trifluoro-[2-fluoro-5-(cyclopropylbenzyl]-2-hydroxypropanamide | 386.1138 |
| 3-12 | 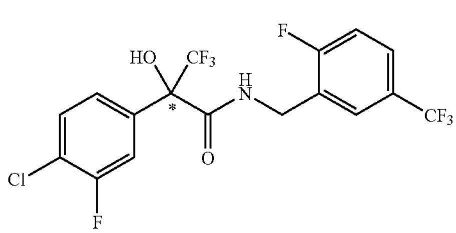 | (2R or 2S)-2-(4-chloro-3-fluorophenyl)-3,3,3-trifluoro-[2-fluoro-5-(trifluoromethyl)benzyl]-2-hydroxypropanamide | 448.0340 |

TABLE 3-continued

| Ex. | Structure | Nomenclature | (LC/MS) or (HRMS) (M + 1 or M + 1 − H$_2$O) |
|---|---|---|---|
| 3-13 | 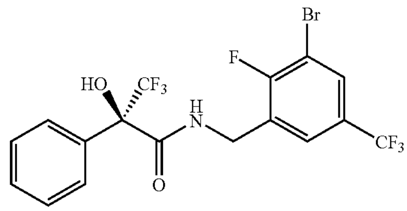 | (2R)-3,3,3-trifluoro-N-(2-fluoro-3-bromo-5-trifluoromethylbenzyl)-2-hydroxy-2-phenylpropanamide | 473.9924 |
| 3-14 | 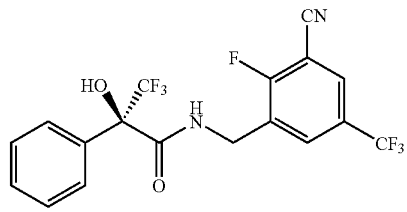 | (2R)-3,3,3-trifluoro-N-(2-fluoro-3-cyano-5-trifluoromethylbenzyl)-2-hydroxy-2-phenylpropanamide | 421.0780 |
| 3-15 | 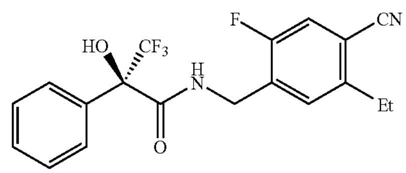 | (2R)-3,3,3-trifluoro-N-(2-fluoro-4-cyano-5-ethylbenzyl)-2-hydroxy-2-phenylpropanamide | 381.1216 |

Example 4-1

Compound 4-1 in Table 4 was prepared in accordance with Scheme 8.

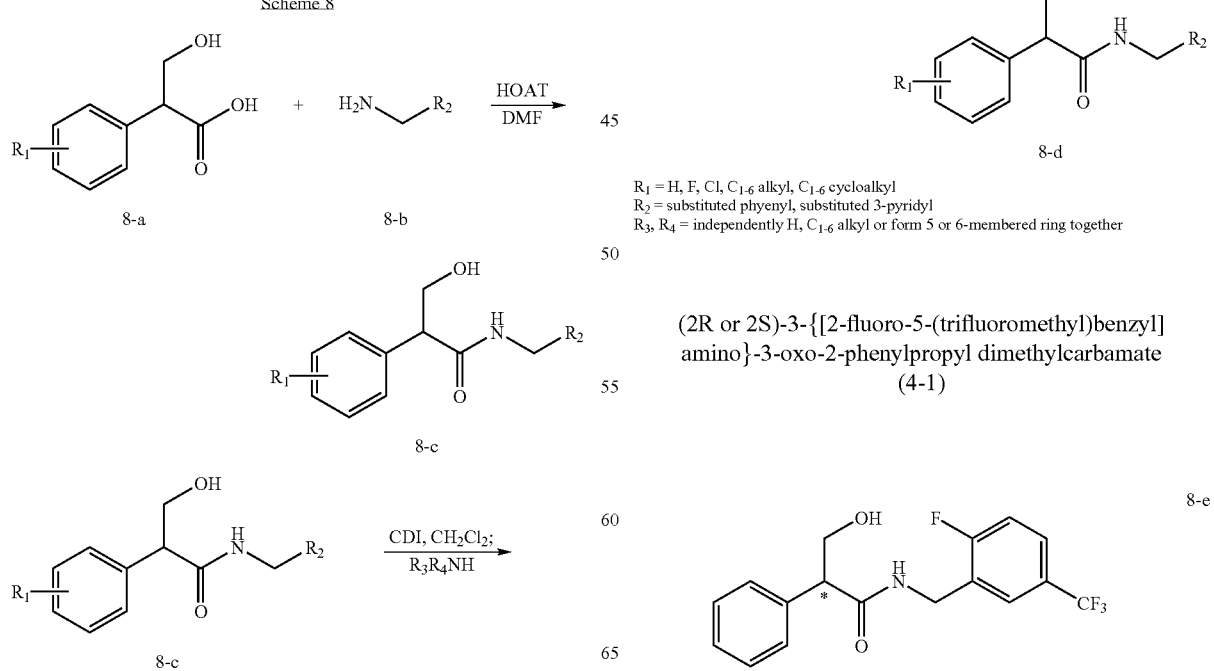

$R_1$ = H, F, Cl, $C_{1-6}$ alkyl, $C_{1-6}$ cycloalkyl
$R_2$ = substituted phyenyl, substituted 3-pyridyl
$R_3$, $R_4$ = independently H, $C_{1-6}$ alkyl or form 5 or 6-membered ring together (2R or 2S)-3-{[2-fluoro-5-(trifluoromethyl)benzyl]amino}-3-oxo-2-phenylpropyl dimethylcarbamate
(4-1)

-continued

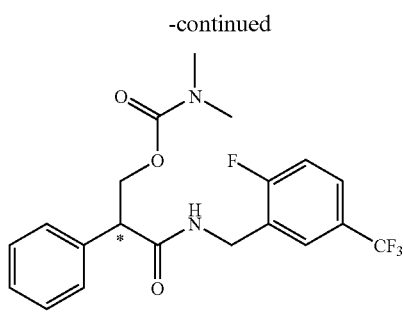

4-1

A solution of tropic acid (8-a with $R_1$=H, 1.00 g, 6.02 mmol) and (3-fluoro-5-(trifluoromethyl)phenyl)methanamine (1.28 g, 6.62 mmol) in N,N-dimethylformamide (10 mL) was treated at room temperature with 1-hydroxy-7-azabenzotriazole (HOAt, 0.98 g, 7.22 mmol) and 1-(3-Dimethylaminopropyl)3-ethylcarbodiimide HCl (EDC, 1.38 g, 7.22 mmol). After 14 h, the reaction mixture was partitioned between dichloromethane and 0.5N—NaOH. The organic layer was dried with sodium sulfate, filtered and concentrated in vacuo. Chromatography ($SiO_2$, 0-80% ethyl acetate in hexanes) afforded 1.7 g of the desired alcohol which was subsequently resolved [Chiracel AD, 10 cm, 15% isopropanol/hexanes (with 1% diethylamine)], to give alcohol 8-e. A solution of alcohol (8-e, 53 mg, 0.146 mmol) and DMAP (2.5 mg, 0.015 mmol) in dichloromethane (1 mL) was treated at room temperature with carbonyldiimidazole (CDI, 33 mg, 0.205 mmol.). After 1 h, dimethylamine (0.44 mL, 0.438 mmol, 1 M in THF) was added. After 14 h, the reaction mixture was partitioned between dichloromethane and 0.5N—NaOH. The organic layer was dried with sodium sulfate, filtered and concentrated in vacuo. Chromatography ($SiO_2$, 0-80% ethyl acetate in hexanes) afforded the desired product 4-1; LRMS (M+H)=413.1491; $^1$H NMR (500 MHz, $CDCl_3$) δ 7.51 (m, 1H), 7.45 (m, 1H), 7.26 (m, 5H), 7.11 (t, 1H, J=9.0 Hz), 6.01 (br, 1H), 4.61 (m, 1H), 4.52 (m, 2H), 4.42 (dd, 1H, J=11.0, 6.1 Hz), 3.86 (m, 1H), 2.76 (s, 3H), 2.70 (s, 3H), 2.60 (bs, 1H).

Additionally, compounds 4-2 through 4-6 in Table 4 were prepared by simple modification of the protocols described above for synthesizing compound 4-1 and in Scheme 8. Simple modification includes the use of different acids, different benzyl or pyridinyl amines for amide formation and different amines in the carbamate formation. The acid used for 4-5 was prepared from ethyl phenylacetoacetate by reduction with sodium borohydride and hydrolysis of the ester and the acid used for 4-6 was prepared by a known method disclosed in Wang, Z.-M., et al., *Synlett*. 1993, 8, 603, followed by the hydrolysis to the acid.

TABLE 4

| Ex. | Structure | Nomenclature | (LC/MS) or HRMS (M + 1 or M + 1 − $H_2O$) |
|---|---|---|---|
| 4-1 | 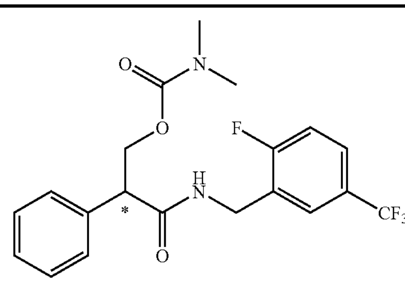 | (2R or 2S)-3-{[2-fluoro-5-(trifluoromethyl)benzyl]amino}-3-oxo-2-phenylpropyl dimethylcarbamate | 413.1491 |
| 4-2 | 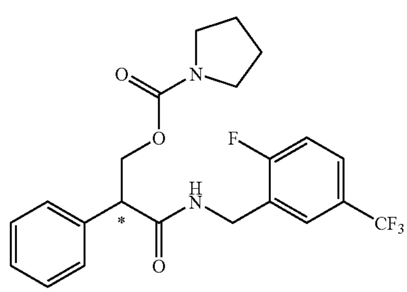 | (2R or 2S)-3-{[2-fluoro-5-(trifluoromethyl)benzyl]amino}-3-oxo-2-phenylpropyl pyrrolidine-1-carboxylate | 439.1641 |
| 4-3 | 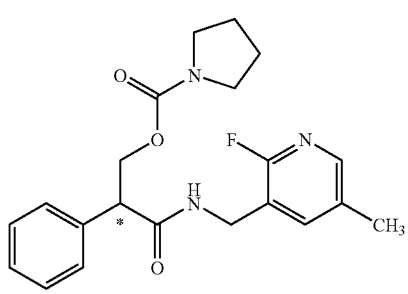 | (2R or 2S)-3-{[(2-fluoro-5-methylpyridin-3-yl)methyl]amino}-3-oxo-2-phenylpropyl pyrrolidine-1-carboxylate | 386.2 |

TABLE 4-continued

| Ex. | Structure | Nomenclature | (LC/MS) or HRMS (M + 1 or M + 1 − H₂O) |
|---|---|---|---|
| 4-4 | 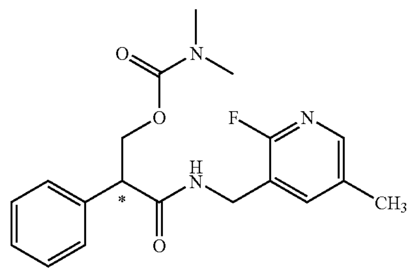 | (2R or 2S)-3-{[(2-fluoro-5-methylpyridin-3-yl)methyl]amino}-3-oxo-2-phenylpropyl dimethylcarbamate | 360.1 |
| 4-5 | 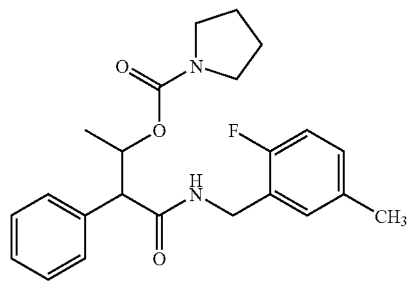 | 3-{[2-fluoro-5-(trifluoromethyl)benzyl]amino}-1-methyl-3-oxo-2-phenylpropylpyrrolidine-1-carboxylate | 453.1804 |
| 4-6 | 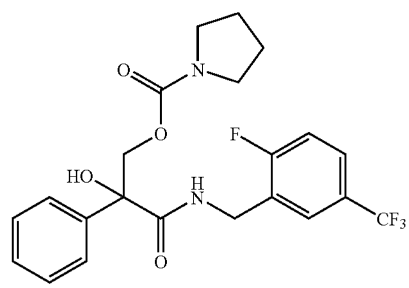 | 3-{[2-fluoro-5-(trifluoromethyl)benzyl]amino}-2-hydroxy-3-oxo-2-phenylpropylpyrrolidine-1-carboxylate | 455.2 |

Example 5

Pharmaceutical Composition

As a specific embodiment of this invention, 100 mg of (2R or 2S)-3-{[2-fluoro-5-(trifluoromethyl)benzyl]amino}-3-oxo-2-phenylpropyl, is formulated with sufficient finely divided lactose to provide a total amount of 580 to 590 mg to fill a size 0, hard gelatin capsule.

While the foregoing specification teaches the principles of the present invention, with examples provided for the purpose of illustration, it is understood that the practice of the invention encompasses all of the usual variations, adoptions, or modifications, as being within the scope of the following claims and their equivalents.

ASSAYS

In Vitro and In Vivo Assays for SARM Activity Identification of Compounds

The compounds exemplified in the present application exhibited activity in one or more of the following assays.

Hydroxylapatite-based Radioligand Displacement Assay of Compound Affinity for Endogenously Expressed AR Materials:

Binding Buffer: TEGM (10 mM Tris-HCl, 1 mM EDTA, 10% glycerol, 1 mM beta-mecaptoethanol, 10 mM Sodium Molybdate, pH 7.2)

50% HAP Slurry: Calbiochem Hydroxylapatite, Fast Flow, in 10 mM Tris, pH 8.0 and 1 mM EDTA.

Wash Buffer: 40 mM Tris, pH7.5, 100 mM KCl, 1 mM EDTA and 1 mM EGTA.

95% EtOH

Methyltrienolone, [17α-methyl-$^3$M], (R1881*); NEN NET590

Methyltrienolone (R1881), NEN NLP005 (dissolve in 95% EtOH)

Dihydrotestosterone (DHT) [1,2,4,5,6,7-$^3$H(N)] NEN NET453

Hydroxylapatite Fast Flow; Calbiochem Cat#391947

Molybdate=Molybdic Acid (Sigma, M1651)

MDA-MB-453 Cell Culture Media:

| RPMI 1640 (Gibco 11835-055) w/23.8 mM NaHCO$_3$, 2 mM L-glutamine in 500 mL of complete media | Final conc. |
|---|---|
| 10 mL (1M Hepes) | 20 mM |
| 5 mL (200 mM L-glu) | 4 mM |
| 0.5 mL (10 mg/mL human insulin) in 0.01N HCl Calbiochem#407694-S) | 10 μg/mL |
| 50 mL FBS (Sigma F2442) | 10% |
| 1 mL (10 mg/mL Gentamicin Gibco#15710-072) | 20 μg/mL |

Cell Passaging

Cells (Hall R. E., et al., *European Journal of Cancer*, 30A: 484-490 (1994)) are rinsed twice in PBS, phenol red-free Trypsin-EDTA is diluted in the same PBS 1:10. The cell layers are rinsed with 1× Trypsin, extra Trypsin is poured out, and the cell layers are incubated at 37° C. for ~2 min. The flask is tapped and checked for signs of cell detachment. Once the cells begin to slide off the flask, the complete media is added to kill the trypsin. The cells are counted at this point, then diluted to the appropriate concentration and split into flasks or dishes for further culturing (Usually 1:3 to 1:6 dilution).

Preparation of MDA-MB-453 Cell Lysate

When the MDA cells are 70 to 85% confluent, they are detached as described above, and collected by centrifuging at 1000 g for 10 minutes at 4° C. The cell pellet is washed twice with TEGM (10 mM Tris-HCl, 1 mM EDTA, 10% glycerol, 1 mM beta-mercaptoethanol, 10 mM Sodium Molybdate, pH 7.2). After the final wash, the cells are resuspended in TEGM at a concentration of $10^7$ cells/mL. The cell suspension is snap frozen in liquid nitrogen or ethanol/dry ice bath and transferred to −80° C. freezer on dry ice. Before setting up the binding assay, the frozen samples are left on ice-water to just thaw (~1 hr). Then the samples are centrifuged at 12,500 g to 20,000 g for 30 min at 4° C. The supernatant is used to set-up assay right away. If using 50 μL of supernatant, the test compound can be prepared in 50 μL of the TEGM buffer.

Procedure for Multiple Compound Screening

1×TEGM buffer is prepared, and the isotope-containing assay mixture is prepared in the following order: EtOH (2% final concentration in reaction), $^3$H-R1881 or $^3$H-DHT (0.5 nM final Conc. in reaction) and 1×TEGM. [eg. For 100 samples, 200 μL (100×2) of EtOH+4.25 μL of 1:10 $^3$H-R1881 stock+2300 μL (100×23) 1×TEGM]. The compound is serially diluted, e.g., if starting final conc. is 1 μM, and the compound is in 25 μL of solution, for duplicate samples, 75 μL of 4×1 μM solution is made and 3 μL of 100 μM is added to 72 μL of buffer, and 1:5 serial dilution.

25 μL of $^3$H-R1881 trace and 25 μL compound solution are first mixed together, followed by addition of 50 μL receptor solution. The reaction is gently mixed, spun briefly at about 200 rpm and incubated at 4° C. overnight. 100 μL of 50% HAP slurry is prepared and added to the incubated reaction which is then vortexed and incubated on ice for 5 to 10 minutes. The reaction mixture is vortexed twice more to resuspend HAP while incubating reaction. The samples in 96-well format are then washed in wash buffer using The FilterMate™ Universal Harvester plate washer (Packard). The washing process transfers HAP pellet containing ligand-bound expressed receptor to Unifilter-96 GF/B filter plate (Packard). The HAP pellet on the filter plate is incubated with 50 μL of MICROSCINT (Packard) scintillant for 30 minutes before being counted on the TopCount microscintillation counter (Packard). $IC_{50}$s are calculated using R1881 as a reference.

The compounds, Examples 1-1 through 1-19, and Examples 2-1 through 2-15, found in Tables 1 and 2, were tested in the above assay and found to have an $IC_{50}$ value of 1 micromolar or less.

Mammalian Two-Hybrid Assay for the Ligand-induced Interaction of N-Terminus and C-Terminus Domains of the Androgen Receptor (Agonist Mode: VIRCON)

This assay assesses the ability of AR agonists to induce the interaction between the N-terminal domain (NTD) and C-terminal domain (CTD) of rhAR that reflects the in vivo virilizing potential mediated by activated androgen receptors. The interaction of NTD and CTD of rhAR is quantified as ligand induced association between a Gal4 DBD-rhARCTD fusion protein and a VP16-rhARNTD fusion protein as a mammalian two-hybrid assay in CV-1 monkey kidney cells.

The day before transfection, CV-1 cells are trypsinized and counted, and then plated at 20,000 cells/well in 96-well plates or larger plates (scaled up accordingly) in DMEM+10% FCS. The next morning, CV-1 cells are cotransfected with pCBB1 (Gal4 DBD-rhARLBD fusion construct expressed under the SV40 early promoter), pCBB2 (VP16-rhAR NTD fusion construct expressed under the SV40 early promoter) and pFR (Gal4 responsive luciferase reporter, Promega) using LIPO-FECTAMINE PLUS reagent (GMCO-BRL) following the procedure recommended by the vendor. Briefly, DNA admixture of 0.05 μg pCBB1, 0.05 μg pCBB2 and 0.1 μg of pFR is mixed in 3.4 μL OPTI-MEM (GIBCO-BRL) mixed with "PLUS Reagent" (1.6 μL, GIBCO-BRL) and incubated at room temperature (RT) for 15 min to form the pre-complexed DNA.

For each well, 0.4 μL LIPOFECTAMINE Reagent (GIBCO-BRL) is diluted into 4.6 μL OPTI-MEM in a second tube and mixed to form the diluted LIPOFECTAMINE Reagent. The pre-complexed DNA (above) and the diluted LIPOFECTAMINE Reagent (above) are combined, mixed and incubated for 15 minutes at room temperature. The medium on the cells is replaced with 40 μL/well OPTI-MEM, and 10 μL DNA-lipid complexes are added to each well. The complexes are mixed into the medium gently and incubated at 37° C. at 5% $CO_2$ for 5 hours. Following incubation, 200 μL/well D-MEM and 13% charcoal-stripped FCS are added, followed by incubation at 37° C. at 5% $CO_2$. After 24 hours, the test compounds are added at the desired concentration(s) (1 nM-10 μM). Forty eight hours later, luciferase activity is measured using LUC-Screen system (TROPIX) following the manufacturer's protocol. The assay is conducted directly in the wells by sequential addition of 50 μL each of assay solution 1 followed by assay solution 2. After incubation for 40 minutes at room temperature, luminescence is directly measured with 2-5 second integration.

Activity of test compounds is calculated as the $E_{max}$ relative to the activity obtained with 3 nM R1881. Typical tissue-selective androgen receptor modulators of the present invention display weak or no agonist activity in this assay with less than 50% agonist activity at 10 micromolar.

See He B. Kemppainen J A, Voegel J J, Gronemeyer H, Wilson E M, "Activation function in the human androgen receptor ligand binding domain mediates inter-domain communication with the NH(2)-terminal domain," *J. Biol. Chem.* 274: 37219-37225 (1999). *Trans-Activation Modulation of Androgen Receptor (TAMAR)*

This assay assesses the ability of test compounds to control transcription from the MMTV-LUC reporter gene in MDA-MB-453 cells, a human breast cancer cell line that naturally expresses the human AR. The assay measures induction of a modified MMTV LTR/promoter linked to the LUC reporter gene.

20,000 to 30,000 cells/well are plated in a white, clear-bottom 96-well plate in "Exponential Growth Medium" which consists of phenol red-free RPMI 1640 containing 10% FBS, 4 mM L-glutamine, 20 mM HEPES, 10 ug/mL human insulin, and 20 ug/mL gentamicin. Incubator conditions are 37° C. and 5% $CO_2$. The transfection is done in batch mode. The cells are trypsinized and counted to the right cell number in the proper amount of fresh media, and then gently mixed with the Fugene/DNA cocktail mix and plated onto the 96-well plate. All the wells receive 200 Tl of medium+lipid/DNA complex and are then incubated at 37° C. overnight. The transfection cocktail consists of serum-free Optimem, Fugene6 reagent and DNA. The manufacturer's (Roche Biochemical) protocol for cocktail setup is followed. The lipid (TI) to DNA (Tg) ratio is approximately 3:2 and the incubation time is 20 minutes at room temperature. Sixteen to 24 hrs after transfection, the cells are treated with test compounds such that the final DMSO (vehicle) concentration is <3%. The cells are exposed to the test compounds for 48 hours. After 48 hours, the cells are lysed by a Promega cell culture lysis buffer for 30-60 minutes and then the luciferase activity in the extracts is assayed in the 96-well format luminometer.

Activity of test compounds is calculated as the $E_{max}$ relative to the activity obtained with 100 nM R1881.

See R. E. Hall, et al., "MDA-MB-453, an androgen-responsive human breast carcinoma cell line with high androgen receptor expression," *Eur. J. Cancer*, 30A: 484-490 (1994) and R. E. Hall, et al., "Regulation of androgen receptor gene expression by steroids and retinoic acid in human breast-cancer cells," *Int. J. Cancer*, 52: 778-784 (1992).

Activity of test compounds is calculated as the $E_{max}$ relative to the activity obtained with R1881. The exemplified tissue selective androgen receptor modulators of the present invention display partial agonist activity in this assay of greater than 10%.

In Vivo Prostate Assay

Male Sprague-Dawley rats aged 9-10 weeks, the earliest age of sexual maturity, are used in prevention mode. The goal is to measure the degree to which androgen-like compounds delay the rapid deterioration (~-85%) of the ventral prostate gland and seminal vesicles that occurs during a seven day period after removal of the testes (orchiectomy [ORX]).

Rats are orchiectomized (ORX). Each rat is weighed, then anesthetized by isoflurane gas that is maintained to effect. A 1.5 cm anteroposterior incision is made in the scrotum. The right testicle is exteriorized. The spermatic artery and vas deferens are ligated with 4.0 silk 0.5 cm proximal to the testicle. The testicle is freed by one cut of a small surgical scissors distal to the ligation site. The tissue stump is returned to the scrotum. The same is repeated for the left testicle. When both stumps are returned to the scrotum, the scrotum and overlying skin are sutured closed with 4.0 silk. For Sham-ORX, all procedures excepting ligation and scissors cutting are completed. The rats fully recover consciousness and full mobility within 10-15 minutes.

A dose of test compound is administered subcutaneously or orally to the rat immediately after the surgical incision is sutured. Treatment continues for an additional six consecutive days.

Necropsy and Endpoints

The rat is first weighed, then anesthetized in a $CO_2$ chamber until near death. Approximately 5 ml whole blood is obtained by cardiac puncture. The rat is then examined for certain signs of death and completeness of ORX. Next, the ventral portion of the prostate gland is located and blunt dissected free in a highly stylized fashion. The ventral prostate is blotted dry for 3-5 seconds and then weighed (VPW). Finally, the seminal vesicle is located and dissected free. The ventral seminal vesicle is blotted dry for 3-5 seconds and then weighed (SVWT).

Primary data for this assay are the weights of the ventral prostate and seminal vesicle. Secondary data include serum LH (luteinizing hormone) and FSH (follicle stimulating hormone), and possible serum markers of bone formation and virilization. Data are analyzed by ANOVA plus Fisher PLSD post-hoc test to identify intergroup differences. The extent to which test compounds inhibit ORX-induced loss of VPW and SVWT is assessed.

In Vivo Bone Formation Assay:

Female Sprague-Dawley rats aged 7-10 months are used in treatment mode to simulate adult human females. The rats have been ovariectomized (OVX) 75-180 days previously, to cause bone loss and simulate estrogen deficient, osteopenic adult human females. Pre-treatment with a low dose of a powerful anti-resorptive, alendronate (0.0028 mpk SC, 2x/wk) is begun on Day 0. On Day 15, treatment with test compound is started. Test compound treatment occurs on Days 15-31 with necropsy on Day 32. The goal is to measure the extent to which androgen-like compounds increase the amount of bone formation, shown by increased fluorochrome labeling, at the periosteal surface.

In a typical assay, nine groups of seven rats each are studied.

On Days 19 and 29 (fifth and fifteenth days of treatment), a single subcutaneous injection of calcein (8 mg/kg) is given to each rat.

Necropsy and Endpoints

The rat is first weighed, then anesthetized in a $CO_2$ chamber until near death. Approximately 5 mL whole blood is obtained by cardiac puncture. The rat is then examined for certain signs of death and completeness of OVX. First, the uterus is located, blunt dissected free in a highly stylized fashion, blotted dry for 3-5 seconds and then weighed (UW). The uterus is placed in 10% neutral-buffered formalin. Next, the right leg is disarticulated at the hip. The femur and tibia are separated at the knee, substantially defleshed, and then placed in 70% ethanol.

A 1-cm segment of the central right femur, with the femoral proximal-distal midpoint ats center, is placed in a scintillation vial and dehydrated and defatted in graded alcohols and acetone, then introduced to solutions with increasing concentrations of methyl methacrylate. It is embedded in a mixture of 90% methyl methacrylate: 10% dibutyl phthalate that is allowed to polymerize over a 48-72 hours period. The bottle is cracked and the plastic block is trimmed into a shape that conveniently fits the vice-like specimen holder of a Leica 1600 Saw Microtome, with the long axis of the bone prepared for cross-sectioning. Three cross-sections of 85 µm thickness are prepared and mounted on glass slides. One section from each rat that approximates the midpoint of the bone is selected and blind-coded. The periosteal surface of each section is assessed for total periosteal surface, single fluorochrome label, double fluorochrome label, and interlabel distance.

Primary data for this assay are the percentage of periosteal surface bearing double label and the mineral apposition rate (interlabel distance(μm)/10d), semi-independent markers of bone formation. Secondary data include uterus weight and histologic features. Tertiary endpoints can include serum markers of bone formation and virilization. Data are analyzed by ANOVA plus Fisher PLSD post-hoc test to identify inter-group differences. The extent to which test compounds increase bone formation endpoint are assessed.

What is claimed is:

1. A method of treating benign prostate hyperplasia, comprising administering to the mammal in need of such treatment, a therapeutically effective amount of a compound which is

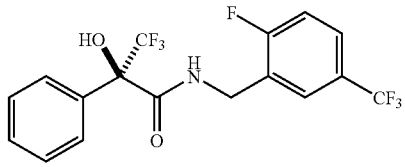

(2R)-3,3,3-trifluoro-N-(2-fluoro-5-trifluoromethylbenzyl)-2-hydroxy-2-phenylpropanamide or a pharmaceutically acceptable salt thereof.

* * * * *